(12) United States Patent
Boudreaux et al.

(10) Patent No.: US 10,507,035 B2
(45) Date of Patent: Dec. 17, 2019

(54) SURGICAL INSTRUMENT PROVIDING ULTRASONIC TISSUE EMULSIFICATION AND ULTRASONIC SHEARING

(71) Applicant: Ethicon Endo-Surgery, LLC, Guaynabo, PR (US)

(72) Inventors: Chad P. Boudreaux, Cincinnati, OH (US); Jeffrey D. Messerly, Cincinnati, OH (US); Ion V. Nicolaescu, Carpentersville, IL (US); Foster B. Stulen, Mason, OH (US); Charles J. Scheib, Loveland, OH (US); Mary E. Mootoo, Cincinnati, OH (US); Matthew C. Miller, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 353 days.

(21) Appl. No.: 15/285,167

(22) Filed: Oct. 4, 2016

(65) Prior Publication Data
US 2017/0105752 A1  Apr. 20, 2017

Related U.S. Application Data

(60) Provisional application No. 62/243,723, filed on Oct. 20, 2015, provisional application No. 62/360,549, filed on Jul. 11, 2016.

(51) Int. Cl.
*A61B 17/3203* (2006.01)
*A61B 17/32* (2006.01)
*A61B 18/14* (2006.01)

(52) U.S. Cl.
CPC .. *A61B 17/3203* (2013.01); *A61B 17/320092* (2013.01); *A61B 18/1442* (2013.01);
(Continued)

(58) Field of Classification Search
CPC ............... A61B 17/32; A61B 17/3203; A61B 17/320068; A61B 2017/320072; A61B 18/14; A61B 18/1445; A61B 17/320004
See application file for complete search history.

(56) References Cited

U.S. PATENT DOCUMENTS 5,322,055 A  6/1994 Davison et al.
5,628,743 A  5/1997 Cimino
(Continued)

FOREIGN PATENT DOCUMENTS

EP  2 361 693 A2  8/2011
EP  2 581 053 A1  4/2013

OTHER PUBLICATIONS

International Search Report and Written Opinion dated Jan. 20, 2017 for Application No. PCT/US2016/057291, 15 pgs.
(Continued)

*Primary Examiner* — Vi X Nguyen
(74) *Attorney, Agent, or Firm* — Frost Brown Todd LLC

(57) ABSTRACT

An instrument includes an ultrasonic blade, a first fluid port in communication with the distal opening of the ultrasonic blade, a clamp arm, an irrigation member positioned adjacent to the distal end of the ultrasonic blade, and a second fluid port in communication with the irrigation member. The ultrasonic blade defines a distal opening. The ultrasonic blade is operable in a first mode to emulsify tissue that is distally positioned relative to the ultrasonic blade. The ultrasonic blade is further operable in a second mode to transect and seal tissue that is transversely positioned relative to the ultrasonic blade. The clamp arm is pivotable toward and away from the ultrasonic blade.

20 Claims, 37 Drawing Sheets

(52) U.S. Cl.
CPC ............ *A61B 2017/320069* (2017.08); *A61B 2017/320071* (2017.08); *A61B 2017/320084* (2013.01); *A61B 2017/320089* (2017.08); *A61B 2017/320094* (2017.08); *A61B 2017/320095* (2017.08); *A61B 2217/005* (2013.01)

(56) References Cited

U.S. PATENT DOCUMENTS

| | | |
|---|---|---|
| 5,873,873 A | 2/1999 | Smith et al. |
| 5,980,510 A | 11/1999 | Tsonton et al. |
| 6,325,811 B1 | 12/2001 | Messerly |
| 6,454,781 B1 | 9/2002 | Witt et al. |
| 6,773,444 B2 | 8/2004 | Messerly |
| 6,783,524 B2 | 8/2004 | Anderson et al. |
| 8,057,498 B2 | 11/2011 | Robertson |
| 8,152,825 B2 | 4/2012 | Madan et al. |
| 8,461,744 B2 | 6/2013 | Wiener et al. |
| 8,591,536 B2 | 11/2013 | Robertson |
| 8,623,027 B2 | 1/2014 | Price et al. |
| 8,986,302 B2 | 3/2015 | Aldridge et al. |
| 9,023,071 B2 | 5/2015 | Miller et al. |
| 9,044,261 B2 | 6/2015 | Houser |
| 9,095,367 B2 | 8/2015 | Olson et al. |
| 9,381,058 B2 | 7/2016 | Houser et al. |
| 9,393,037 B2 | 7/2016 | Olson et al. |
| 2006/0079874 A1 | 4/2006 | Faller et al. |
| 2007/0083120 A1 | 4/2007 | Cain et al. |
| 2007/0191713 A1 | 8/2007 | Eichmann et al. |
| 2007/0282333 A1 | 12/2007 | Fortson et al. |
| 2008/0015473 A1 | 1/2008 | Shimizu |
| 2008/0200940 A1 | 8/2008 | Eichmann et al. |
| 2012/0116265 A1 | 5/2012 | Houser et al. |
| 2013/0190623 A1 | 7/2013 | Bertolina et al. |
| 2015/0080879 A1* | 3/2015 | Trees ................ A61B 18/1445 606/40 |

OTHER PUBLICATIONS

U.S. Appl. No. 61/410,603, filed Nov. 5, 2010.
U.S. Appl. No. 62/360,549, filed Jul. 11, 2016.
U.S. Appl. No. 62/243,723, filed Oct. 20, 2015.

* cited by examiner

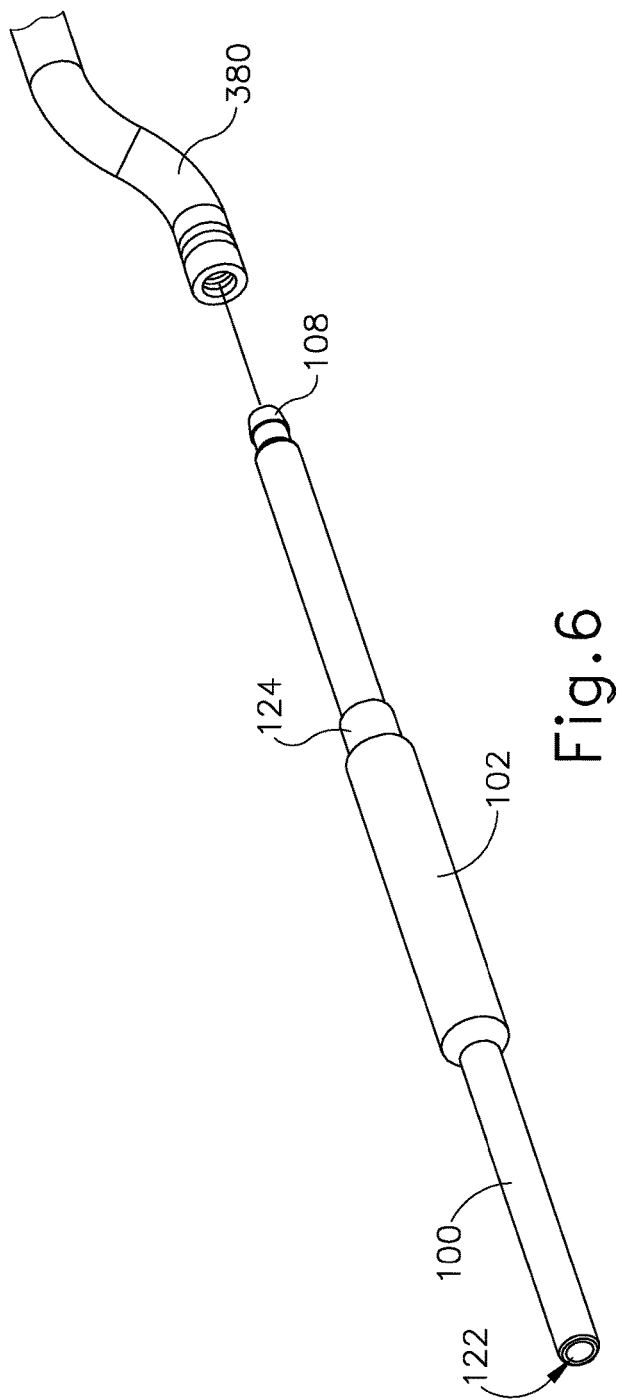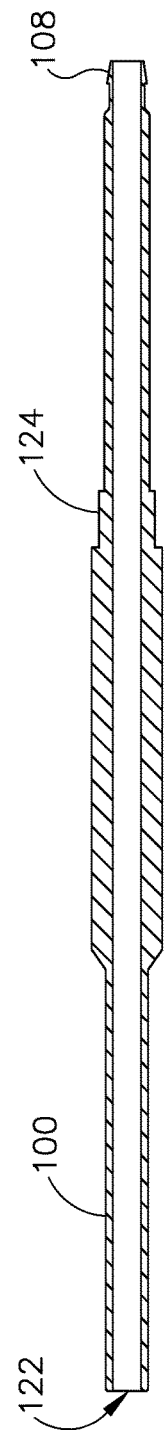

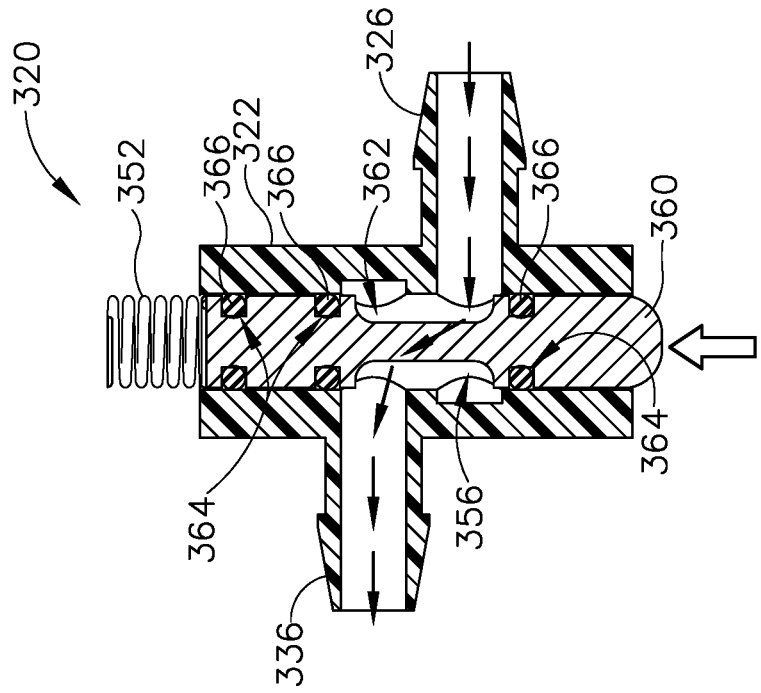
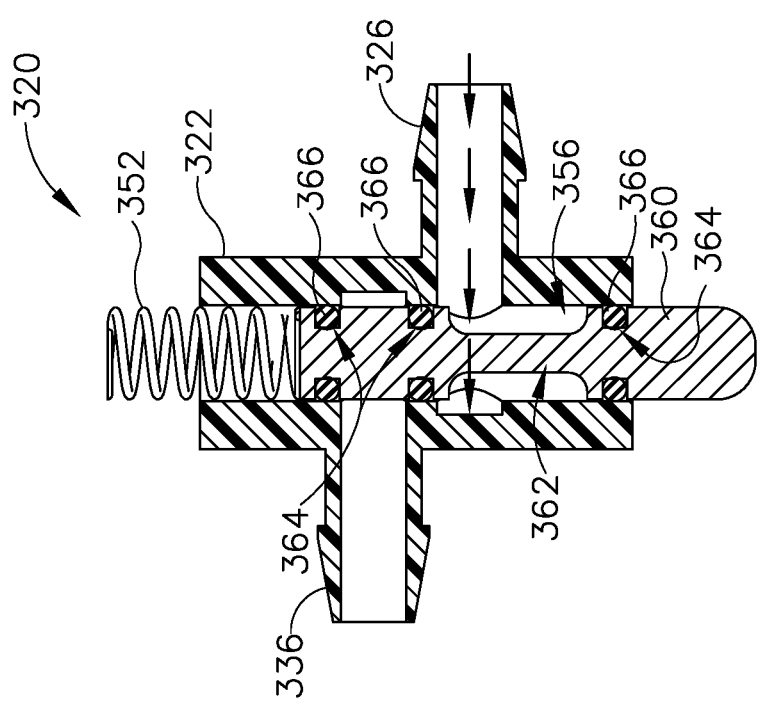

SURGICAL INSTRUMENT PROVIDING ULTRASONIC TISSUE EMULSIFICATION AND ULTRASONIC SHEARING

PRIORITY

This application claims priority to U.S. Patent App. No. 62/360,549, entitled "Surgical Instrument Providing Ultrasonic Tissue Emulsification and Ultrasonic Shearing," filed Jul. 11, 2016, the disclosure of which is incorporated by reference herein.

This application also claims priority to U.S. Patent App. No. 62/243,723, entitled "Surgical Instrument Providing Ultrasonic Tissue Emulsification and Ultrasonic Shearing," filed Oct. 20, 2015, the disclosure of which is incorporated by reference herein.

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2009/0105750, entitled "Ergonomic Surgical Instruments," published Apr. 23, 2009, issued as U.S. Pat. No. 8,623,027 on Jan. 7, 2014, the disclosure of which is incorporated by reference herein; U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; and U.S. Pub. No. 2012/0029546, entitled "Ultrasonic Surgical Instrument Blades," published Feb. 2, 2012, issued as U.S. Pat. No. 8,591,536 on Nov. 26, 2013, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. patent application Ser. No. 13/538,588, filed Jun. 29, 2012, issued as U.S. Pat. No. 9,393,037 on Jul. 19, 2016, entitled "Surgical Instruments with Articulating Shafts," the disclosure of which is incorporated by reference herein; and U.S. patent application Ser. No. 13/657,553, filed Oct. 22, 2012, issued as U.S. Pat. No. 9,095,367 on Aug. 4, 2015, entitled "Flexible Harmonic Waveguides/Blades for Surgical Instruments," the disclosure of which is incorporated by reference herein.

Some ultrasonic surgical instruments may include a clamp feature to press tissue against the ultrasonic blade of the end effector. Examples of such an arrangement (sometimes referred to as a clamp coagulator shears or an ultrasonic transector) is disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; and U.S. Pat. No. 6,325,811, entitled "Blades with Functional Balance Asymmetries for use with Ultrasonic Surgical Instruments," issued Dec. 4, 2001, the disclosure of which is incorporated by reference herein. Some versions of clamp coagulator shears utilize handles that are either of a pistol or scissors grips design. The scissor grip designs may have one thumb or finger grip that is immovable and fixed to the housing; and one movable thumb or finger grip. Some designs have scissor arms that extend from the grips, with one of the arms rotating around a fixed pivot or rotation point that is perpendicular to the longitudinal axis of the working element. The operator may thus squeeze a handgrip or other feature to drive a clamp arm, to thereby press the clamp pad toward the blade.

Some ultrasonic devices may be used to provide acoustic cavitation. When acoustic cavitation is used to break down soft tissue, the process may be referred to as "histotripsy." Examples of histotripsy techniques and associated technology are described in U.S. Pub. No. 2007/0083120, entitled "Pulsed Cavitational Ultrasound Therapy," published Apr. 12, 2007, now abandoned, the disclosure of which is incorporated by reference herein; U.S. Pub. No. 2013/0190623, entitled "Histotripsy Therapy Transducer," published Jul. 25, 2013, now abandoned, the disclosure of which is incorporated by reference herein; and U.S. Pat. No. 8,057,408, entitled "Pulsed Cavitational Ultrasound Therapy," issued Nov. 15, 2011, the disclosure of which is incorporated by reference herein. A somewhat similar procedure is known as lithotripsy, where shock waves are used to break up kidney stones. Such shock waves may be generated by an ultrasonic transducer.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 6 depicts an exploded perspective view of a distal waveguide of the ultrasonic vibration transmission components of FIG. 5 separated from a suction tube of the suction transmission components of FIG. 5;

FIG. 7 depicts a cross-sectional side view of the distal waveguide of FIG. 6;

FIG. 14A depicts a cross-sectional view of the valve assembly of FIG. 11, taken along line 14-14 of FIG. 11, with the valve assembly in a closed state;

FIG. 14B depicts a cross-sectional view of the valve assembly of FIG. 11, taken along line 14-14 of FIG. 11, with the valve assembly in an open state;

Figure 1:
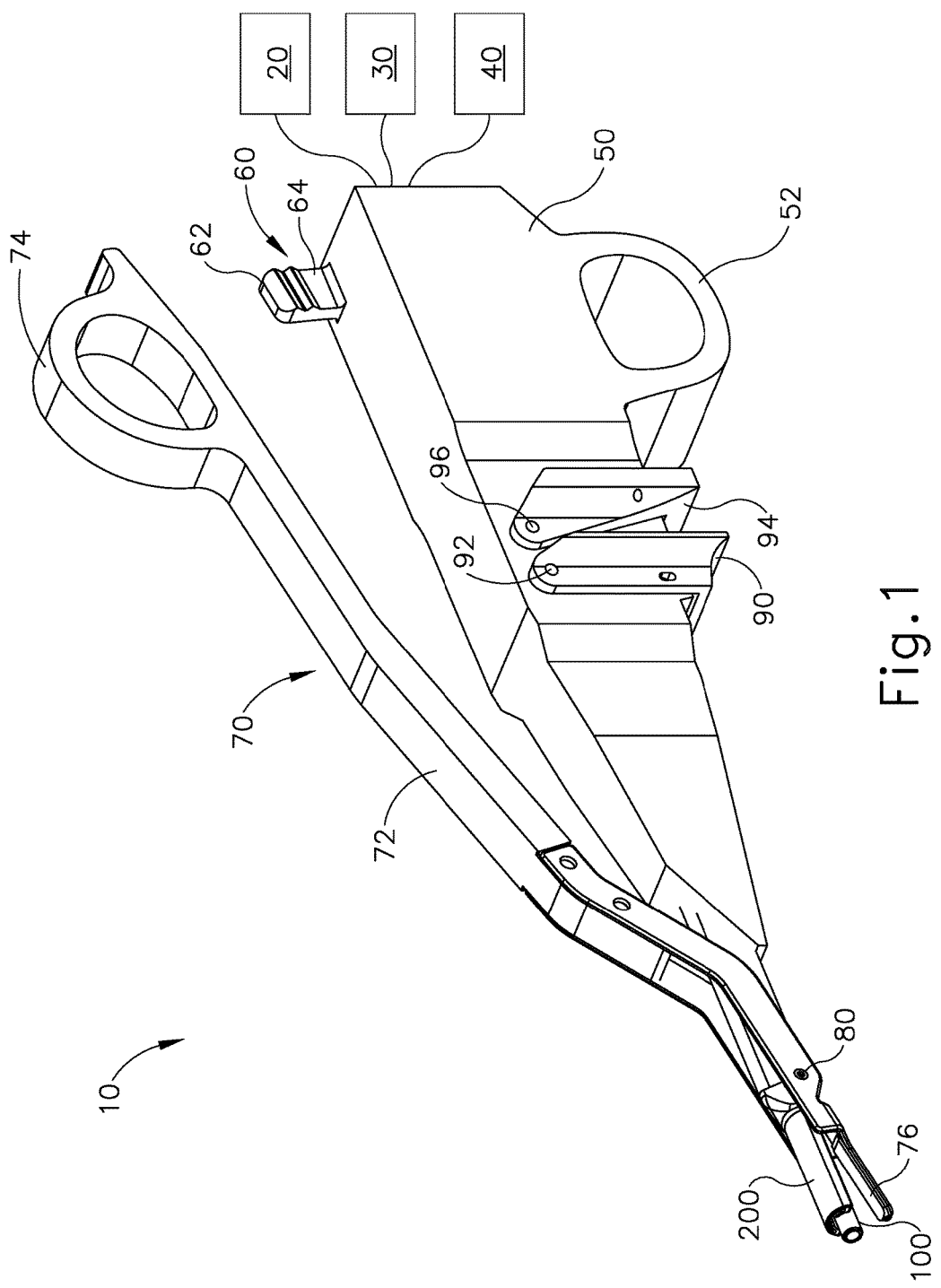
FIG. 1 depicts a perspective view of an exemplary ultrasonic surgical system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers the position of an element closer to the operator or other operator and the term "distal" refers to the position of an element closer to the surgical end effector of the surgical instrument and further away from the operator or other operator.

I. Overview of Exemplary Ultrasonic Surgical System

In some surgical procedures, it may be desirable to operate an ultrasonic debriding instrument to dissect tissue by applying ultrasonic vibrational energy to the tissue. In the same surgical procedure, it may be desirable to operate an ultrasonic shears instrument to transect tissue by compressing the tissue against an ultrasonically activated element. In conventional instrumentation, this may require the use of two separate instruments. This is because, even though both types of instruments rely on activation of an ultrasonically vibrating element, the debriding instrument may act on tissue that is positioned distal to the ultrasonically vibrating element (e.g., along the longitudinal axis of the ultrasonically vibrating element); while the clamping transection instrument may act on tissue that is positioned transverse to the ultrasonically vibrating element (e.g., perpendicular to the longitudinal axis of the ultrasonically vibrating element). It may therefore be desirable to provide a single instrument that is operable to both provide dissection of tissue that is distal to an ultrasonically vibrating element and provide clamping transection in tissue that is positioned transverse to the ultrasonically vibrating element. Several merely illustrative examples of such an instrument are described in greater detail below.

It should be understood that the instruments described below may be used in a variety of clinical contexts. By way of example only, the instruments described below may be used to remove portions of a liver. In some such uses, the ultrasonically vibrating element may be used like a scalpel to dissect the parenchyma of the liver. This process may ultimately reveal one or more blood vessels and/or biliary ducts. In some such instances (e.g., where a vessel or duct having a diameter greater than approximately 1 mm is encountered), the scalpel-like mode of operation may not be an ideal mode to use for transecting and sealing such vessels and/or ducts. The operator may thus use a scalpel-like mode of operation to separate parenchymal tissue from vessels and biliary ducts in the liver, then transition use of the instrument to a clamping transection mode of operation in order to transect and seal the one or more blood vessels and/or biliary ducts. Various ways in which this may be accomplished will be described in greater detail below. It should be understood that integrating both modes of operation may reduce the number of instruments used in a surgical procedure, thereby simplifying the surgical procedure; and enabling the operator to keep the surgical field within their view the entire time that they are transitioning between modes of operation (whereas using two instruments may require the operator to avert their eyes from the surgical field, which may cause the operator to have difficulty finding the vessels/ducts that are to be transected). It should also be understood that this clinical context and method of operation is merely one of many possible contexts and methods in which the below described instruments may be used. Various other suitable contexts and methods in which the below described instruments may be used will be apparent to those of ordinary skill in the art in view of the teachings herein.

FIGS. 1-5 depict an exemplary instrument (10) that may be used to both provide an ultrasonic scalpel type of dissection in tissue that is distal to an ultrasonic blade (100) and provide clamping transection in tissue that is positioned transverse to ultrasonic blade (100). Instrument (10) of this example is coupled with a generator (20), a fluid source (30), and a suction source (40). Instrument (10) includes a handle assembly (50), a clamp arm assembly (70), and an irrigation flue (200) in addition to ultrasonic blade (100).

By way of example only, generator (20) may comprise the GEN04, GEN11, or GEN 300 sold by Ethicon Endo-Surgery, Inc. of Cincinnati, Ohio. In addition, or in the alternative, generator (20) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. Alternatively, any other suitable generator (20) may be used. As will be described in greater detail below, generator (20) is operable to provide power to instrument (10) to perform ultrasonic surgical procedures Fluid source (30) may contain saline and/or any other suitable kind(s) of fluid(s). It should also be understood that the fluid may comprise a high surface tension fluid with or without bubbles. In some versions, fluid source (30) comprises a passive reservoir that is positioned to provide fluid to instrument (10) via gravity feed. In some other versions, fluid source (30) includes a fluid pump and/or some other feature(s) that is/are operable to pressurize fluid for deliver to and through instrument (10). Various suitable forms that fluid source (30) may take, as well as various kinds of fluids that may be used, will be apparent to those of ordinary skill in the art in view of the teachings herein.

Suction source (40) may comprise any suitable source of suction. For instance, suction source (40) may comprise a conventional vacuum wall outlet that leads to a centralized vacuum system. Of course, one or more fluid reservoirs, filters, and/or other components may be interposed between instrument (10) and a conventional vacuum wall outlet. As another merely illustrative example, suction source (40) may comprise a vacuum pump that is situated locally with instrument (10). As yet another merely illustrative example, suction source (40) may be integrated into a single piece of capital equipment along with generator (20) and/or fluid source (30). Various other suitable forms that suction source (40) may take will be apparent to those of ordinary skill in the art in view of the teachings herein.

Handle assembly (50) of the present example includes an integral finger ring (52) through which an operator's finger may be inserted to facilitate gripping of handle assembly (50). Handle assembly (50) further includes a ratchet feature (60) and a pair of actuators (90, 94), such as triggers (90, 94). Each trigger (90, 94) is pivotably coupled with handle assembly (50) by a respective pin (92, 96). Ratchet feature (60) and triggers (90, 94) will be described in greater detail below. As shown ultrasonic blade (100) and irrigation flue (200) project distally from handle assembly (50).

Clamp arm assembly (70) comprises a shank (72), a thumb ring (74), and a clamp pad (76). Shank (72) is pivotably coupled with handle assembly (50) by a pin (80). Thumb ring (74) is configured to receive an operator's thumb to facilitate actuation of clamp arm assembly (70). It should therefore be understood that finger ring (52) and thumb ring (74) together enable an operator to grasp and manipulate instrument (10) using a scissor grip. Of course, such a configuration is merely optional. In some variations, instrument (10) is modified to provide a pistol grip with a pivoting trigger to control a clamp arm assembly. Various examples of such a configuration are shown and described in numerous references cited herein. As yet another merely illustrative example, some versions of instrument (10) may substitute handle assembly (50) and clamp arm assembly (70) with features that are coupled to a robotic surgical system that is configured to operate instrument (10) (e.g., via remote control, etc.).

Clamp arm assembly (70) is operable to pivot clamp pad (72) toward and away from ultrasonic blade (100). Clamp arm assembly (70) is thus operable to compress tissue between clamp pad (72) and ultrasonic blade (100). Those of ordinary skill in the art will recognize that, when ultrasonic blade (100) is activated to vibrate ultrasonically, the compression of tissue against ultrasonic blade (100) by clamp pad (72) may assist in further driving the ultrasonic vibrations of ultrasonic blade (100) through the tissue, thereby promoting transection and sealing of the tissue. By way of example only, clamp pad (72) may comprise polytetrafluoroethylene (PTFE) to reduce adhesion of tissue to clamp pad (72). Other suitable material(s) and/or configurations that may be incorporated into clamp pad (72) will be apparent to those of ordinary skill in the art in view of the teachings herein.

It should also be understood that ultrasonic blade (100) may include various materials to prevent or reduce adhesion of tissue to blade (100). By way of example only, the distal external surface of ultrasonic blade (100) in the region of clamp pad (72) may be coated with a polymer such as Xylan to further reduce the potential for sticking. In addition, the inner surface defining lumen (122) of ultrasonic blade (100) may be coated with a polymer to help lessen the occurrence of clogging. Various other suitable materials that may be incorporated into ultrasonic blade (100) will be apparent to those of ordinary skill in the art in view of the teachings herein.

A. Exemplary Ultrasonic Communication Features

Figure 2:
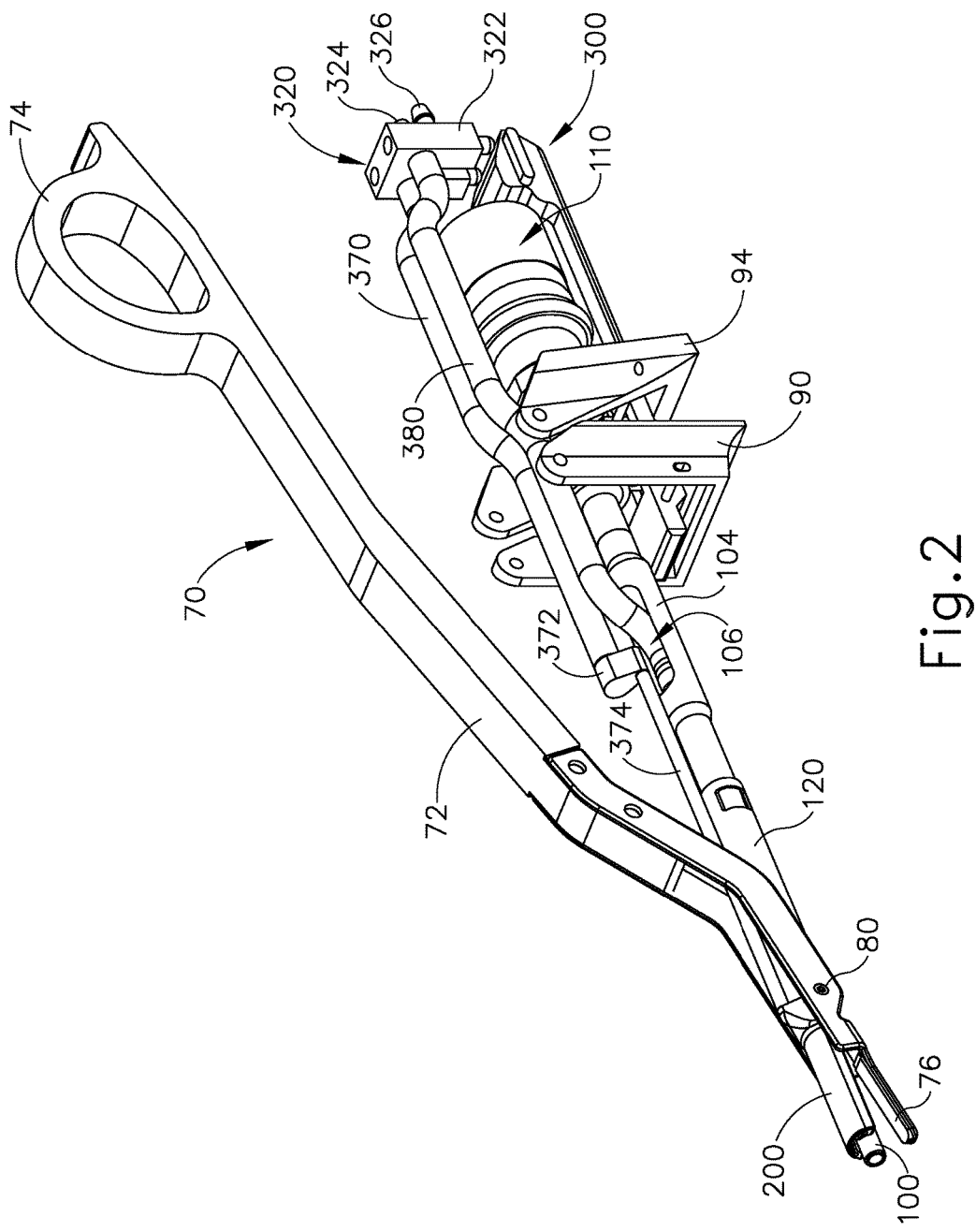
FIG. 2 depicts a perspective view of an ultrasonic surgical instrument of the system of FIG. 1, with a body of the instrument omitted for clarity.

As best seen in FIG. 2, an ultrasonic transducer assembly (110) is contained in handle assembly (50). Ultrasonic transducer assembly (110) receives electrical power from generator (20). Ultrasonic transducer assembly (110) includes a plurality of piezoelectric elements such that ultrasonic transducer assembly (110) is operable to convert electrical power from generator (20) into ultrasonic vibrational energy. Ultrasonic transducer assembly (110) of the present example includes two conductive rings (not shown) that are securely disposed within the body of ultrasonic transducer assembly (110) as is described in U.S. Pub. No. 2007/0106158, entitled "Medical Ultrasound System and Handpiece and Methods for Making and Tuning," published May 10, 2007, issued as U.S. Pat. No. 8,152,825 on Apr. 10, 2012, the disclosure of which is incorporated by reference herein. Other suitable forms that ultrasonic transducer assembly (110) may take will be apparent to those of ordinary skill in the art in view of the teachings herein.

Figure 4:
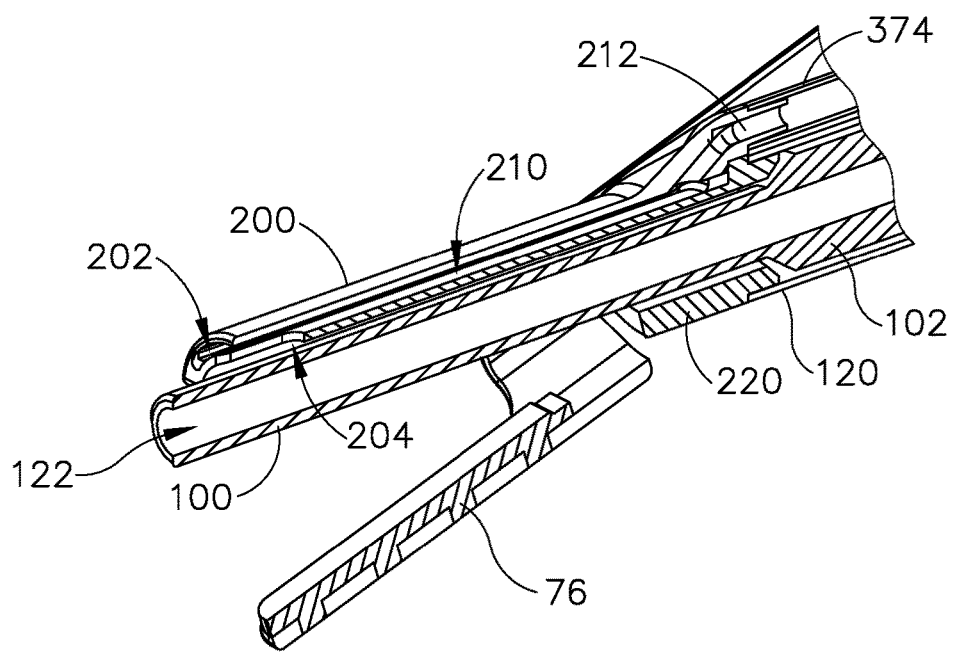
FIG. 4 depicts a cross-sectional perspective view of the end effector of FIG. 3, with the end effector in an open configuration.

As best seen in FIGS. 2 and 4, a proximal waveguide segment (104) is secured to the distal end of ultrasonic transducer assembly (110). A distal waveguide segment (102) is secured to the distal end of proximal waveguide segment (104). In particular, proximal waveguide segment (104) is secured to a coupling feature (124) (FIGS. 6-7) of distal waveguide segment (102). By way of example only, segments may be coupled together through welding, interference fitting, threaded coupling, and/or any other suitable form of coupling. Ultrasonic blade (100) is formed by the distal end of distal waveguide segment (102).

Figure 5:
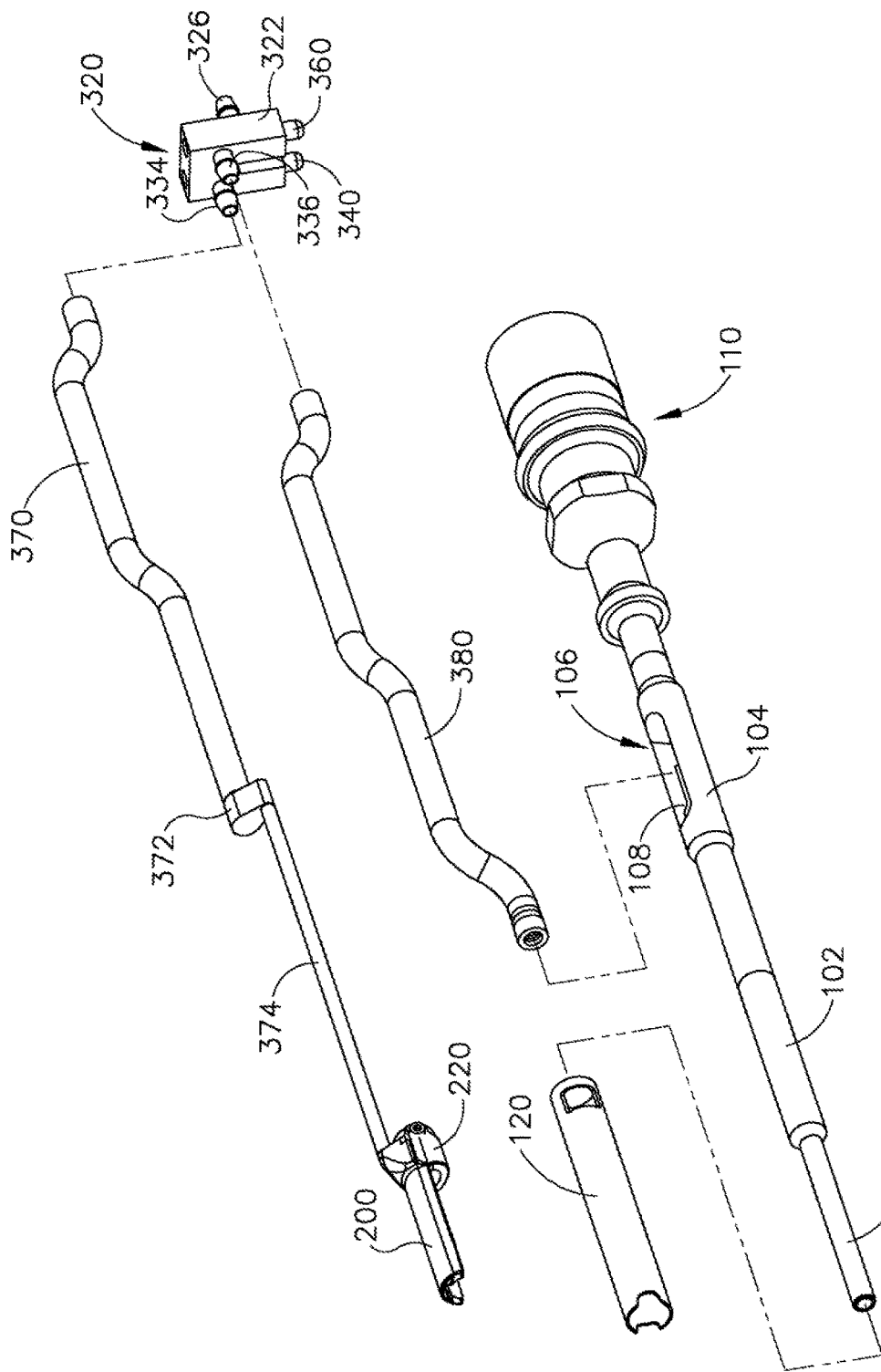
FIG. 5 depicts an exploded view of ultrasonic vibration transmission components, suction transmission components, and irrigating fluid transmission components of the instrument of FIG. 2.

In the present example, ultrasonic blade (100) is integral with distal waveguide segment (102), such that blade (100) and segment (102) are formed together as a single unit. In some versions, ultrasonic blade (100) may be connected to distal waveguide segment (102) by a threaded connection, a welded joint, and/or some other coupling feature(s). It should be understood that ultrasonic transducer assembly (110), segments (102, 104), and ultrasonic blade (100) together form an acoustic drivetrain, such that ultrasonic vibrations generated by ultrasonic transducer assembly (110) will be communicated along segments (102, 104) to blade (100). In some instances, coupling feature (124) is located at a longitudinal position corresponding to a node associated with ultrasonic vibrations communicated along segments (102, 104). Handle assembly (50) and clamp arm assembly (70) are configured to substantially isolate the operator from the vibrations of the acoustic assembly formed by ultrasonic transducer assembly (110), segments (102, 104), and ultrasonic blade (100). In addition, as shown in FIGS. 2 and 4-5, a distal sheath (120) is positioned about an otherwise exposed portion of distal waveguide segment (102), shielding distal waveguide segment (102) from inadvertent contact. Segments (102, 104) and ultrasonic blade (100) may be fabricated from a solid core shaft constructed out of a material or combination of materials that propagates ultrasonic energy efficiently, such as titanium alloy (i.e., Ti-6Al-4V), aluminum alloys, sapphire, ceramics (e.g., aluminum oxide, etc.), stainless steel, or any other acoustically compatible material or combination of materials.

FIGS. 6-7 show ultrasonic blade (100) in greater detail. As shown, ultrasonic blade (100) of this example defines a lumen (122) such that ultrasonic blade (100) is hollow with open distal and proximal ends. The proximal end of ultrasonic blade (100) includes a barbed fitting (108). A suction tube (380) is coupled with barbed fitting (108) in a fluid-tight manner. It should therefore be understood that suction may be applied to the distal end of ultrasonic blade (100) via suction tube (380) and lumen (122). Suction tube (380) is further coupled with a valve assembly (320) as will be described in greater detail below. As best seen in FIGS. 2-5, proximal waveguide segment (104) defines a lateral opening (106), such as a lateral channel (106), that is configured to accommodate the distal end of suction tube (380). In particular, suction tube (380) passes through lateral channel (106) to reach barbed fitting (108). Distal waveguide segment (102) thus receives suction from suction tube (380) despite the fact that segments (102, 104) are longitudinally aligned and coupled with each other. Other suitable ways in which suction may be provided through distal waveguide segment (102) will be apparent to those of ordinary skill in the art in view of the teachings herein.

When ultrasonic transducer assembly (110) of the present example is activated, these mechanical oscillations are transmitted through waveguide segments (102, 104) to reach ultrasonic blade (100), thereby providing oscillation of ultrasonic blade (100) at the resonant ultrasonic frequency. In the present example, the distal end of ultrasonic blade (100) is located at a position corresponding to an anti-node associated with resonant ultrasonic vibrations communicated through waveguide segments (102, 104). When ultrasonic transducer assembly (110) is energized, the distal end of ultrasonic blade (100) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. The distal tip of ultrasonic blade (100) may also vibrate in the y-axis at about 1 to about 10 percent of the motion in the x-axis. Of course, movement of the distal tip of ultrasonic blade (100) may alternatively have any other suitable characteristics. By way of example only, the distal tip of ultrasonic blade (100) may vibrate with more movement in the y-axis than in the x-axis. As another merely illustrative example, the distal tip of ultrasonic blade (100) may vibrate in the y-axis at up to about 50 percent of the motion in the x-axis. Other suitable vibrational characteristics will be apparent to those of ordinary skill in the art in view of the teachings herein. In the present example, the ultrasonic oscillation of ultrasonic blade (100) may simultaneously sever the tissue and denature the proteins in adjacent tissue cells, thereby providing a coagulative effect with relatively little thermal spread.

B. Exemplary Irrigation Flue

Figure 8:
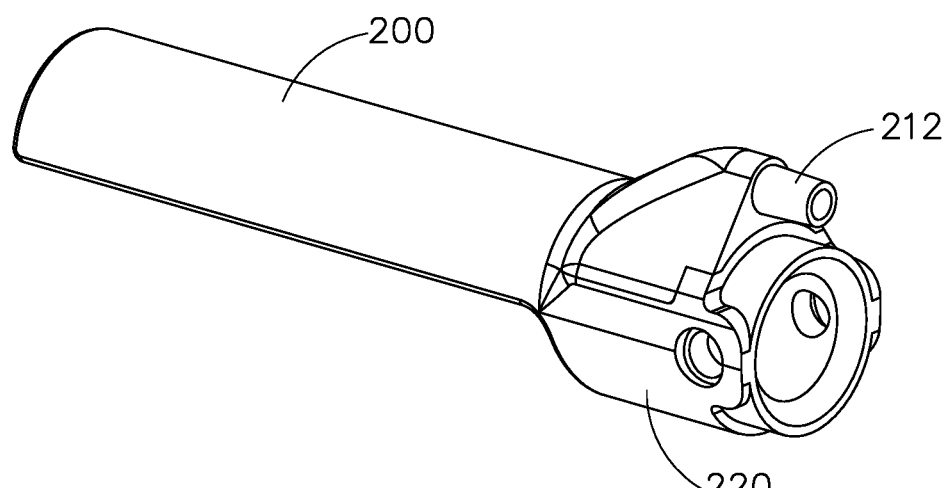
FIG. 8 depicts a perspective view of an irrigation flue of the irrigating fluid transmission components of FIG. 5.
Figure 9:
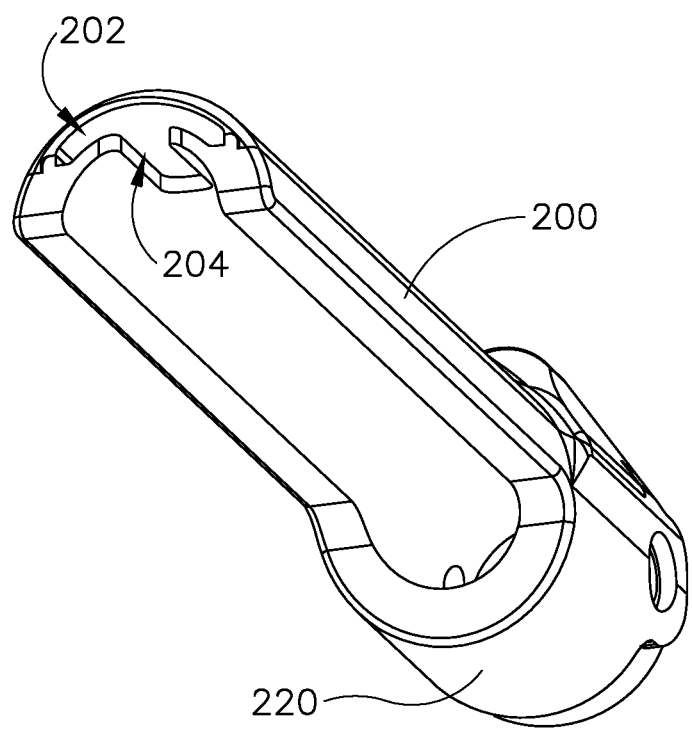
FIG. 9 depicts another perspective view of the irrigation flue of FIG. 8.
Figure 10:
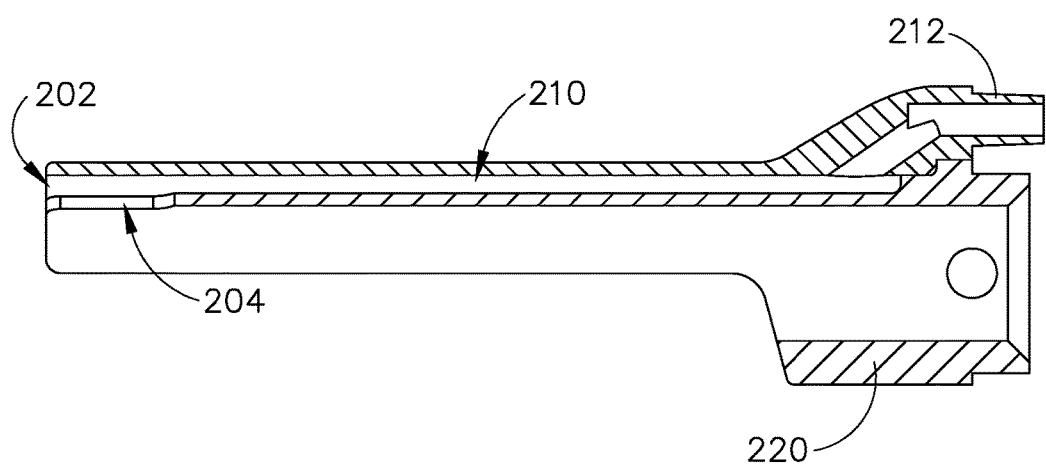
FIG. 10 depicts a cross-sectional side view of the irrigation flue of FIG. 8.
Figure 11:
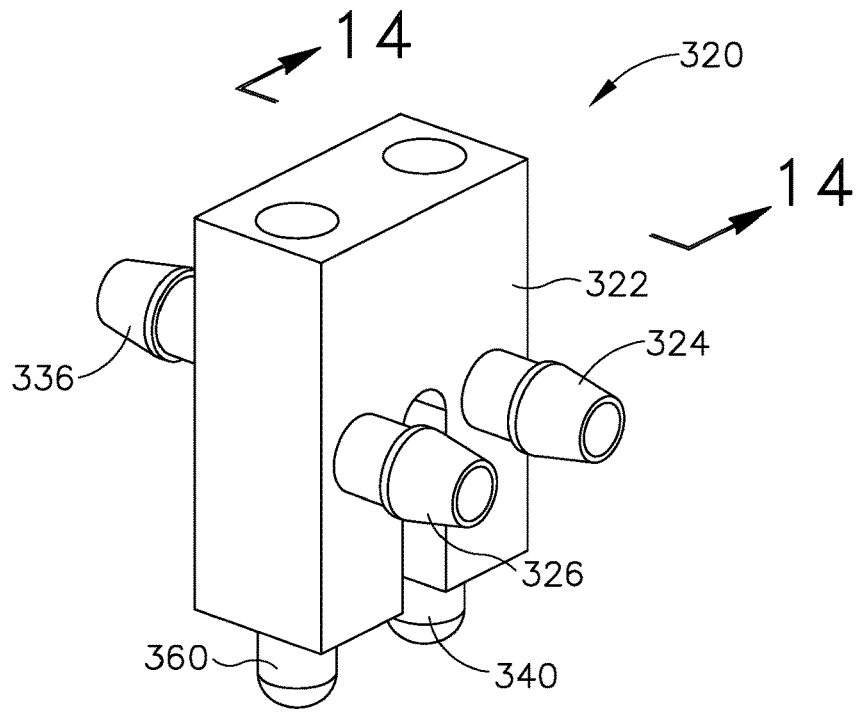
FIG. 11 depicts a perspective view of a valve assembly of the suction and irrigating fluid transmission components of FIG. 5.
Figure 12:
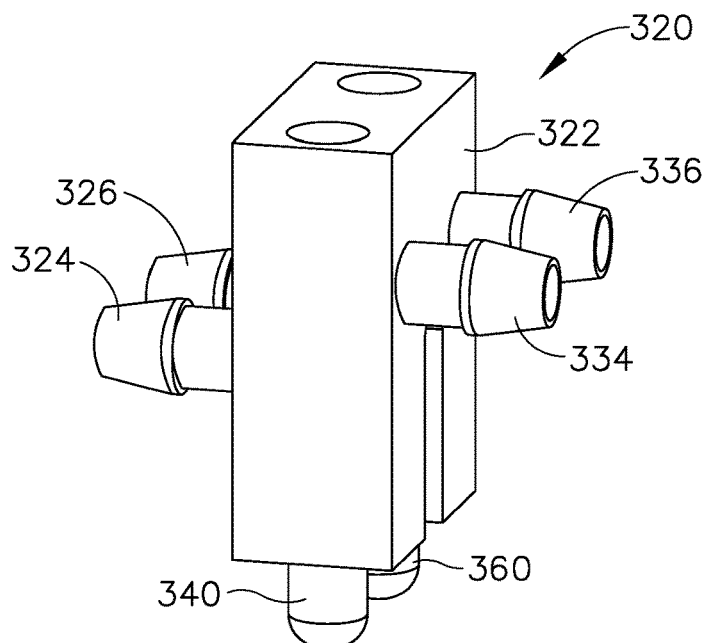
FIG. 12 depicts another perspective view of the valve assembly of FIG. 11.

FIGS. 8-10 show irrigation flue (200) in greater detail. As shown, irrigation flue (200) of this example comprises an open distal end (202), a slot (204), a lumen (210), a fluid port (212), and a hub (220). Slot (204) extends longitudinally from open distal end (202). Open distal end (202), slot (204), and fluid port (212) are all in fluid communication with lumen (210). Fluid port (212) is configured to couple with a distal fluid tube (374), as shown in FIGS. 2 and 4-5. Fluid tube (374) is coupled with a fitting (372), which is further coupled with a proximal fluid tube (370). Proximal fluid tube (470) is further coupled with valve assembly (320) as will be described in greater detail below. It should be understood that the fluid from fluid source (30) may be communicated through open distal end (202) and slot (204) via valve assembly (320), proximal fluid tube (370), fitting (372), distal fluid tube (374), port (212), and lumen (210).

Hub (220) is secured to the distal end of sheath (120), such that the position of irrigation flue (200) is longitudinally and pivotably fixed relative to the position of ultrasonic blade (100) (other than the vibrational movement of ultrasonic blade (100) relative to irrigation flue (200)).

Figure 3:
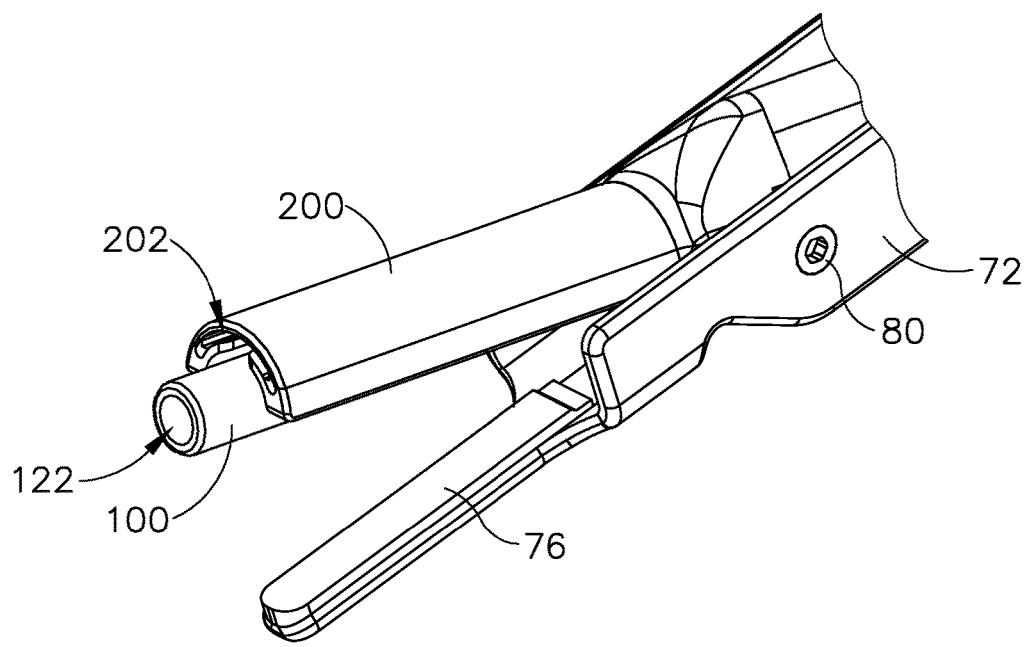
FIG. 3 depicts a perspective view of an end effector of the instrument of FIG. 2, with the end effector in an open configuration.

As best seen in FIGS. 3-4, irrigation flue (200) extends about a portion of the circumferential perimeter of ultrasonic blade (100), though irrigation flue (200) is sized and configured to maintain a gap between irrigation flue (200) and the distal end of ultrasonic blade (100). In the present example, irrigation flue (200) has a semi-circular cross-sectional profile with an angular extent of approximately 180°. This configuration and positioning prevents irrigation flue (200) from interfering with compression of tissue against ultrasonic blade (100) by clamp pad (76). Of course, this configuration is just one merely illustrative example. For instance, irrigation flue (200) may instead have a semi-circular cross-sectional profile with an angular extent that is less than or greater than approximately 180°. As another merely illustrative example, irrigation flue (200) may have a full circular cross-sectional profile extending a full 360° about ultrasonic blade (100), such that irrigation flue (200) is provided in the form of a tube. In some such versions, the gap between the inner diameter of irrigation flue (200) and the outer diameter of ultrasonic blade (100) serves as lumen (210). Thus, flue (200) may lack a lumen like lumen (210). Also in some such versions, a lateral cutout may be formed in the tube forming flue (200) in order to accommodate a full closure motion of clamp pad (72). Other suitable configurations for irrigation flue (200) will be apparent to those of ordinary skill in the art in view of the teachings herein.

C. Exemplary Valve Assembly

FIGS. 11-14B show valve assembly (320) in greater detail. Valve assembly (320) of this example includes a body (322), a fluid inlet port (324), a suction inlet port (326), a fluid outlet port (334), and a suction outlet port (336). Each port (324, 326, 334, 336) comprises a barbed fitting in this example, though it should be understood that this is just one merely illustrative example of form each port (324, 326, 334, 336) may take. Fluid inlet port (324) is coupled with fluid source (30) via conventional tubing and/or any other suitable kind of conduit. Suction inlet port (326) is coupled with suction source (40) via conventional tubing and/or any other suitable kind of conduit. As shown in FIGS. 2 and 5, fluid outlet port (324) is coupled with proximal fluid tube (370). As also shown in FIGS. 2 and 5, suction outlet port (324) is coupled with suction tube (380).

Figure 13:
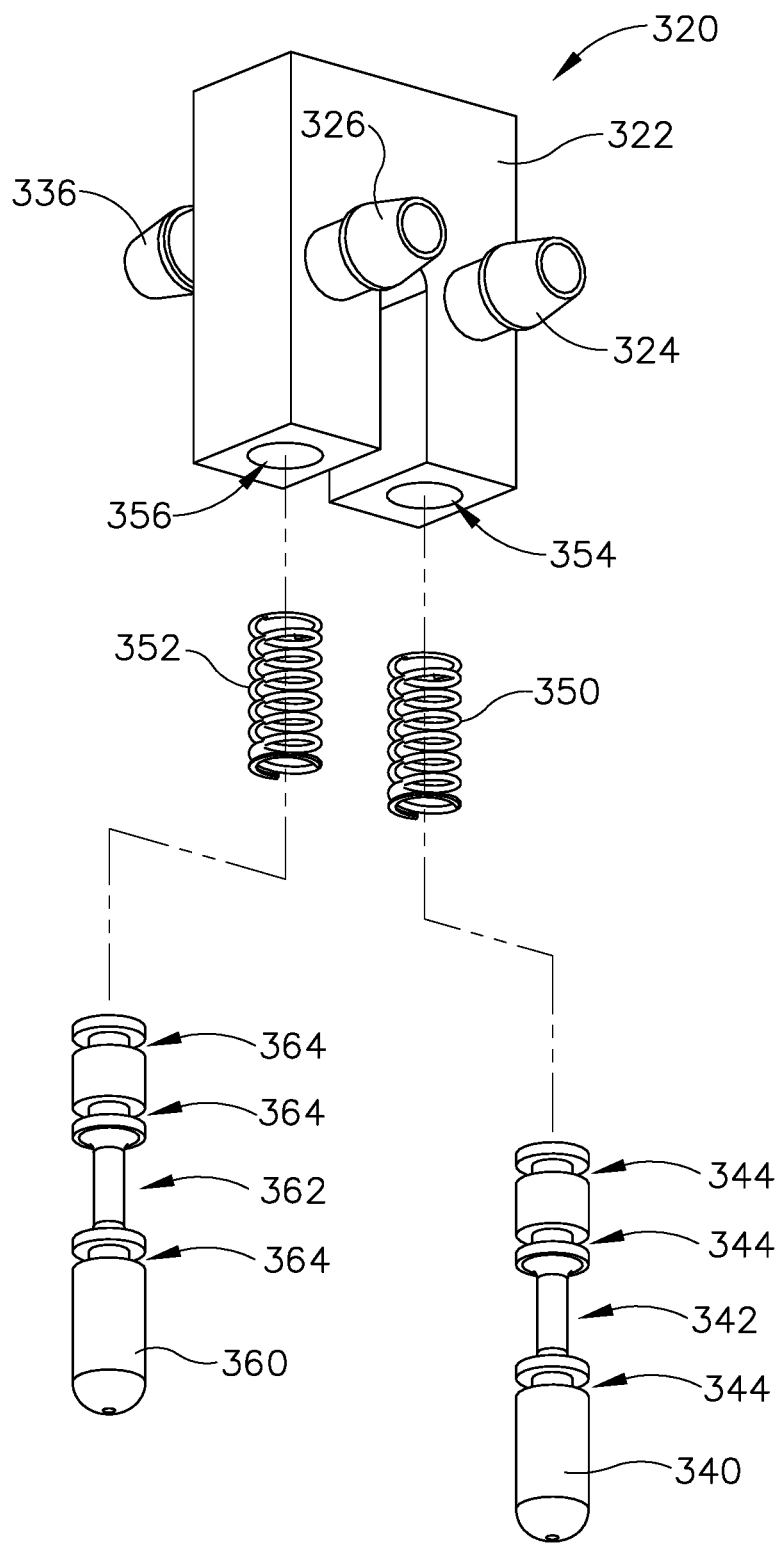
FIG. 13 depicts an exploded view of the valve assembly of FIG. 11.

Valve assembly (320) further includes a fluid valve actuator (340) and a suction valve actuator (360). Valve actuators (340, 360) are slidably disposed in corresponding bores (354, 356) formed in body (322). Fluid valve actuator (340) is configured to selectively couple fluid outlet port (334) with fluid inlet port (324), based on the position of fluid valve actuator (340) in body (322). Suction valve actuator (360) is configured to selectively couple suction outlet port (336) with suction inlet port (326), based on the position of suction valve actuator (360) in body (322). As best seen in FIG. 13, fluid valve actuator (340) comprises a fluid communication recess (342) and a set of o-ring recesses (344). Similarly, as shown in FIGS. 13-14B, suction valve actuator (360) comprises a suction communication recess (362) and a set of o-ring recesses (364). As shown in FIGS. 14A-14B, o-rings (366) are positioned in corresponding o-ring recesses (364). While not shown, it should be understood that o-ring recesses (344) may similarly have o-rings disposed therein.

As shown in FIGS. 13-14B, valve assembly (320) further includes a set of coil springs (350, 352) disposed in bores (354, 356). Coil spring (350) is configured to resiliently bias fluid valve actuator (340) downwardly. Coil spring (352) is configured to resiliently bias suction valve actuator (360) downwardly. In the present example, bores (354, 356) pass fully through body (322). The upper ends of coil springs (350, 352) are thus mechanically grounded against corresponding fixed features in handle assembly (50). In some other versions, the upper ends of bores (354, 356) are closed, such that the upper ends of coil springs (350, 352) are thus mechanically grounded against corresponding fixed features in body (322).

FIG. 14A shows suction valve actuator (360) in a downward position. In this position, suction communication recess (362) is in communication only with suction inlet port (326). An o-ring (366) is interposed between suction inlet port (326) and suction outlet port (336), such that ports (326, 336) are fluidly sealed from each other. In other words, suction is not provided through suction outlet port (336) in the state shown in FIG. 14A. The other o-rings (366) maintain fluid seals relative to the upper and lower ends of bore (356). FIG. 14B shows suction valve actuator (360) in an upward position. In this position, suction communication recess (362) is in fluid communication with both ports (326, 336), such that suction communication recess (362) provides a pathway for communication of suction from suction inlet port (326) to suction outlet port (336). O-rings (366) again continue to maintain fluid seals relative to the upper and lower ends of bore (356).

While not shown, it should be understood that fluid valve actuator (340) will operate in an identical manner to suction valve actuator (360). In particular, when fluid valve actuator (340) is in a downward position, fluid outlet port (334) is not in fluid communication with fluid inlet port (324). However, when fluid valve actuator (340) is in an upward position, fluid outlet port (334) is in fluid communication with fluid inlet port (324). It should be understood from the foregoing that, when both actuators (340, 360) are in the downward position, valve assembly (320) is in a closed state. When both actuators (340, 360) are in the upward position, valve assembly (320) is in an open state. Exemplary features that may be used to drive actuators (340, 360) upwardly to provide valve assembly (320) in the open state will be described in greater detail below.

D. Exemplary Actuation of Valve Assembly

FIGS. 15-18B show exemplary features that may be used to drive actuators (340, 360) upwardly to provide valve assembly (320) in the open state. In particular, FIGS. 15-18B show an exemplary cam sled (300) that is configured to translate longitudinally within handle assembly (50) to transition valve assembly (320) to the open state. Cam sled (300) includes a pair of outwardly extending flanges (302) that are slidably received in corresponding channels (not shown) in handle assembly (50) in order to provide support and alignment to cam sled (300). The distal end of cam sled (300) defines a pin opening (306) and a proximally facing button engagement surface (308). The proximal end of cam sled (300) defines a cam surface (304).

Figure 15:
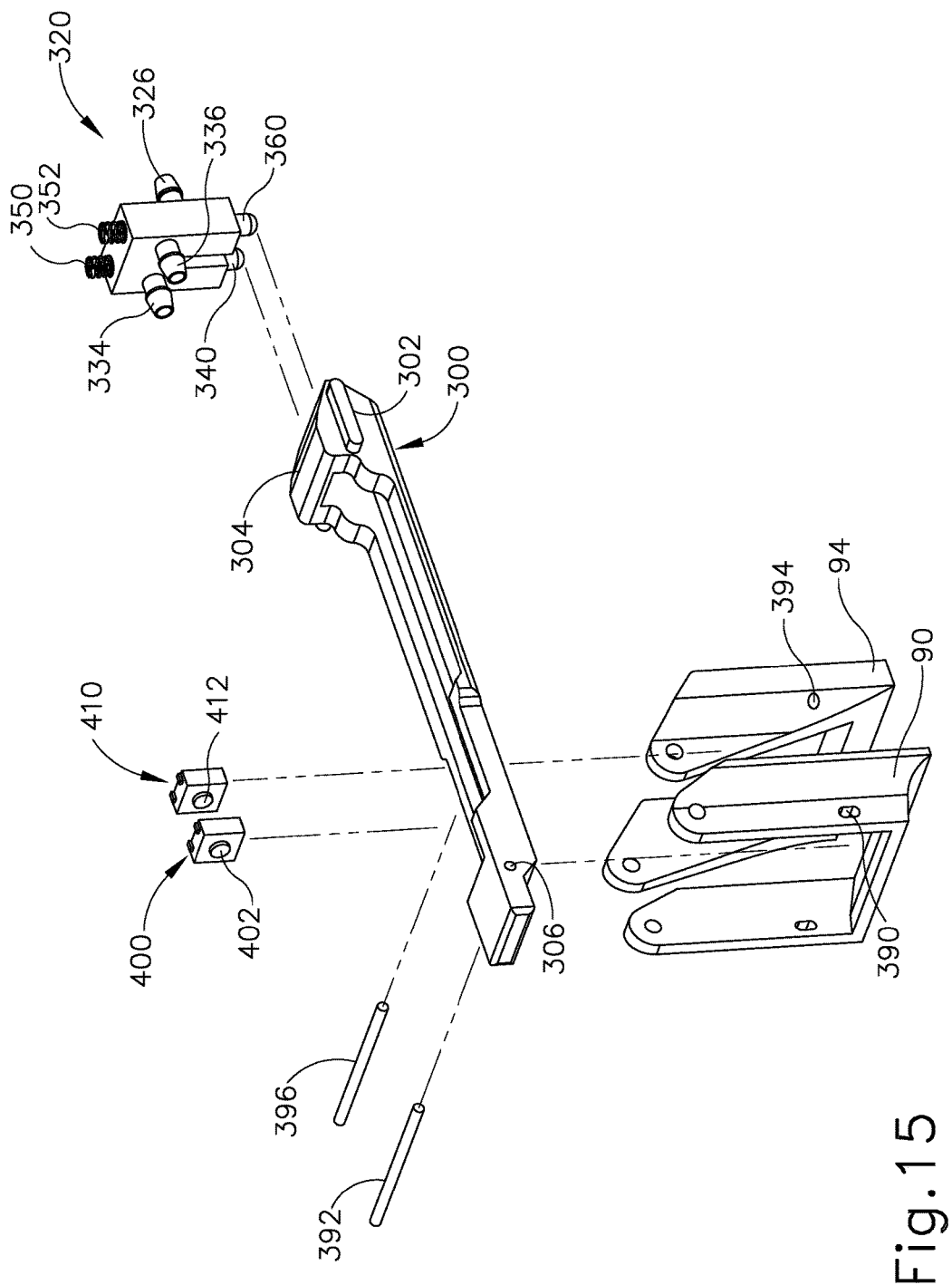
FIG. 15 depicts an exploded view of actuator components of the instrument of FIG. 2.
Figure 16:
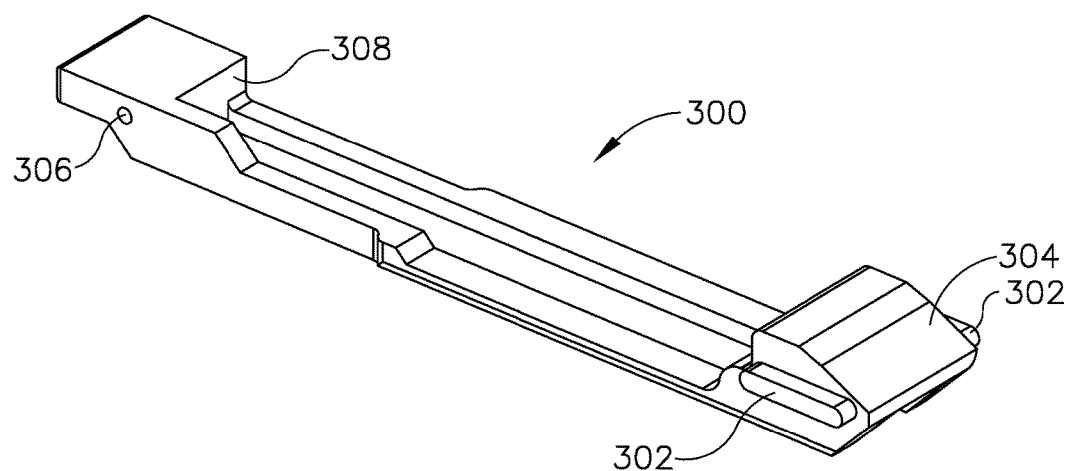
FIG. 16 depicts a perspective view of a cam sled of the actuator components of FIG. 15.
Figure 17:
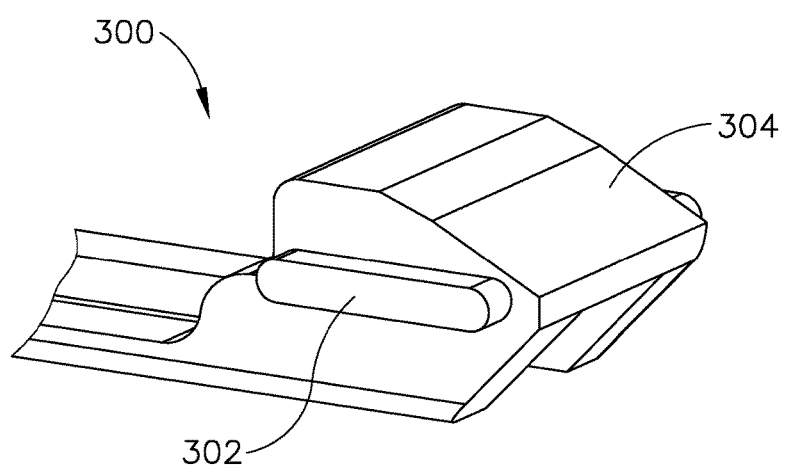
FIG. 17 depicts an enlarged perspective view of the proximal end of the cam sled of FIG. 16.
Figure 18A:
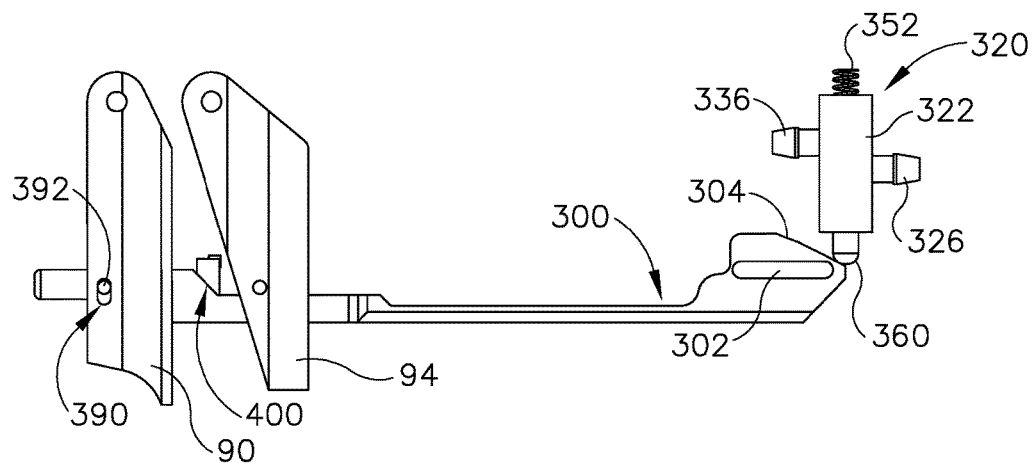
FIG. 18A depicts a side elevational view of the actuator components of FIG. 15, with a first trigger in a first pivotal position and the cam sled of FIG. 16 in a distal position.
Figure 18B:
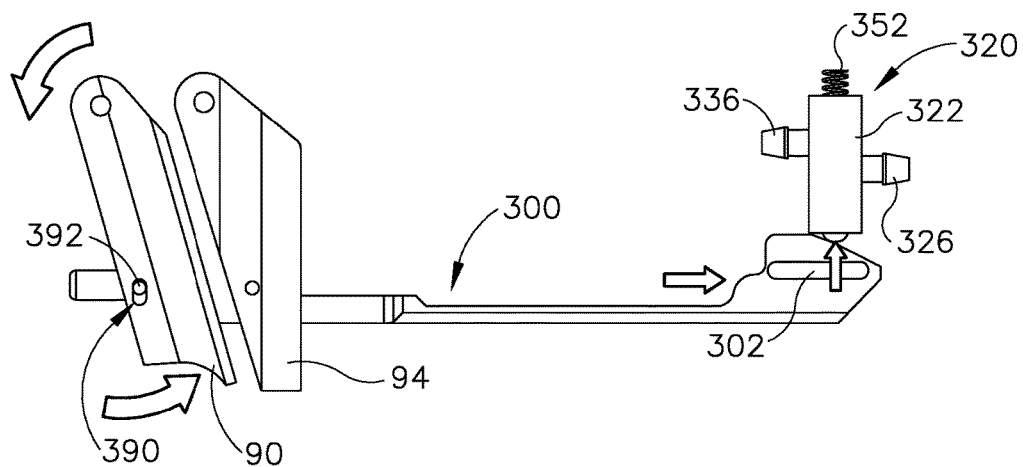
FIG. 18B depicts a side elevational view of the actuator components of FIG. 15, with the first trigger in a second pivotal position and the cam sled of FIG. 16 in a proximal position.

As shown in FIGS. 15 and 18A-18B, a pin (392) is disposed in pin opening (306). Pin (392) is also disposed in an elongate slot (390) formed through trigger (90). As noted above, trigger (90) is coupled with handle assembly (50) via a pin (92). Pin (392) is configured to translate relative to handle assembly (50) while pin (92) is not configured to translate relative to handle assembly (50). Thus, when an operator pivots trigger (90) about pin (92), trigger (90) will drive pin (392) and cam sled (300) proximally from the position shown in FIG. 18A to the position shown in FIG. 18B. As cam sled (300) translates proximally from the position shown in FIG. 18A to the position shown in FIG. 18B, cam surface (304) engages the free ends of valve actuators (340, 360) and drives both valve actuators (340, 360) upwardly simultaneously. Thus, when trigger (90) is in the unpivoted position as shown in FIG. 18A, cam sled (300) is in a distal position and valve assembly (320) is in a closed state. When trigger (90) is in the pivoted position as shown in FIG. 18B, cam sled (300) is in a proximal position and valve assembly (320) is in an open state.

When the operator releases trigger (90) from the pivoted state shown in FIG. 18B, trigger (90) may return to the unpivoted state shown in FIG. 18A, cam sled (300) may return to the distal position shown in FIG. 18A, and valve assembly (320) may return to the closed state. In some versions, the resilient bias imposed by springs (350, 352) may cause actuators (340, 360) to cooperate with cam surface (304) to drive cam sled (300) distally when the operator releases trigger (90), and the distally urged cam sled (300) may drive trigger (90) back to the unpivoted state shown in FIG. 18A. Alternatively, a resilient member (e.g., torsion spring, leaf spring, etc.) may resiliently urge trigger (90) to the unpivoted state, and the resulting movement of trigger (90) to the unpivoted state may pull cam sled (300) distally, allowing actuators (340, 360) to return to the downward positions. Other suitable ways in which valve assembly (320) may be transitioned between the open and closed states will be apparent to those of ordinary skill in the art in view of the teachings herein.

It should be understood from the foregoing that actuators (340, 360) travel upwardly simultaneously together and downwardly simultaneously together. Thus, whenever suction is being provided to ultrasonic blade (100), fluid is being provided to irrigation flue (200) and vice-versa. Similarly, whenever suction is not being provided to ultrasonic blade (100), fluid is not being provided to irrigation flue (200) and vice-versa. In some other versions, actuators (340, 360) may be actuated independently relative to each other. In some such versions, suction may be provided through blade (100) without fluid being provided through irrigation flue (200). In addition, or in the alternative, fluid may be provided through irrigation flue (200) without suction being provided through blade (100). Various suitable ways in which such functionality may be incorporated into instrument (10) will be apparent to those of ordinary skill in the art in view of the teachings herein.

E. Exemplary Ultrasonic Activation Components

As shown in FIG. 15, instrument (10) further includes a first activation button assembly (400) and a second activation button assembly (410). Each activation button assembly (400, 410) includes a corresponding activation button (402, 412). Each activation button assembly (400, 410) is in communication with generator (20). Each activation button assembly (400, 410) is operable to trigger ultrasonic activation of ultrasonic blade (100) for a corresponding mode of operation, with each mode of operation having a set of operational parameters that differs from the set of operational parameters associated with the other mode of operation.

First activation button assembly (400) and generator (20) are configured such that actuation of first activation button (402) will result in ultrasonic blade (100) vibrating at a first set of operational parameters. In the present example, this first set of operational parameters is configured to provide tissue emulsification that enables ultrasonic blade (100) to be used in a manner similar to a scalpel. In some instances, the operational parameters are selected specifically for dissection of the liver parenchyma, though this is just one merely illustrative example. By way of example only, actuation of first activation button (402) will result in ultrasonic blade (100) vibrating at a frequency of approximately 33 kHz, with a displacement of approximately 200 microns peak-to-peak at the distal end of ultrasonic blade (100). Alternatively, actuation of first activation button (402) will result in ultrasonic blade (100) vibrating at any other suitable combination of operational parameters.

Second activation button assembly (410) and generator (20) are configured such that actuation of second activation button (412) will result in ultrasonic blade (100) vibrating at a second set of operational parameters. In the present example, this second set of operational parameters is configured to provide transection and sealing of tissue that includes blood vessels, biliary ducts, and tissue bundles. By way of example only, actuation of second activation button (412) will result in ultrasonic blade (100) vibrating at a frequency of approximately 55.5 kHz, with a displacement of approximately 2 to 200 microns peak-to-peak at the distal end of ultrasonic blade (100). Alternatively, actuation of second activation button (412) will result in ultrasonic blade (100) vibrating at any other suitable combination of operational parameters.

In some versions, each button (402, 412) triggers activation of ultrasonic blade (100) at the same frequency but at a higher amplitude. In some other versions, each button (402, 412) triggers activation of ultrasonic blade (100) at the same amplitude but at a different frequency. It should also be understood that activation buttons (402, 412) may provide different energy delivery profiles such as a pulsed algorithm in one or more modes associated with either or both of buttons (402, 412). In addition, or in the alternative, either or both of activation buttons (402, 412) may trigger or otherwise affect one or more ancillary features. For instance, in some versions where instrument (10) includes one or more electrodes that are operable to apply RF electrosurgical energy to tissue (e.g., in accordance with the teachings below or otherwise), actuation of second activation button (412) may prevent the RF energy from being applied through the one or more electrodes. In other words, the RF energy may only be applied when first activation button (402) is being actuated; or when neither first activation button (402) nor second activation button (412) is being actuated. Instrument (10) may further include an additional button, footswitch, or other feature to selectively apply RF energy to tissue.

As noted above, cam sled (300) includes a proximally facing button engagement surface (308). This button engagement surface (308) is positioned to actuate first activation button (402) when cam sled (300) is driven proximally to the position shown in FIG. 18B. It should therefore be understood that ultrasonic blade (100) may be activated at the first set of operational parameters when valve assembly (320) is in the open state. In some versions, cam sled (300) is configured such that valve assembly (320) reaches the open state just before button engagement surface (308) actuates first activation button (402). In other words, trigger (90) may provide communication of suction and fluid through ultrasonic blade (100) and irrigation flue (200), respectively, after trigger (90) has been pivoted through a first range of motion; then provide activation of ultrasonic blade (100) at the first set of operational parameters while still providing communication of suction and fluid through ultrasonic blade (100) and irrigation flue (200), respectively, after trigger (90) has been pivoted through a second range of motion. Alternatively, cam sled (300) may be configured such that valve assembly (320) reaches the open state at the same time button engagement surface (308) actuates first activation button (402).

Regardless of the timing on when trigger (90) opens valve assembly (320) versus actuating activation button (402), it should also be understood that engagement surface (308) may be configured to provide tactile feedback to the operator via trigger (90) to indicate when engagement surface (308) has transitioned valve assembly (320) to the open state. For instance, the operator may encounter a first level of resistance as trigger (90) is pivoted from the position shown in FIG. 18A to a position where engagement surface (308) has transitioned valve assembly (320) to the open state. Once trigger (90) has reached a position where engagement surface (308) has transitioned valve assembly (320) to the open state, the operator may encounter a reduced level of resistance as the operator continues to pivot trigger (90). The operator may thus feel valve assembly (320) being opened when the operator feels a reduction in the resistance to pivotal movement of trigger (90). As noted above, in some versions this may occur before button engagement surface (308) actuates first activation button (402).

As shown in FIG. 15, a pin (396) is disposed in a corresponding opening (394) formed through trigger (94). As noted above, trigger (94) is coupled with handle assembly (50) via a pin (96). Pin (396) is configured to translate relative to handle assembly (50) while pin (96) is not configured to translate relative to handle assembly (50). Thus, when an operator pivots trigger (94) about pin (96), trigger (96) will drive pin (396) proximally. When pin (396) reaches a proximal position, pin (396) actuates second activation button (412). Trigger (94) is thus operable to provide activation of ultrasonic blade (100) at the second set of operational parameters. In the present example, when trigger (94) is pivoted to activate ultrasonic blade (100) at the second set of operational parameters, trigger (90) is in the unpivoted position, such that valve assembly (320) is in a closed state.

F. Exemplary Ratcheting Features to Provide Multi-Modality to Clamp Arm

It should be understood from the foregoing that instrument (10) may be selectively operated in two different modes. In the first mode, instrument (10) is used to emulsify tissue (e.g., liver parenchyma) and thereby dissect the tissue, based on actuation of trigger (90), with suction and fluid provided through ultrasonic blade (100) and irrigation flue (200), respectively. The fluid from irrigation flue (200) irrigates the surgical field and the suction through ultrasonic blade (100) draws off tissue fragments and excess fluid. In the second mode, instrument (10) is used to transect and seal tissue structures such as blood vessels, biliary ducts, tissue bundles, etc., based on actuation of trigger (94) and clamp arm assembly (70), without suction and fluid. When operating in the first mode, the operator may not wish to clamp any tissue against ultrasonic blade (100) since the operator is addressing tissue that is distally positioned relative to ultrasonic blade (100). Clamp arm assembly (70) may thus be unused during operation of instrument (10) in the first mode of operation. It may therefore be desirable to maintain clamp arm assembly (70) in a stationary state without requiring the operator to consistently manually maintain clamp arm assembly (70) in a stationary state. To that end, handle assembly (50) and clamp arm assembly (70) comprise complementary ratcheting features that selectively maintain the pivotal position of clamp arm assembly (70) relative to handle assembly (50).

Figure 19:
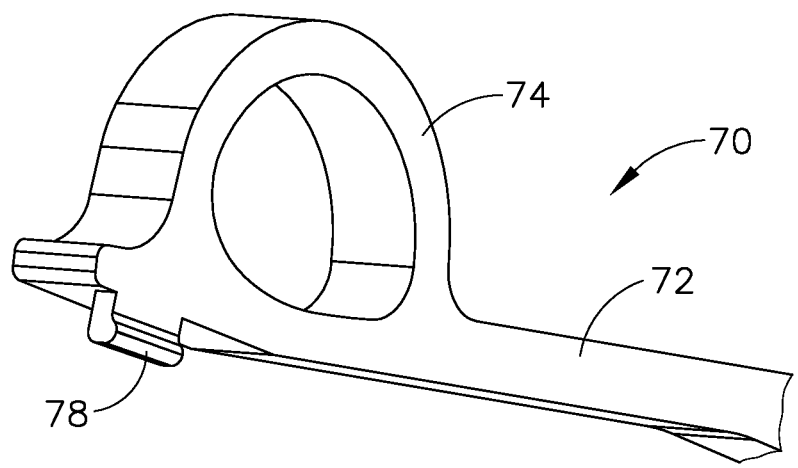
FIG. 19 depicts an enlarged perspective view of a proximal end of a clamp arm of the instrument of FIG. 2.
Figure 20:
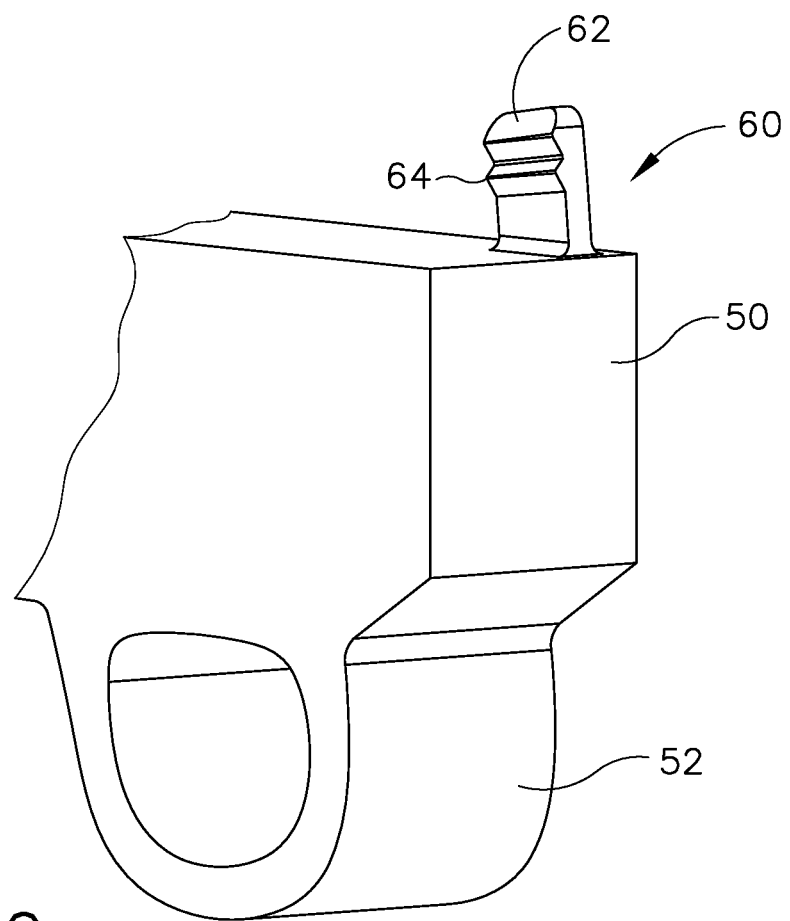
FIG. 20 depicts an enlarged perspective view of a proximal end of the body that is omitted from the depiction of the instrument of FIG. 2.
Figure 21A:
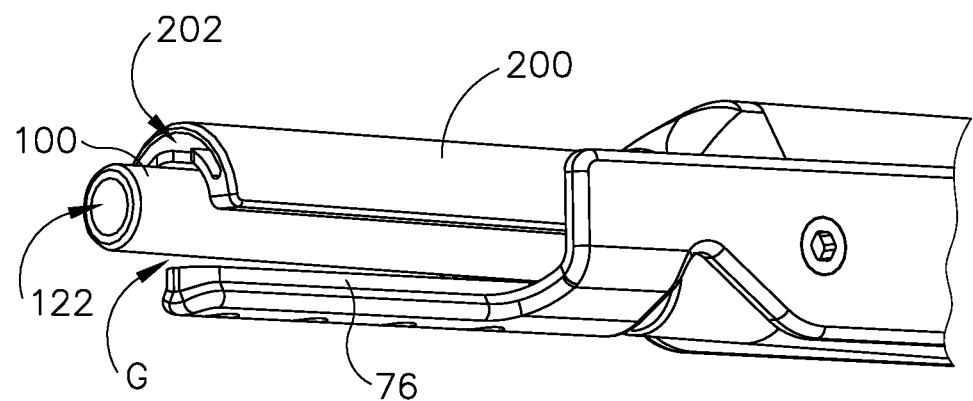
FIG. 21A depicts a perspective view of the end effector of FIG. 3, with the end effector in a parked, partially closed state.
Figure 22A:
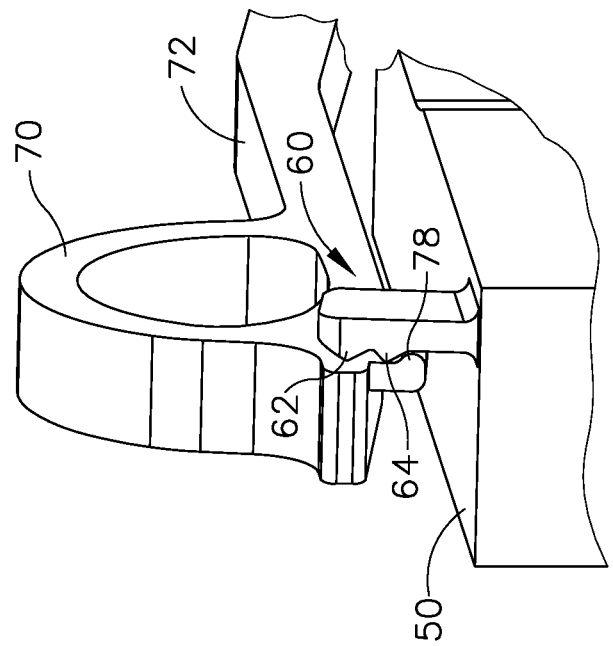
FIG. 22A depicts an enlarged perspective view of a proximal end of a body of the instrument of FIG. 2, with complementary ratcheting features of the clamp arm and body engaged in a parked, partially closed state.
Figure 22B:
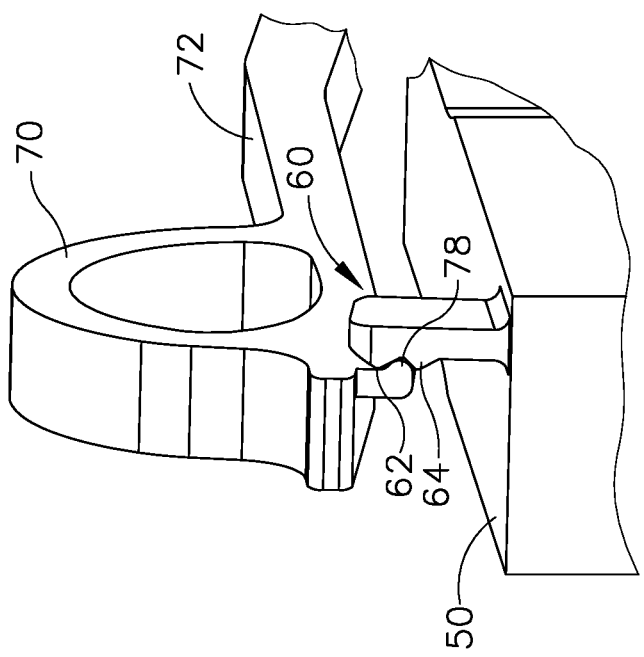
FIG. 22B depicts an enlarged perspective view of a proximal end of a body of the instrument of FIG. 2, with complementary ratcheting features of the clamp arm and body engaged in a closed state.

As best seen in FIGS. 19 and 22A-22B, the proximal end of clamp arm assembly (70) includes a laterally projecting pawl (78). As best seen in FIGS. 20 and 22A-22B, the proximal end of handle assembly (50) includes a ratchet feature (60). Ratchet feature (60) includes a first laterally projecting pawl (62) and a second laterally projecting pawl (64). Pawl (78) is configured to selectively engage pawls (62, 64). In particular, as clamp arm assembly (70) is pivoted toward handle assembly (50), such that clamp pad (76) is pivoted toward ultrasonic blade (100), pawl (78) will eventually engage pawl (62). As the operator continues to pivot clamp arm assembly (70) toward handle assembly (50), pawl (78) may eventually deflect away from pawl (62) and snap into position between pawls (62, 64) as shown in FIG. 22A. In this state, a gap (G) is defined between clamp pad (76) and ultrasonic blade (100) as shown in FIG. 21A. It should be understood that pawls (62, 64, 76) may cooperate to maintain this gap (G) until the operator exerts additional force on clamp arm assembly (70). The operator may wish to maintain the state shown in FIGS. 21A and 22A when operating instrument (10) in the first mode of operation. The gap (G) may prevent clamp pad (76) from encountering unnecessary wear from to ultrasonic vibration of ultrasonic blade (100); and the locking of pawls (62, 64, 76) may prevent the operator from having to otherwise manually maintain the pivotal portion of clamp arm assembly (70).

When the operator wishes to operate instrument (10) in the second mode of operation, the operator may exert sufficient force to disengage pawls (62, 78), thereby opening clamp pad (76) away from ultrasonic blade (100) to enable capture of tissue between clamp pad (76) and ultrasonic blade (100). When the operator has captured tissue between clamp pad (76) and ultrasonic blade (100), the operator may then pivot clamp arm assembly (70) back toward handle assembly (50) to the point where pawl (78) ratchets over pawl (62) and pawl (64) to reach the position shown in FIG. 22B. In this state, clamp pad (76) is in a fully closed position, such that clamp pad (76) would be applying sufficient pressure to the tissue captured between clamp pad (76) and ultrasonic blade (100) in order to properly transect and seal the tissue.

Figure 21B:
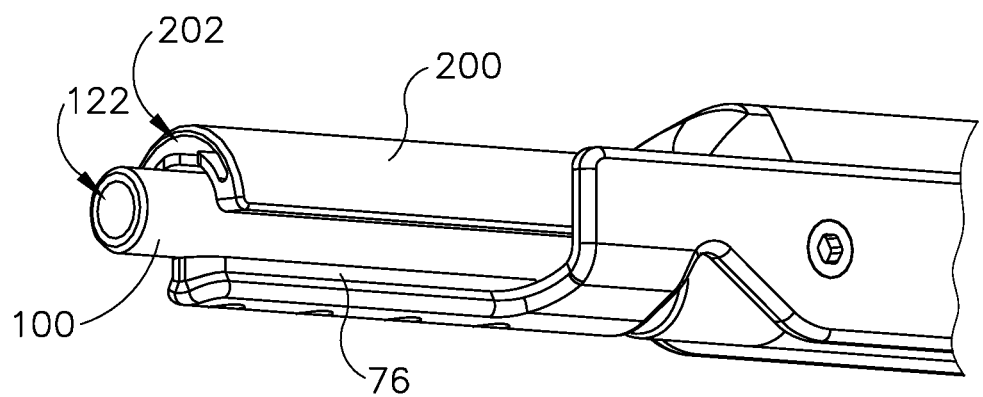
FIG. 21B depicts a perspective view of the end effector of FIG. 3, with the end effector in a closed state.

It should be understood from the foregoing that pawls (62, 64, 76) may cooperate to facilitate operation of instrument (10) in two discrete, selected modes by selectively locking the pivotal position of clamp arm assembly (70) relative to handle assembly (50). It should also be understood that pawls (62, 64, 76) may cooperate to provide audible and/or tactile feedback to indicate whether clamp arm assembly (70) has reached the position shown in FIGS. 21A and 22A or the position shown in FIGS. 21B and 22B. Various other suitable features (e.g., detents) that may be used to provide the same functionality will be apparent to those of ordinary skill in the art in view of the teachings herein.

II. Exemplary Alternative Valve Actuation Assembly

Figure 23:
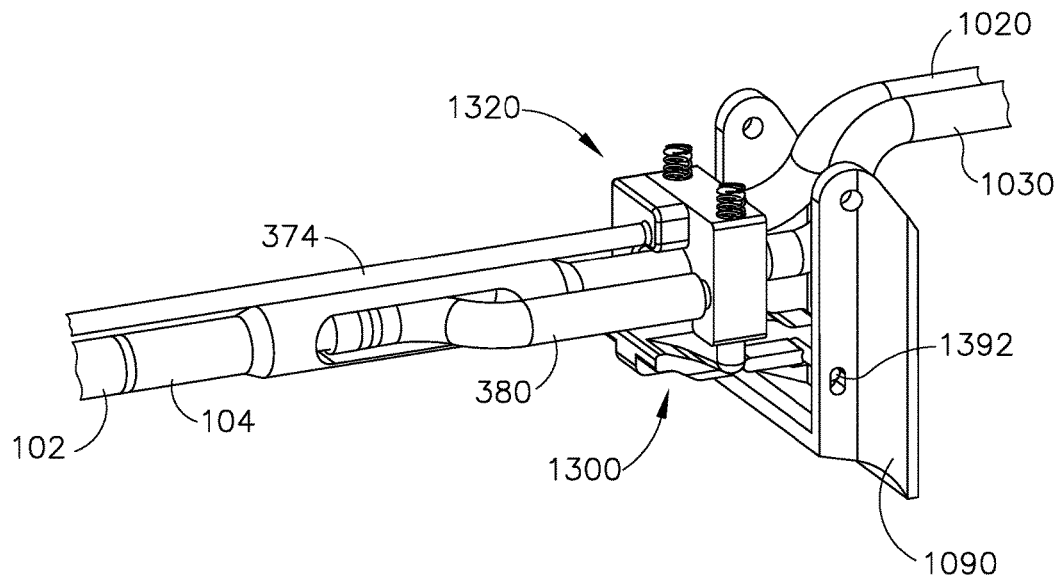
FIG. 23 depicts a perspective view of exemplary alternative suction transmission components and irrigating fluid transmission components that may be incorporated into the instrument of FIG. 2.
Figure 24:
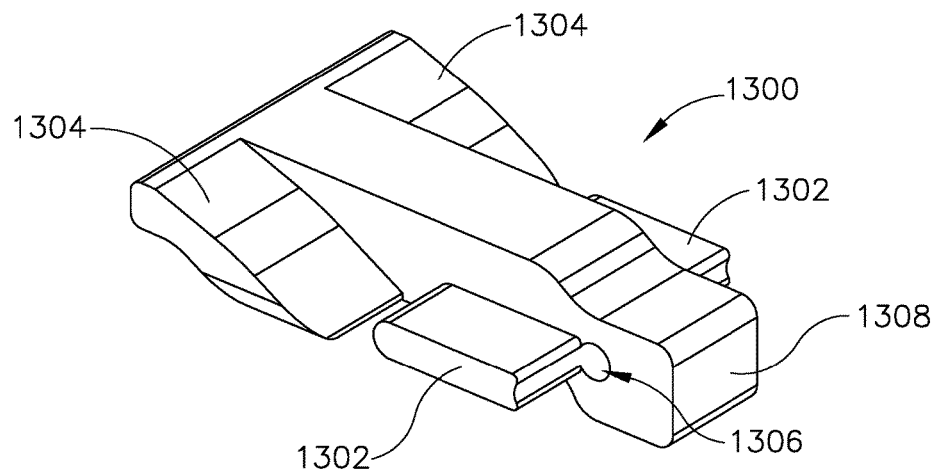
FIG. 24 depicts a perspective view of a cam sled of the components of FIG. 23.
Figure 25:
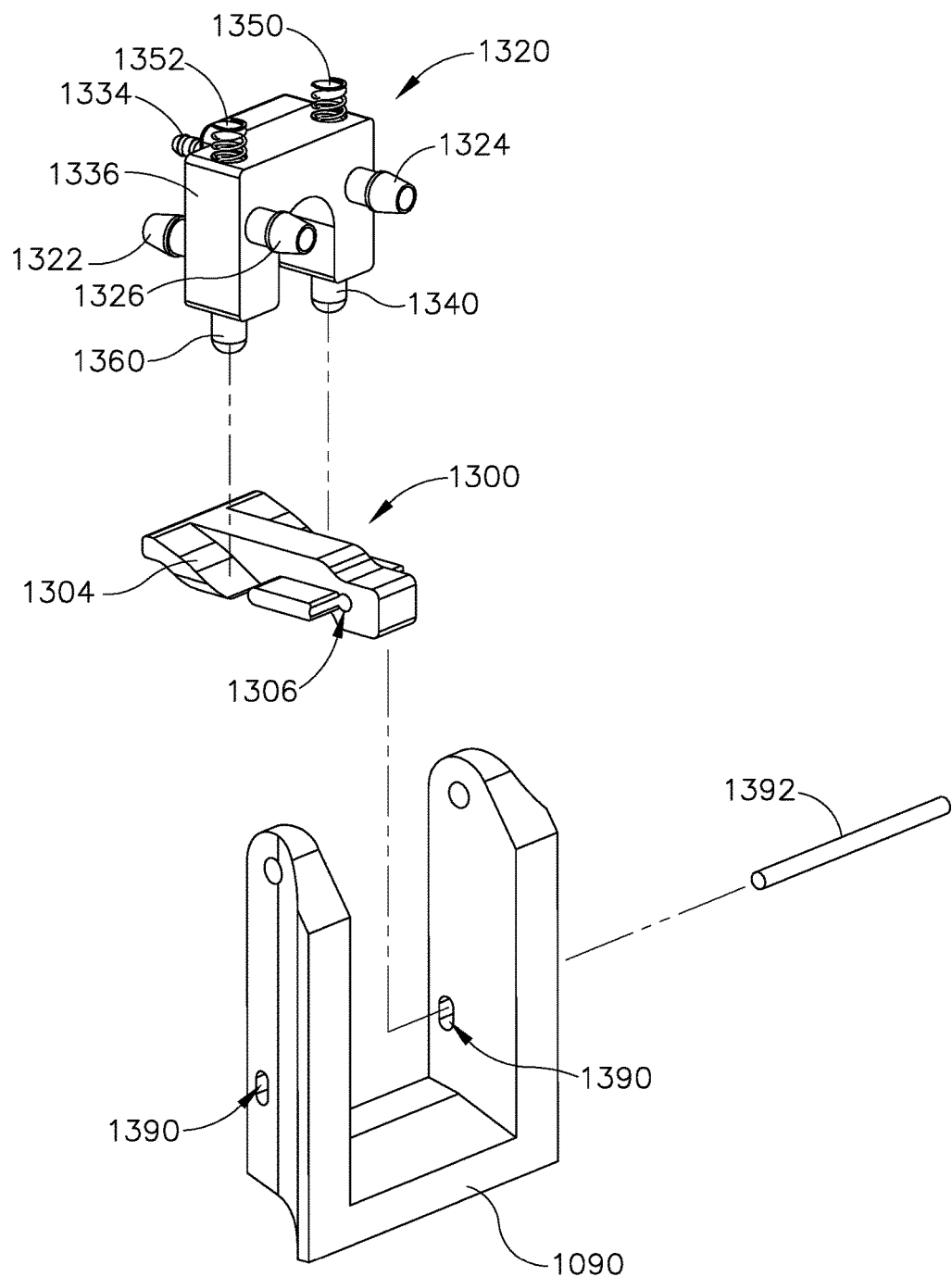
FIG. 25 depicts an exploded view of a valve assembly and actuator of the components of FIG. 23.

FIGS. 23-28B show an exemplary alternative cam sled (1300) and valve assembly (1320) that may be incorporated into instrument (10) in place of cam sled (300) and valve assembly (320). As best seen in FIG. 24, cam sled (1300) of this example includes a pair of outwardly extending flanges (1302) that are slidably received in corresponding channels (not shown) in handle assembly (50) in order to provide support and alignment to cam sled (1300). The proximal end of cam sled (1300) defines a pin opening (1306) and a proximally facing button engagement surface (1308). The distal end of cam sled (1300) defines a pair of cam surfaces (1304). As best seen in FIG. 25, a pin (1392) is disposed in pin opening (1306) of cam sled (1300) and also in a pin opening (1390) of a pivoting trigger (1090), such that pin (1382) couples cam sled (1300) and trigger (1090) together. The relationship between cam sled (1300) and trigger (1090) is just like the relationship between cam sled (300) and trigger (90) described above. Thus, when trigger (1090) is pivoted proximally from the position shown in FIG. 28A to the position shown in FIG. 28B, cam sled (1300) translates proximally.

Figure 26:
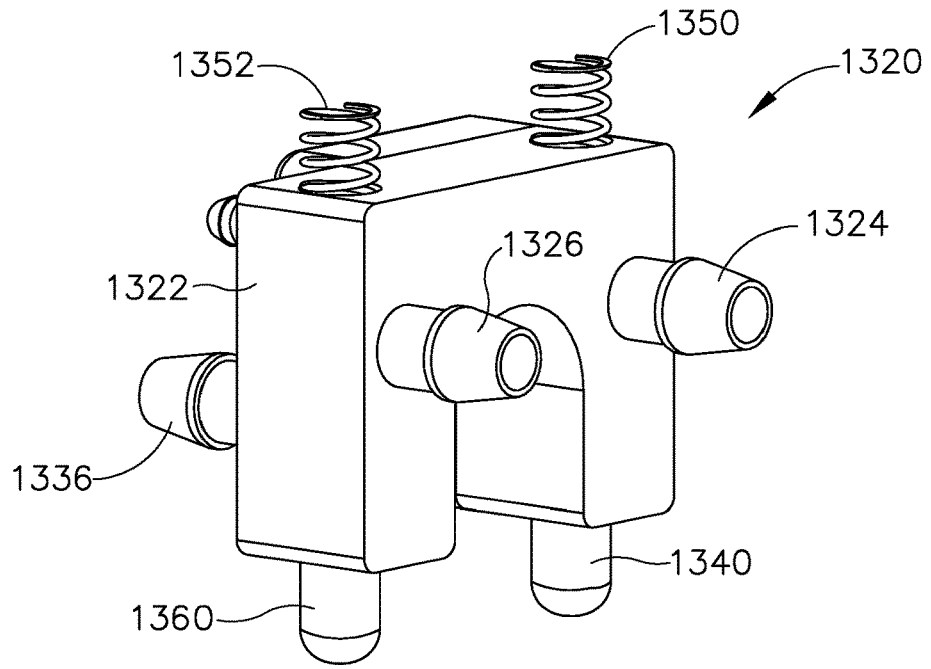
FIG. 26 depicts a perspective view of the valve assembly of FIG. 25.
Figure 27:
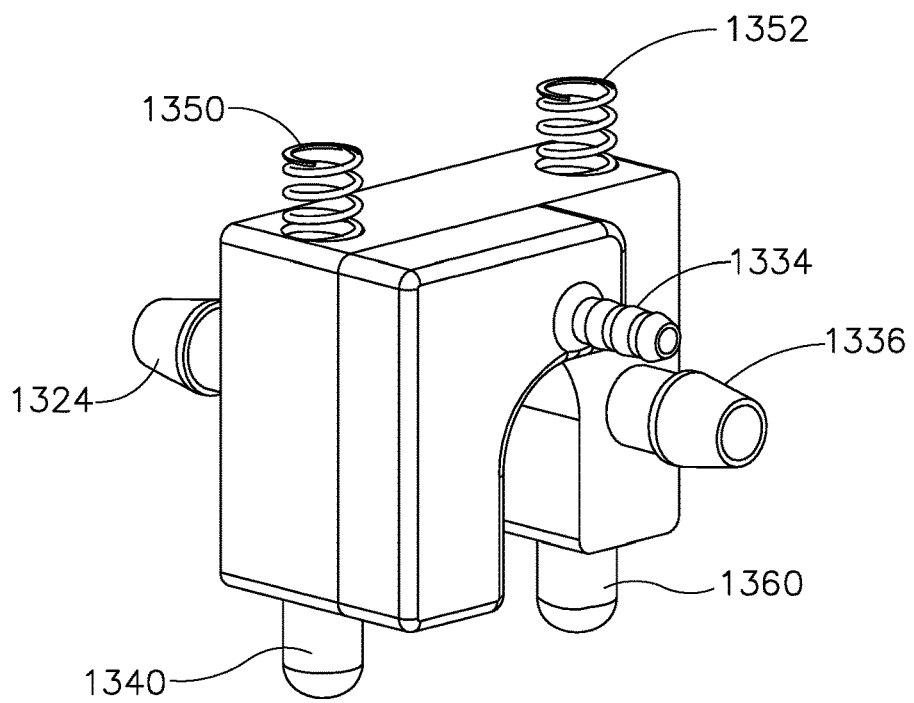
FIG. 27 depicts another perspective view of the valve assembly of FIG. 25.
Figure 28A:
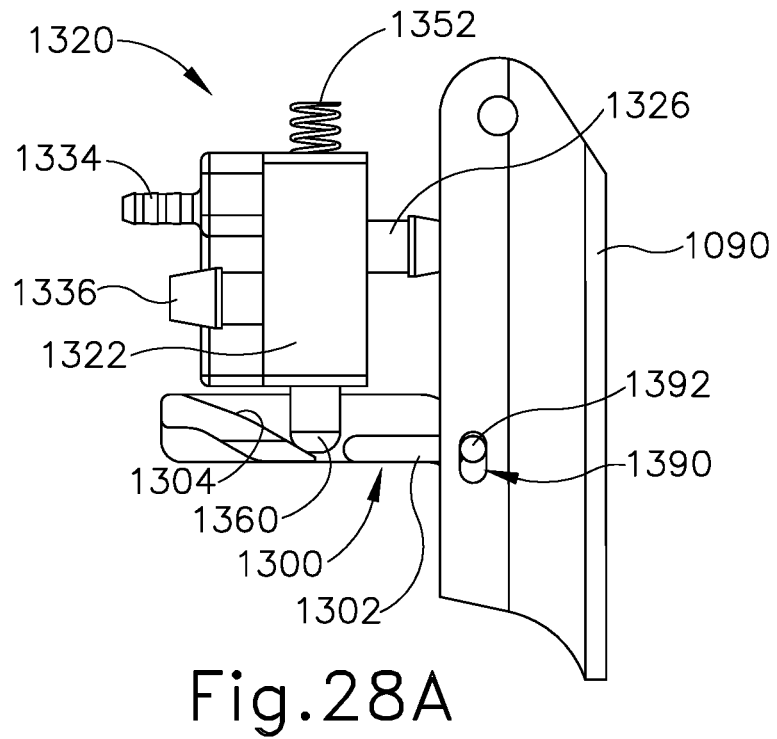
FIG. 28A depicts a side elevational view of actuator components of FIG. 25, with a first trigger in a first pivotal position and the cam sled of FIG. 24 in a distal position.
Figure 28B:
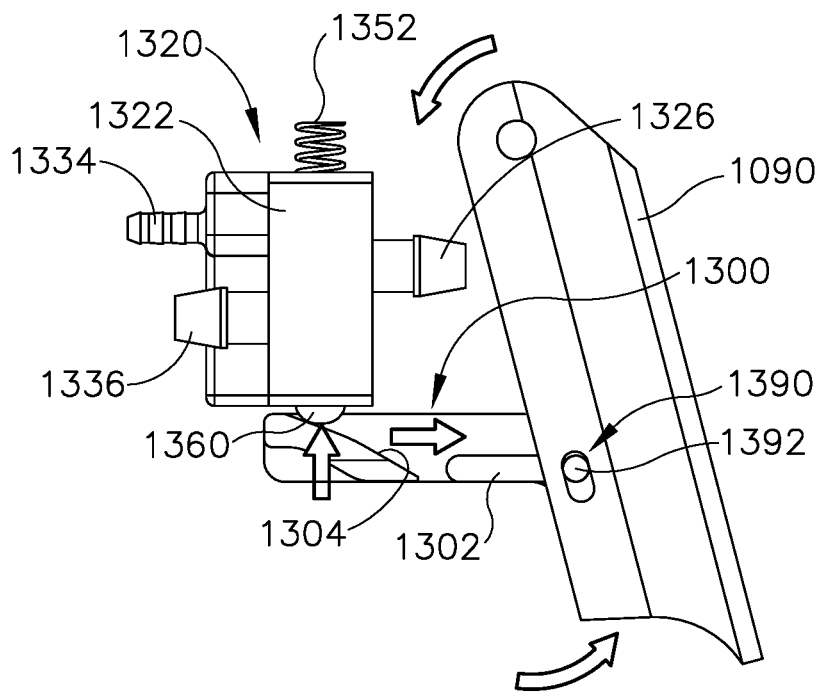
FIG. 28B depicts a side elevational view of actuator components of FIG. 25, with a first trigger in a first pivotal position and the cam sled of FIG. 24 in a proximal position.
Figure 29:
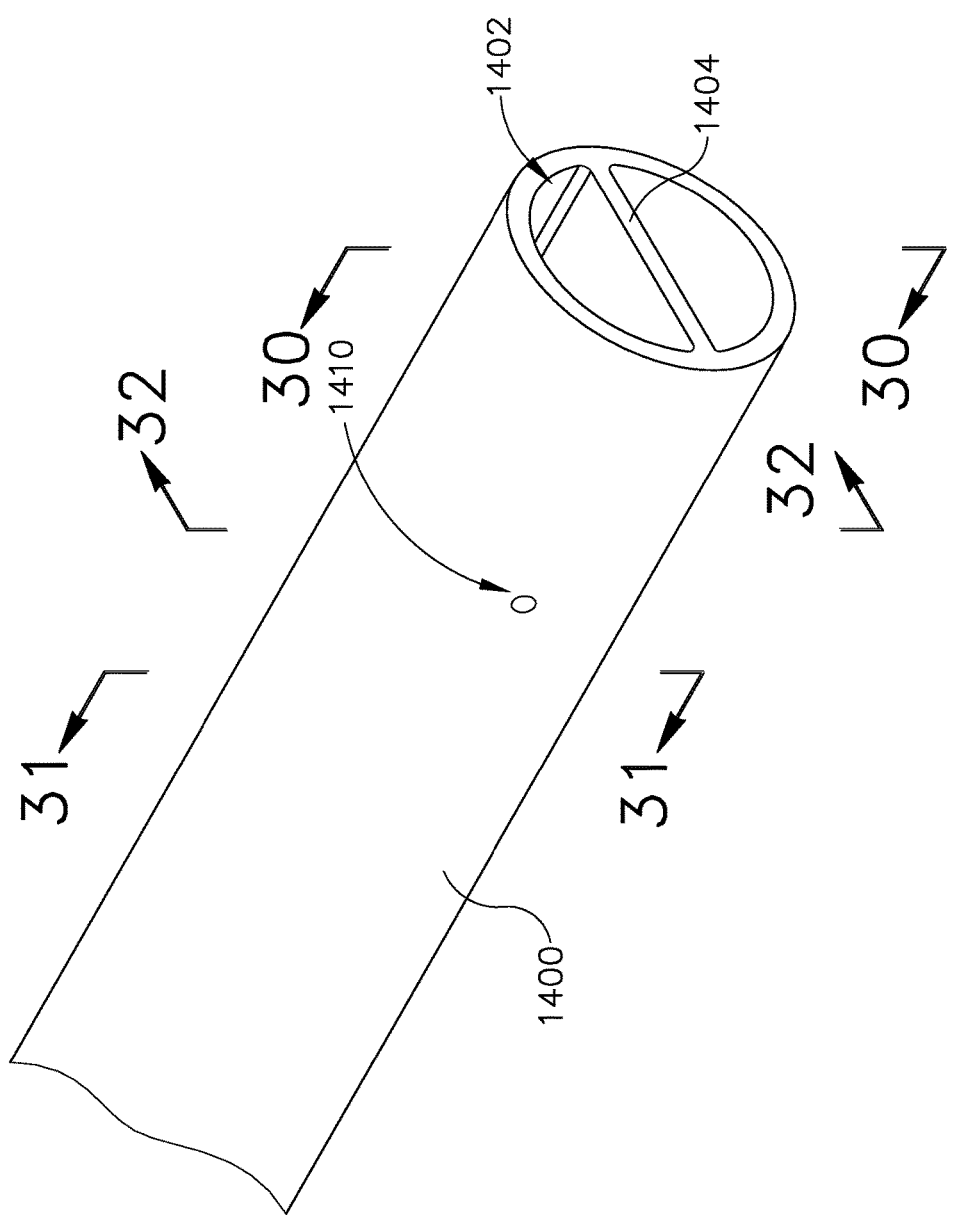
FIG. 29 depicts a partial perspective view of the distal end of an ultrasonic blade that may be incorporated into the instrument of FIG. 2.
Figure 30:
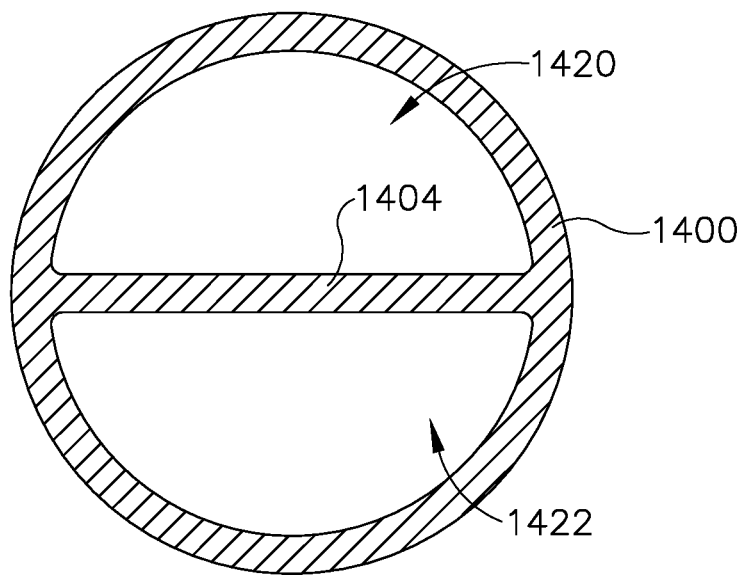
FIG. 30 depicts a cross-sectional view of the blade of FIG. 29, taken along line 30-30 of FIG. 29.

As best seen in FIGS. 26-26, valve assembly (1320) of this example comprises a fluid inlet (1324), a suction inlet (1326), a fluid outlet (1334), and a suction outlet (1336). As shown in FIG. 23, a fluid inlet tube (1030) is coupled with fluid inlet (1324), a suction inlet tube (1020) is coupled with suction inlet (1326), a fluid outlet tube (374) is coupled with fluid outlet (1334), and a suction outlet tube (380) is coupled with suction outlet (1336). Fluid inlet tube (1020) is further coupled with fluid source (30). Suction inlet tube (1030) is further coupled with suction source (40). Fluid outlet tube (374) is further coupled with irrigation flue (200). Suction outlet tube (380) is further coupled with distal waveguide segment (102).

Valve assembly (1320) further comprises a pair of valve actuators (1340, 1360) and corresponding coil springs (1350, 1352). Actuators (1340, 1360) and coil springs (1350, 1352) are configured to operate just like actuators (340, 360) and coil springs (350, 352) described above. Thus, when actuators (1340, 1360) are in the downward position, fluid and suction will not be communicated from tubes (1020, 1030) to tubes (374, 380), respectively. When actuators (1340, 1360) are in the upward position, fluid and suction will be communicated from tubes (1020, 1030) to tubes (374, 380), respectively.

Cam sled (1300) is configured to drive actuators (1340, 1360) to the upward position just like cam sled (300) drives actuators (340, 360) to the upward position as described above. In particular, as trigger (1090) drives cam sled (1300) from the distal position shown in FIG. 28A to the proximal position shown in FIG. 28B, cam surfaces (1304) bear against actuators (1340, 1360) and thereby drive actuators (1340, 1360) upwardly to transition valve assembly (1320) from the closed state to the open state. It should be understood that button engagement surface (1308) will also actuate button (402) when cam sled (1300) is driven proximally to the position shown in FIG. 28B.

III. Exemplary Alternative Ultrasonic Blade Configurations

In the example described above, the distal end of ultrasonic blade (100) defines a single opening having a circular shape. The distal edge of ultrasonic blade (100) is simply flat. It may be desirable to modify the distal end of ultrasonic blade (100) in order to improve the morcellation and/or dissection of tissue when instrument (10) is being used to emulsify tissue. In some instances, this may reduce the risk of tissue fragments clogging the interior lumen of ultrasonic blade (100). In addition, or in the alternative, it may be desirable to modify the distal end of ultrasonic blade (100) in order to improve the action of ultrasonic blade (100) against tissue when the operator sweeps the distal end of ultrasonic blade (100) against tissue in a motion that is transverse to the longitudinal axis of ultrasonic blade (100). It may also be desirable to modify the distal end of ultrasonic blade (100) in order to improve the cutting action of ultrasonic blade (100) through relatively thick and/or relatively dense tissue, such as a Glisson capsule that is typically cut with scalpel. The following examples include several exemplary alternative distal end configurations that may be incorporated into ultrasonic blade (100). The following examples are provided in the context of instrument (10). However, it should be understood the various examples described below may also be incorporated into various other kinds of instruments, including but not limited to instruments that lack a clamp arm assembly (70) or variations thereof.

A. Exemplary Ultrasonic Blade Features to Reduce Lumen Clogging

Figure 31:
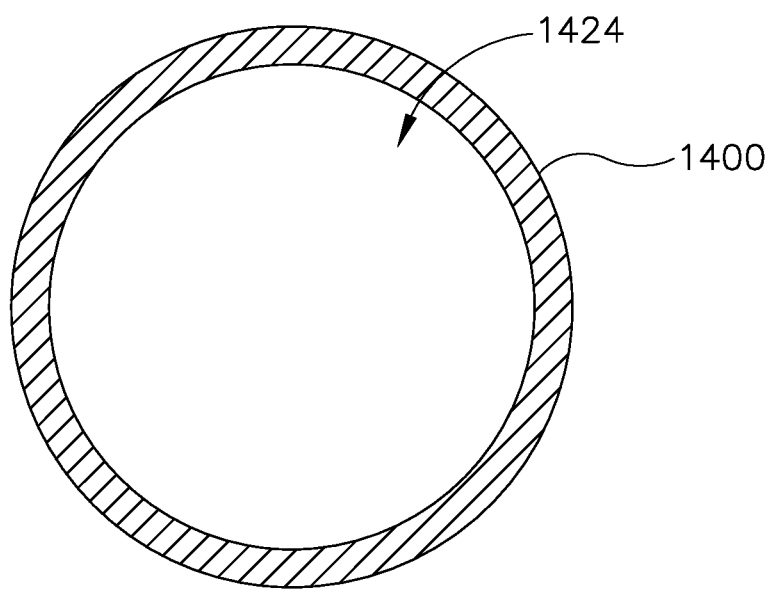
FIG. 31 depicts a cross-sectional view of the blade of FIG. 29, taken along line 31-31 of FIG. 29.
Figure 32:
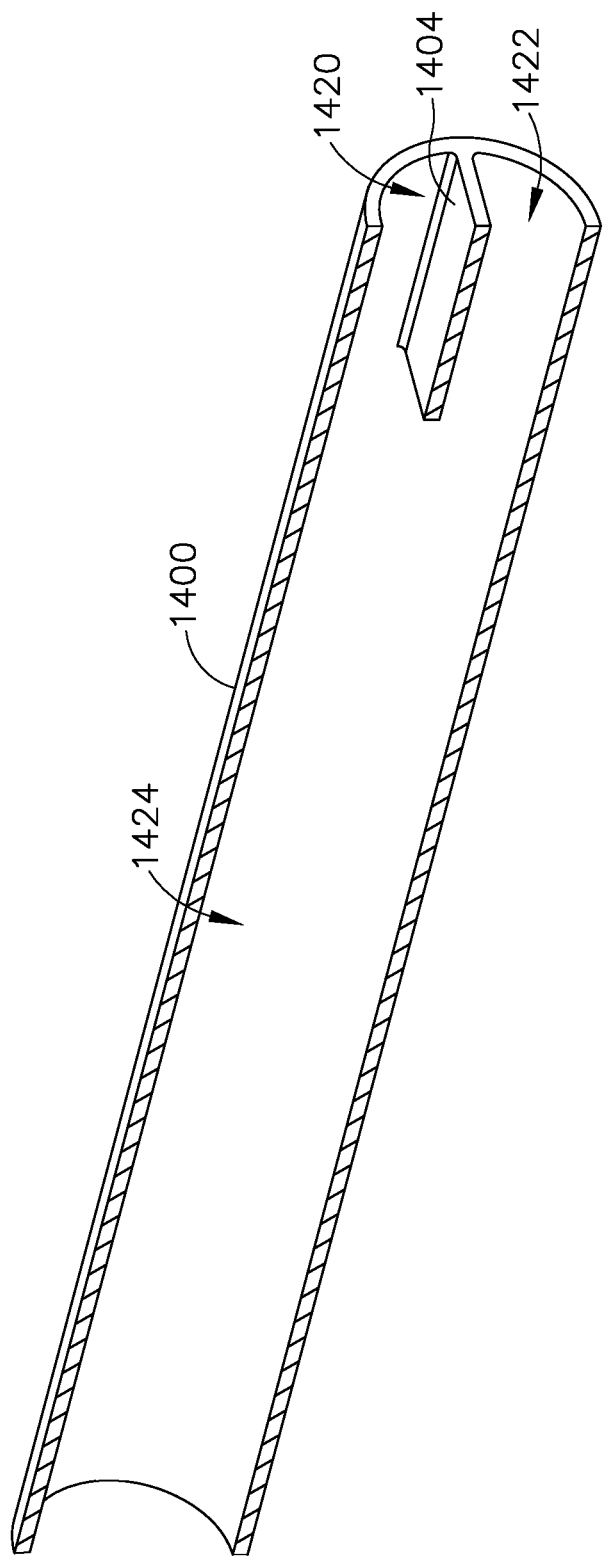
FIG. 32 depicts a cross-sectional view of the blade of FIG. 29, taken along line 32-32 of FIG. 29.

FIGS. 29-32 show an exemplary alternative ultrasonic blade (1400) that may be used in place of ultrasonic blade (100). It should therefore be understood that ultrasonic blade (1400) may be readily incorporated into instrument (10). Ultrasonic blade (1400) of this example has an open distal end with a transversely oriented internal wall (1414). Ultrasonic blade (1400) further includes one or more transverse openings (1410). As best seen in FIG. 32, internal wall (1414) extends longitudinally along only a portion of the length of ultrasonic blade (1400). Thus, in a distal region of ultrasonic blade (1400), internal wall (1414) defines two separate lumens (1420, 1422) (FIG. 30); but the remainder of the length of ultrasonic blade (1400) consists of just a single lumen (1424) (FIG. 31).

When tissue is emulsified by ultrasonic blade (1400), the process may create loose fragments of tissue. These fragments of tissue may be drawn into ultrasonic blade (1400) by suction provided through lumens (1420, 1422, 1424). When relatively large fragments of tissue encounter the distal edge of internal wall (1414), and the suction urges the tissue proximally against the distal edge of internal wall (1414), the resulting forces on the tissue fragments may shear or otherwise fracture the tissue fragments, thereby reducing the size of the fragments. The reduction in tissue fragment size may reduce the risk of the tissue clogging lumen (1424). It should also be understood that transverse opening(s) (1410) will provide a path for transversely drawing fluid (e.g., fluid from irrigation flue (200)) into lumen (1424). This may further promote flushing of tissue from lumen (1424) thereby further reducing the risk of the tissue clogging lumen (1424).

Figure 33:
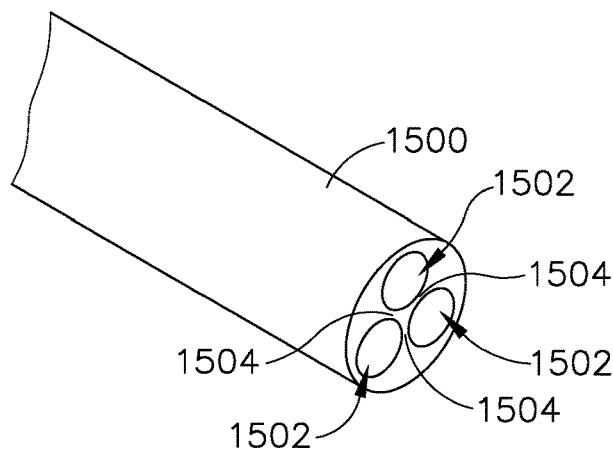
FIG. 33 depicts a partial perspective view of the distal end of another ultrasonic blade that may be incorporated into the instrument of FIG. 2.

FIG. 33 shows another exemplary alternative ultrasonic blade (1500) that may be used in place of ultrasonic blade (100). It should therefore be understood that ultrasonic blade (1500) may be readily incorporated into instrument (10). Ultrasonic blade (1500) of this example has three separate distal passageways (1502) that are separated by walls (1504). In some versions, walls (1504) extend longitudinally for only a portion of the length of ultrasonic blade (1500), such that passageways (1502) proximally merge into a large, single lumen (e.g., similar to lumen (1424)). When relatively large fragments of tissue encounter the distal edge of wall (1504), and the suction urges the tissue proximally against the distal edge of wall (1504), the resulting forces on the tissue fragments may shear or otherwise fracture the tissue fragments, thereby reducing the size of the fragments. The reduction in tissue fragment size may reduce the risk of the tissue clogging ultrasonic blade (1500). In the event that a large fragment of tissue does not shear or otherwise fracture at the distal edge of wall (1504), the large fragment of tissue may simply be brushed away from the distal end of ultrasonic blade (1500).

B. Exemplary Ultrasonic Blade Features to Improve Sweeping Tissue Engagement

Figure 34:
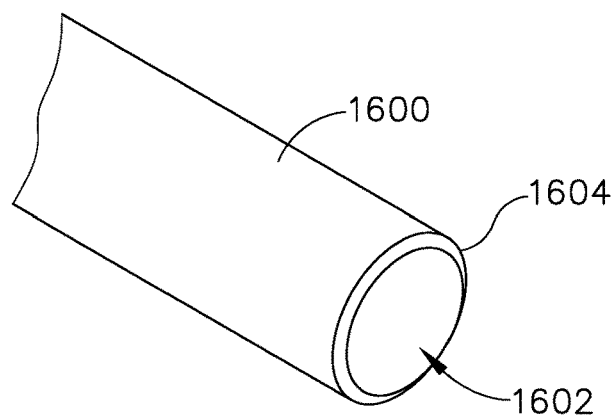
FIG. 34 depicts a partial perspective view of the distal end of another ultrasonic blade that may be incorporated into the instrument of FIG. 2.

FIG. 34 shows another exemplary alternative ultrasonic blade (1600) that may be used in place of ultrasonic blade (100). It should therefore be understood that ultrasonic blade (1600) may be readily incorporated into instrument (10). Ultrasonic blade (1600) of this example has a convexly tapered distal edge (1604) surrounding a distal opening (1602). The configuration of this convexly tapered distal edge (1604) may be sharp, functioning as a lead-in or a chamfer. Ultrasonic blade (1600) may thereby penetrate tissue more easily as ultrasonic blade (1600) is pressed against tissue and swept in a motion that is transverse to the longitudinal axis of ultrasonic blade (1600) (e.g., similar to a brushing motion).

Figure 35:
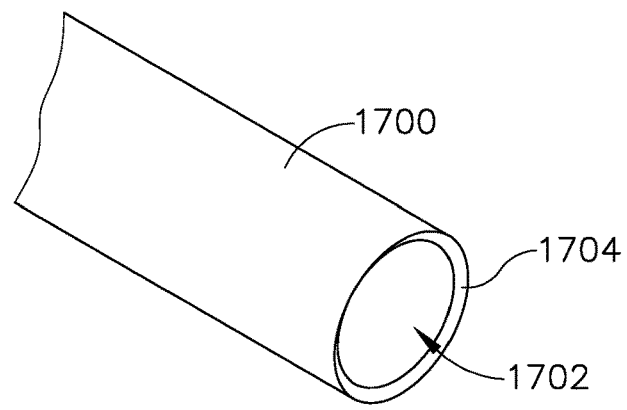
FIG. 35 depicts a partial perspective view of the distal end of another ultrasonic blade that may be incorporated into the instrument of FIG. 2.

FIG. 35 shows another exemplary alternative ultrasonic blade (1700) that may be used in place of ultrasonic blade (100). It should therefore be understood that ultrasonic blade (1700) may be readily incorporated into instrument (10). Ultrasonic blade (1700) of this example has a concavely tapered distal edge (1704) surrounding a distal opening (1702). The configuration of this concavely tapered distal edge (1704) may be sharp, functioning as a lead-in or a chamfer. Ultrasonic blade (1700) may thereby penetrate tissue more easily as ultrasonic blade (1700) is pressed against tissue and swept in a motion that is transverse to the longitudinal axis of ultrasonic blade (1700) (e.g., similar to a brushing motion).

C. Exemplary Ultrasonic Blade Features to Improving Tissue Cutting

Figure 36:
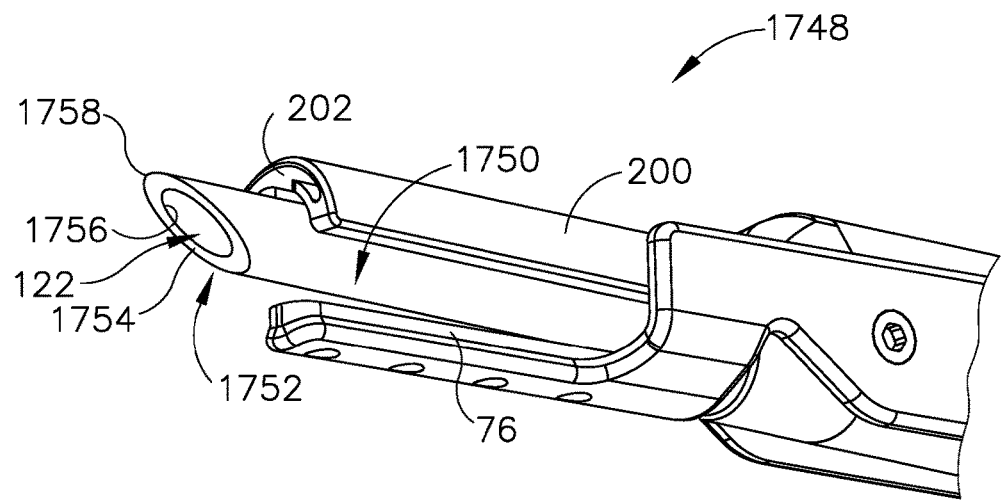
FIG. 36 depicts a perspective view of an exemplary alternative end effector that may be incorporated into the instrument of FIG. 2, with an ultrasonic blade having a distal beveled tip for cutting tissue

FIG. 36 shows an end effector (1748) with another exemplary alternative ultrasonic blade (1750) that includes a distal beveled tip (1752) configured to cut relatively thick and/or dense tissue, as well as emulsify relatively thin and/or less dense tissue as discussed above. End effector (1748) may be readily incorporated into instrument (10) described above. In one example, distal beveled tip (1752) includes a planar face (1754) that surrounds an oblong distal opening (1756). Distal beveled tip (1752) generally extends to a sharpened end (1758) due to beveling of ultrasonic blade (1750). On one hand, orienting distal beveled tip (1752) such that planar face (1754) faces the tissue provides for emulsification as discussed above. On the other hand, reversing the orientation of distal beveled tip (1752) such that planar face (1754) faces away from the tissue effectively directs sharpened end (1758) toward tissue. Sharpened end (1758) is thus ultrasonically driven and configured to concentrate such vibrations with greater precession in order to cut the relatively thick and/or dense tissue.

Figure 37A:
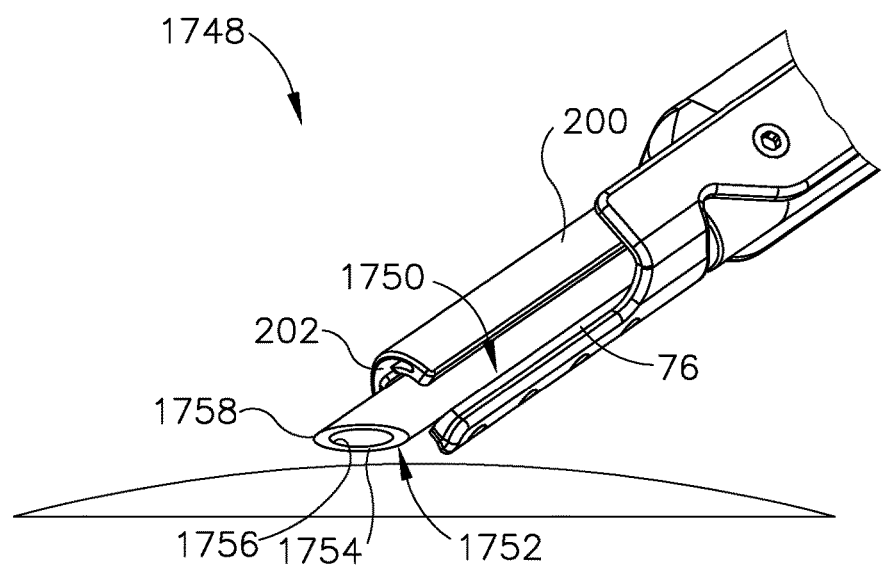
FIG. 37A depicts a perspective view of the ultrasonic blade of FIG. 36 in an emulsification position for emulsifying tissue.
Figure 37B:
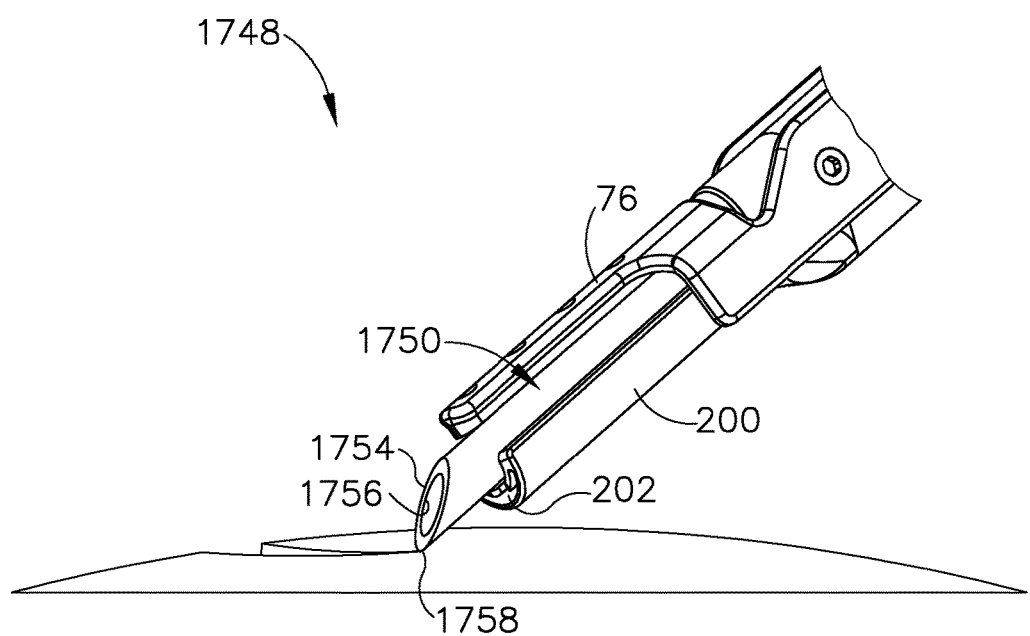
FIG. 37B depicts a perspective view of the ultrasonic blade of FIG. 36 in a cutting position for cutting tissue.
Figure 38:
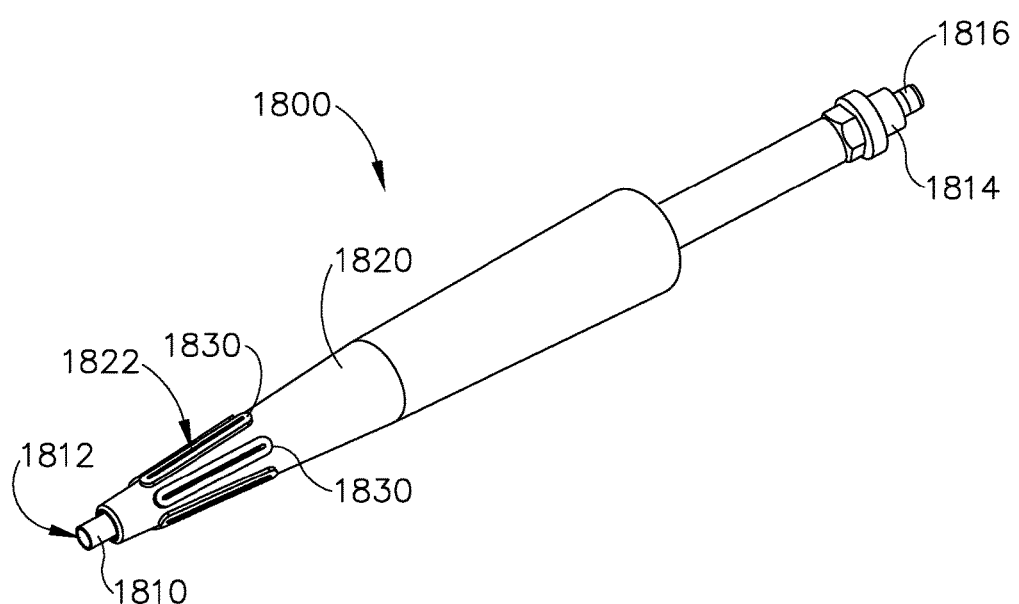
FIG. 38 depicts a perspective view of an exemplary alternative end effector that may be incorporated into an ultrasonic surgical instrument.
Figure 39:
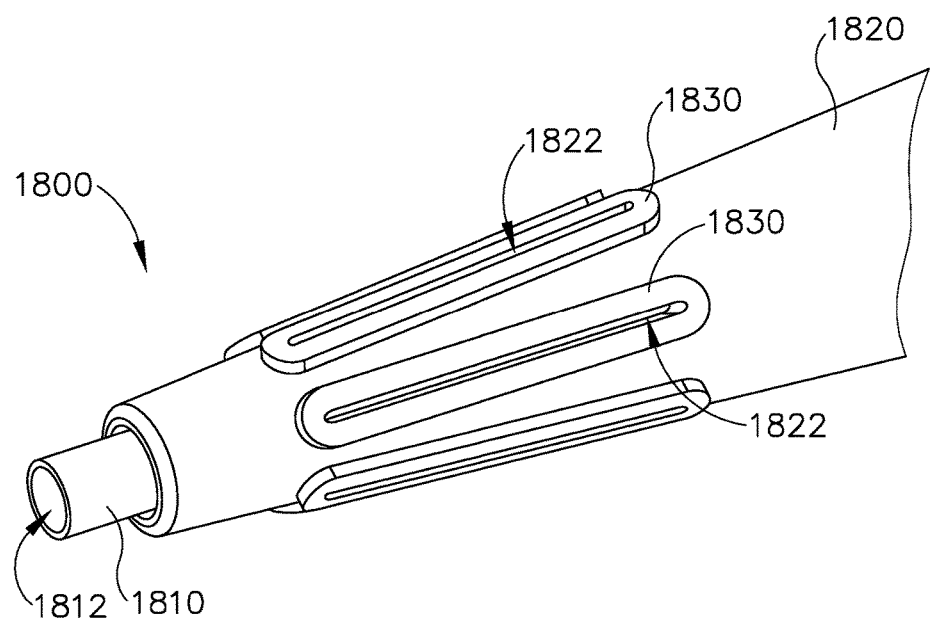
FIG. 39 depicts an enlarged perspective view of the distal end of the end effector of FIG. 38.
Figure 40:
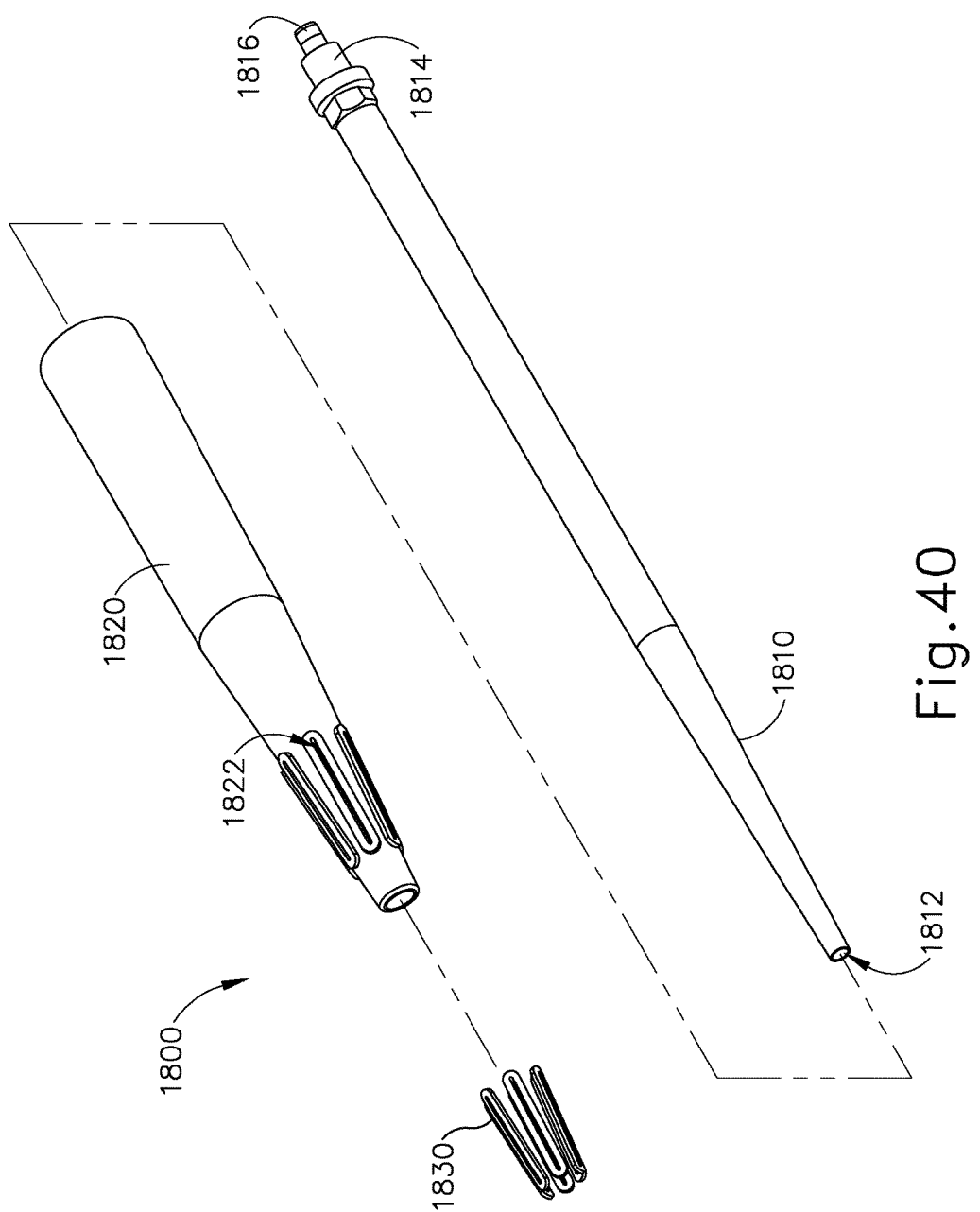
FIG. 40 depicts an exploded view of the end effector of FIG. 38.

In use, the operator emulsifies tissue with the planar face (1754) facing the tissue while sweeping ultrasonic blade (1750) as discussed above and as shown in FIG. 37A. However, a relatively dense outer tissue, such as the Glisson capsule, may be cut in order to dissect the remaining liver parenchyma. To this end, the operator reverses the angular orientation of ultrasonic blade (1750) about the longitudinal axis of blade (1750) such that sharpened end (1758) is directed toward the tissue. While blade (1750) is ultrasonically activated, the operator brings sharpened end (1758) into contact with the Glisson capsule to thereby cut the Glisson capsule as shown in FIG. 37B. In order to return to emulsification, the operator reorients ultrasonic blade (1750) as shown in FIG. 37A, by rotating blade (1750) 180° about the longitudinal axis of blade (1750), for continued sweeping of ultrasonic blade (1750) as desired by the operator.

While exemplary distal beveled tip (1752) includes planar face (1754), oblong distal opening (1756), and sharpened end (1758) as shown in FIGS. 36-37B, it will be appreciated that alternative beveled angles, shapes, and sharpness for an end effector may be similarly configured to cut relatively dense and/or thick tissue in the manner described herein. The invention is thus not intended to be unnecessarily limited to the particular distal beveled tip (1752) shown and described herein. Furthermore, such sharpened end (1758) is described with respect to cutting the Glisson capsule, but it will be further appreciated that sharpened end (1758) may be used for cutting other tissues as desired by the operator during an alternative surgical procedure.

IV. Exemplary Alternative Ultrasonic End Effector with RF Capability

In some instances, it may be desirable to modify instrument (10) to enable instrument (10) to apply radiofrequency (RF) electrical energy to tissue. The RF energy may be useful for sealing small, bleeding vessels. For instance, when instrument (10) is used in the first mode to dissect liver parenchyma to expose relatively large vessels and ducts, this process may sever relatively small vessels in the liver parenchyma, and those vessels may tend to bleed. Since it may be difficult to effectively seal those small bleeding vessels using instrument (10) in the first mode (scalpel-like dissection) or the second mode (transversely oriented transection and sealing through compression) described above, adding one or more electrodes to instrument (10) may enable the easy use of RF energy to effectively seal those small bleeding vessels. Several merely illustrative examples of how one or more RF electrodes may be incorporated into instrument (10) will be described in greater detail below. While the following examples are provided in the context of variations of instrument (10), it should be understood that the following examples may alternatively be incorporated into various other kinds of instruments.

A. Exemplary Ultrasonic End Effector with Annular Array of RF Electrodes

FIGS. 38-41 illustrate an exemplary alternative end effector (1800) that may be incorporated into instrument (10). By way of example only, end effector (1800) may be used in place of ultrasonic blade (100) and clamp arm assembly (70), such that a clamp arm assembly would not be used with end effector (1800) of this example. End effector (1800) of this example comprises an ultrasonic blade (1810) having a lumen (1812), a coupling feature (1814), and a barbed fitting (1816). Ultrasonic blade (1810) may be configured and operable substantially identically to ultrasonic blade (100) described above. Coupling feature (1814) may be coupled with an acoustic waveguide segment as described above. Barbed fitting (1816) may be coupled with a suction tube as described above. Thus, lumen (1812) may be used to apply suction to the surgical field and thereby draw away tissue fragments, etc.

Figure 41:
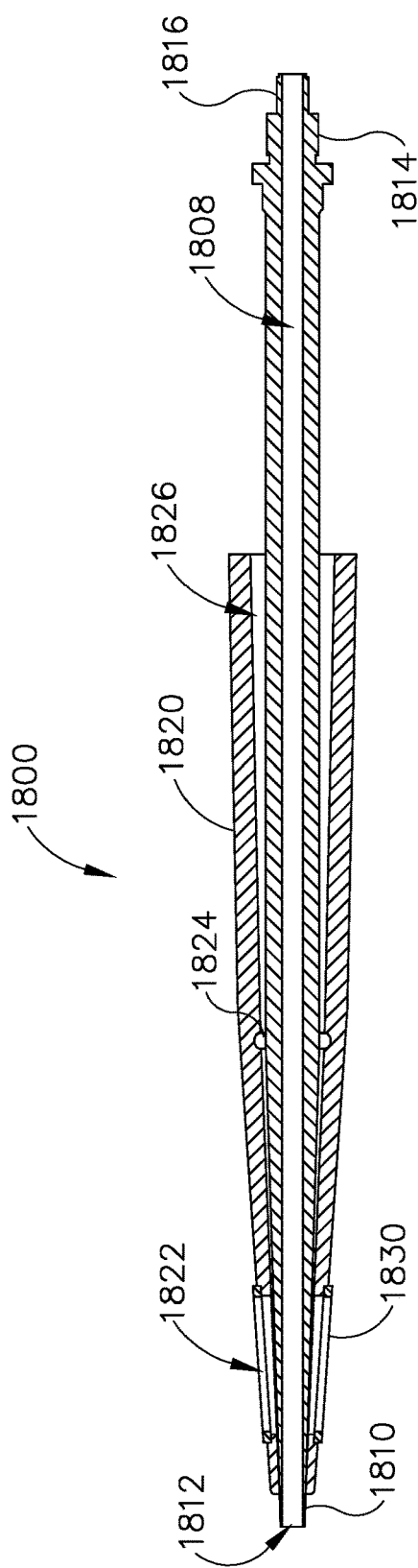
FIG. 41 depicts a cross-sectional side view of the end effector of FIG. 38.

End effector (1800) of this example further comprises a shroud (1820) disposed coaxially about ultrasonic blade (1810). The distal end of shroud (1820) includes a plurality of longitudinally extending slits (1822). Slits (1822) are arranged in an angularly spaced array about the longitudinal axis of shroud (1820). As best seen in FIG. 41, an elastomeric member (1830) is interposed between ultrasonic blade (1810) and shroud (1820) to provide support between ultrasonic blade (1810) and shroud (1820). Elastomeric member (1830) is located at a longitudinal position corresponding to a node associated with ultrasonic vibrations communicated along ultrasonic blade (1810). As also seen in FIG. 41, a space (1826) is defined between ultrasonic blade (1810) and shroud (1820). This space (1826) provides a pathway for the communication of fluid to the distal end of shroud (1820), such that shroud (1820) may be used to provide irrigating fluid to the surgical site like irrigation flue (200) described above. It should be understood that elastomeric member (1830) may defined one or more openings that accommodate the communication of fluid from the proximal portion of space (1826) to the distal portion of space (1826).

End effector (1800) of this example further comprises a plurality of electrodes (1830) disposed about the distal end of shroud (1820). Each electrode (1830) is positioned about a corresponding slit (1822). Each electrode (1830) is in electrical communication with a power source, such that the power source is operable to deliver RF energy to tissue via electrodes (1830). By way of example only electrodes (1830) may be in electrical communication with generator (20) described above. Other suitable power sources that may be used to provide RF energy through electrodes (1830) will be apparent to those of ordinary skill in the art in view of the teachings herein.

In some versions, end effector (1800) provides monopolar RF energy to tissue. For instance, a conventional electrical ground pad may be placed on or under the patient. All electrodes (1830) may be activated, and the ground pad may serve as a return path when electrodes (1830) are activated. In some other versions, end effector (1800) provides bipolar RF energy to tissue. For instance, ultrasonic blade (1810) may serve as a return path when electrodes (1830) are activated. As another merely illustrative example, electrodes (1830) along the angular array may alternate between serving as active electrodes and return electrodes (1830). For instance, a first electrode (1830) may be designated as an active electrode, with the next electrode (1830) serving as a return electrode, followed by the next electrode (1830) serving as an active electrode, and so on. Other suitable ways in which end effector (1800) may provide monopolar RF energy or bipolar RF energy to tissue will be apparent to those of ordinary skill in the art in view of the teachings herein.

It should be understood that fluid may be delivered to the surgical field via slits (1822) while electrodes (1830) are being activated. In addition to flushing debris from the surgical field, providing a cooling effect, and/or providing other effects, the fluid may be electrically conductive and thus promote communication of the RF energy to tissue. When electrodes (1830) are activated with RF energy, the operator may press one or more electrodes (1830) against the tissue and sweep end effector (1800) along the tissue (e.g., along a path that is transverse to the longitudinal axis of end effector (1800)) to seal bleeders in the tissue.

B. Exemplary Irrigation Flue with RF Electrode

Figure 42:
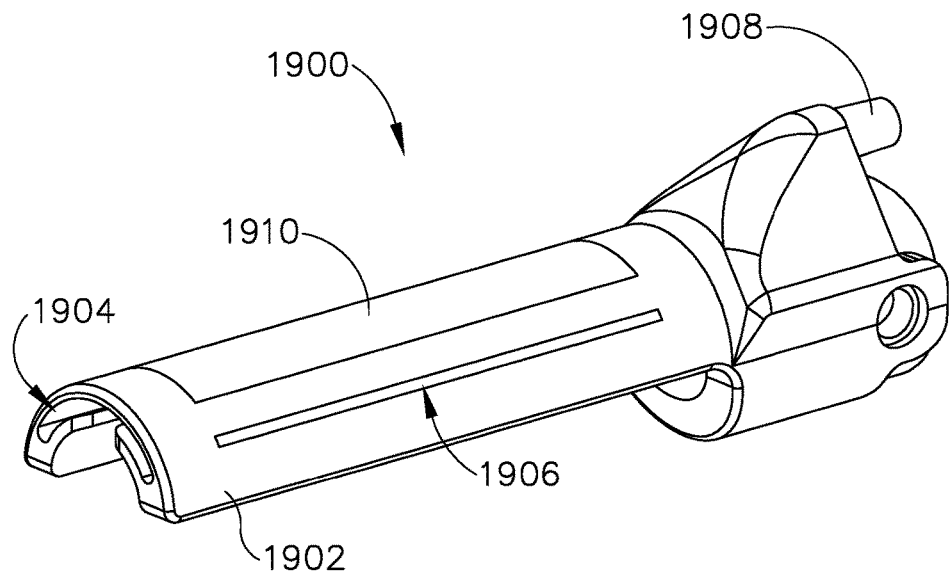
FIG. 42 depicts a perspective view of an exemplary alternative irrigation flue that may be incorporated into the instrument of FIG. 2.
Figure 43:
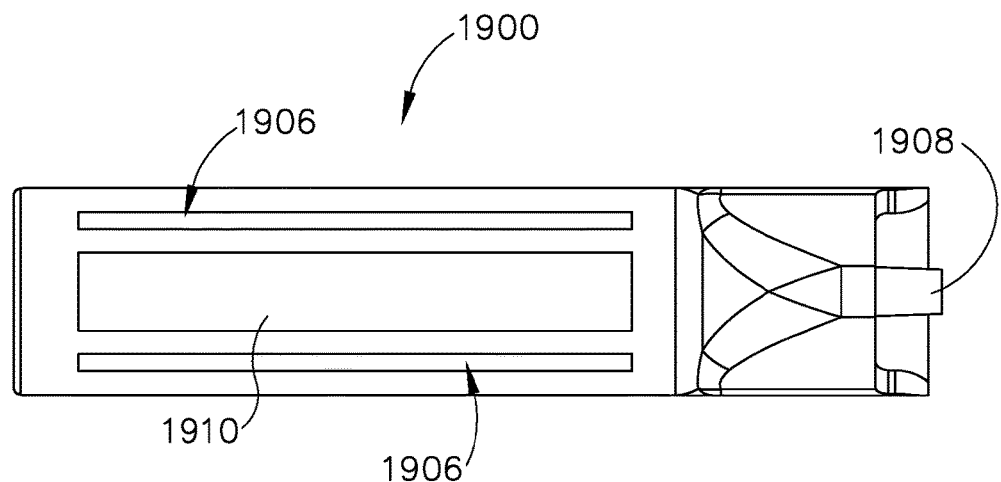
FIG. 43 depicts a top plan view of the irrigation flue of FIG. 42.

FIGS. 42-43 depict another exemplary way in which RF capabilities may be incorporated into instrument (10). In particular, FIGS. 42-43 show an exemplary alternative irrigation flue (1900) that may be used in place of irrigation flue (200). Irrigation flue (1900) of this example includes a body (1902) with an open distal end (1904); a pair of longitudinally extending, laterally presented slits (1906); a fluid port (1908); and a longitudinally extending electrode (1910) on the outer surface of body (1902). Slits (1906) flank electrode (1910) and are in fluid communication with the same internal lumen of body (1902) as open distal end (1904) and fluid port (1908). Thus, fluid communicated to fluid port (1908) (e.g., via fluid tube (374)) will be expelled through open distal end (1904) and through slits (1906).

Electrode (1910) is in electrical communication with a power source, such that the power source is operable to deliver RF energy to tissue via electrode (1910). By way of example only electrode (1910) may be in electrical communication with generator (20) described above. Other suitable power sources that may be used to provide RF energy through electrode (1910) will be apparent to those of ordinary skill in the art in view of the teachings herein.

In some versions, irrigation flue (1900) provides monopolar RF energy to tissue. For instance, a conventional electrical ground pad may be placed on or under the patient. Electrode (1910) may be activated, and the ground pad may serve as a return path when electrode (1910) is activated. In some other versions, irrigation flue (1900) provides bipolar RF energy to tissue. For instance, ultrasonic blade (100) may serve as a return path when electrode (1910) is activated. As another merely illustrative example, irrigation flue (1900) may include two or more electrodes (1910), such that the two or more electrodes (1910) may cooperate to provide bipolar RF energy. Other suitable ways in which irrigation flue (1900) may provide monopolar RF energy or bipolar RF energy to tissue will be apparent to those of ordinary skill in the art in view of the teachings herein.

It should be understood that fluid may be delivered to the surgical field via slits open distal end (1904) and slits (1906) while electrode (1910) is being activated. In addition to flushing debris from the surgical field, providing a cooling effect, and/or providing other effects, the fluid may be electrically conductive and thus promote communication of the RF energy to tissue. When electrode (1910) is activated with RF energy, the operator may press electrode (1910) against the tissue and sweep irrigation flue (1900) along the tissue (e.g., along a path that is transverse to the longitudinal axis of ultrasonic blade (100)) to seal bleeders in the tissue.

C. Exemplary Ultrasonic End Effector with Clamp Arm Electrode

FIGS. 44-47 depict additional exemplary end effectors (2000, 2020, 2040) that include various respective electrodes (2002, 2022, 2042) configured to provide RF energy to tissue for sealing small, bleeding vessels as discussed above. More particularly, electrodes (2002, 2022, 2042) are each positioned on respective clamp arm assemblies (2004, 2024, 2044) such that such sealing may conveniently be performed with electrodes (2002, 2022, 2042) while also compressing tissue against ultrasonic blade (100). It should be understood that the end effectors (2000, 2020, 2040) described below may be readily incorporated into instrument (10) described above.

Figure 44:
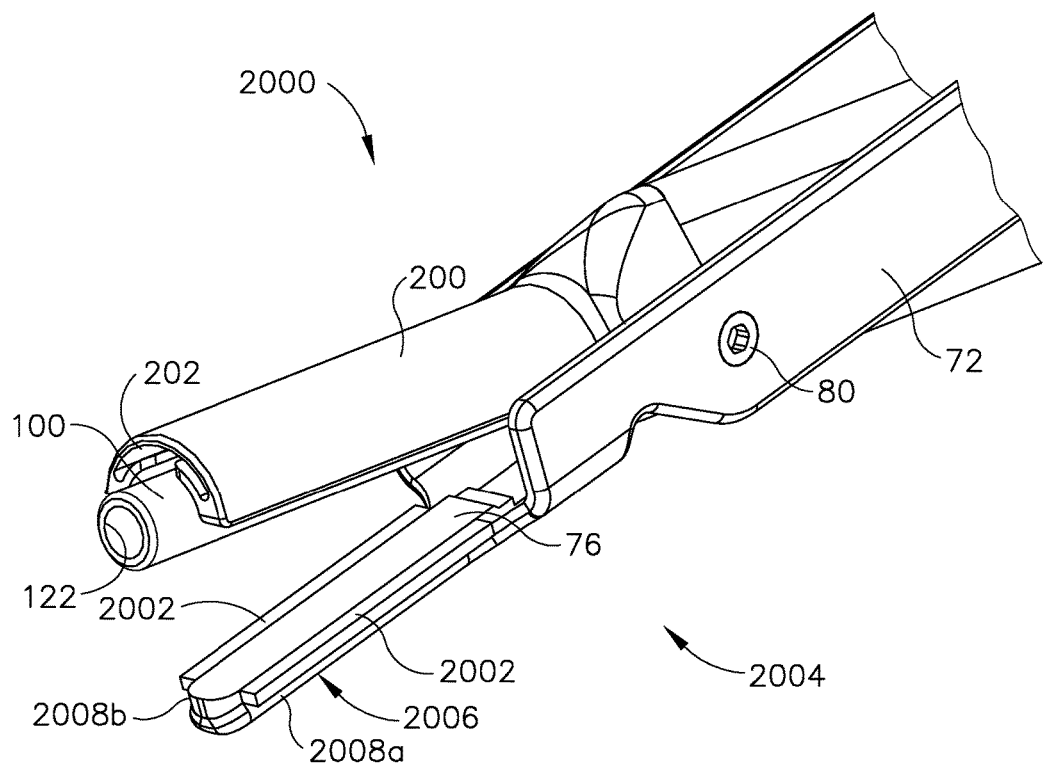
FIG. 44 depicts a perspective view of an exemplary alternative end effector that may be incorporated into the instrument of FIG. 2, with a clamp arm electrode.
Figure 45:
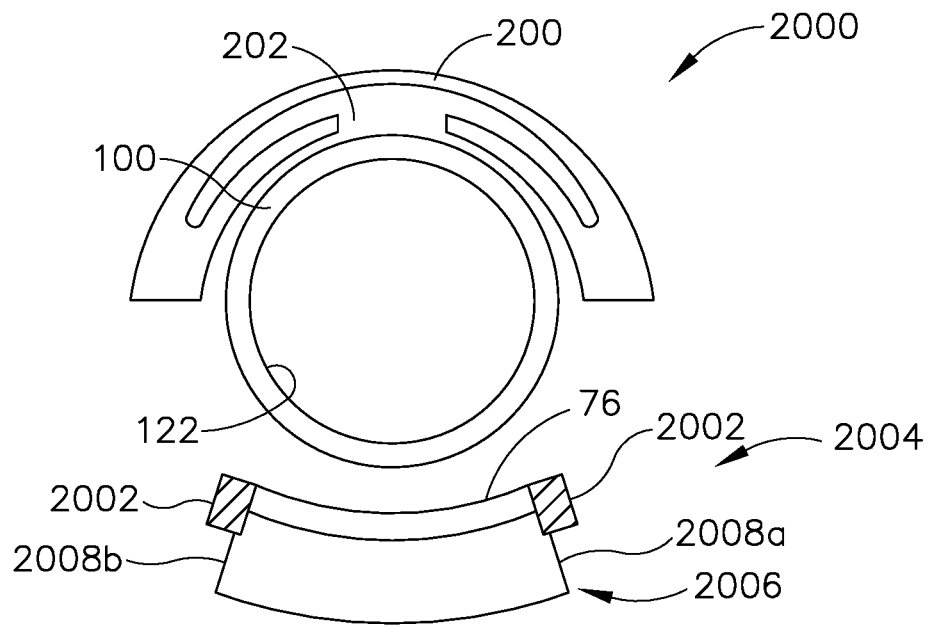
FIG. 45 depicts a distal end elevation view of the end effector of FIG. 44.

As shown in FIGS. 44-45, end effector (2000) includes a clamp jaw (2006) having clamp pad (76) and a pair of opposing lateral sides (2008a, 2008b). Clamp pad (76) generally extends laterally between sides (2008a, 2008b) and longitudinally along clamp jaw (2006). Elongated electrodes (2002) are positioned to extend longitudinally along each respective side (2008a, 2008b) and are in electrical communication with a power source (e.g., generator (20), described above), such that the power source is operable to deliver RF energy to tissue via electrodes (2002). More particularly, elongated electrodes (2002) extend continuously along sides (2008a, 2008b) along a majority of clamp jaw (2006) to provide a relatively elongated and continuous sealing functionality. By way of example only, electrodes (2002) may be in electrical communication with generator (20) described above. Other suitable power sources that may be used to provide RF energy through electrode (2002) will be apparent to those of ordinary skill in the art in view of the teachings herein.

Exemplary electrodes (2002) provide RF energy to tissue to define an RF powered electrode with at least one other component being electrically grounded to provide a return path for the RF energy. In the present example, electrodes (2002) provide bipolar RF energy to tissue. Ultrasonic blade (100) is electrically grounded to define a grounded electrode configured to cooperate with electrodes (2002) to provide RF energy to tissue engaged by electrodes (2002) and blade (100). Thus, spanning RF electrode (2002) and ultrasonic blade (100) with tissue effectively completes an electrical connection therebetween and directs RF energy through the tissue for sealing the tissue.

Electrodes (2002) are more particularly sized in positioned such that electrodes effectively compress against ultrasonic blade (100) when clamp jaw (2006) closes to compress tissue therebetween. However, it will be appreciated that electrodes (2002) may be alternatively positioned so as to remain separated when the clamp jaw (2006) closes in order to provide the return path only with tissue extending therebetween. Furthermore, in still other versions of end effector (2000), one or more of electrodes (2002) may provide monopolar RF energy to tissue. For instance, a conventional electrical ground pad may be placed on or under the patient. Electrodes (2002) may be activated, and the ground pad may serve as the return path when electrode (2002) is activated.

Figure 46:
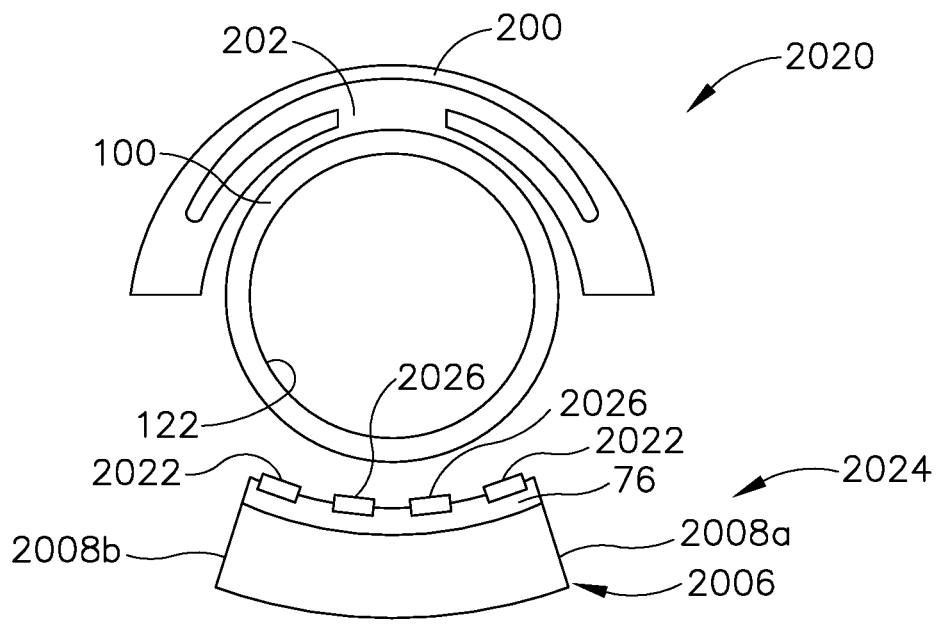
FIG. 46 depicts a distal end elevation view of another exemplary alternative end effector that may be incorporated into the instrument of FIG. 2, with a clamp arm electrode.

It will be appreciated that electrodes, powered and/or ground, may be alternatively shaped and positioned so as to cooperate with each other and contact tissue for sealing tissue. By way of example, FIG. 46 shows another exemplary end effector (2020) with clamp arm assembly (2024) having powered, elongated RF electrodes (2022) extending longitudinally along clamp jaw (2006) similar to electrodes (2002) (see FIG. 44). However, rather than extend along sides (2008a, 2008b), elongated electrodes (2022) extend along clamp pad (76) and may be raised from clamp pad (76) as shown in FIG. 46 and/or flush with an upper surface of clamp pad (76). More particularly, each elongated electrode (2022) is positioned adjacent to one of sides (2008a, 2008b), respectively, and is configured to face ultrasonic blade (100) when clamp jaw (2006) is closed thereagainst. End effector (2020) may include one or more stop features that prevent electrodes (2022) from contacting ultrasonic blade (100) when end effector (2020) is in a fully closed configuration. Such stop features may thus prevent a short circuit from forming between electrodes (2022) and blade (100).

Clamp arm assembly (2024) further includes a pair of elongated ground electrodes (2026) also extending longitudinally along clamp jaw (2006). The pair of elongated ground electrodes (2026) are positioned laterally between and offset from elongated RF electrodes (2022). Like RF electrodes (2022), ground electrodes (2026) extend along clamp pad (76) and may be raised from clamp pad (76) as shown in FIG. 46 and/or flush with the upper surface of clamp pad (76) for compressing tissue against ultrasonic blade (100). Thereby, in use, tissue extends between cooperating RF and ground electrodes (2022, 2026) for directing RF energy therethrough.

Figure 47:
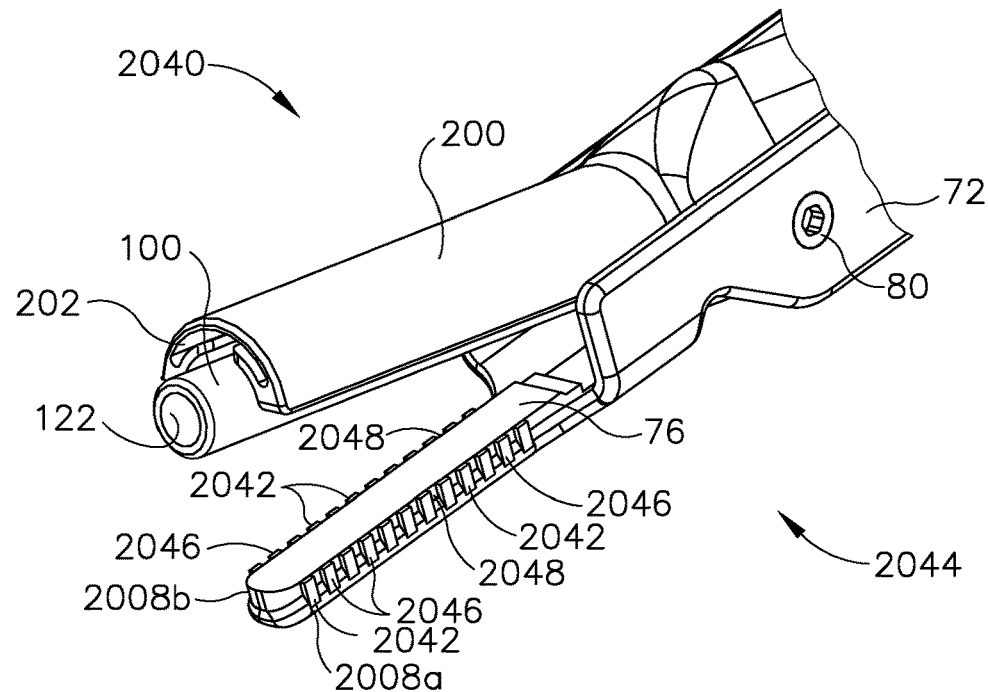
FIG. 47 depicts a perspective view of another exemplary alternative end effector that may be incorporated into the instrument of FIG. 2, with a clamp arm electrode.

In still another example, end effector (2040) shown in FIG. 47 has clamp arm assembly (2044) with an alternating row of RF and ground electrodes (2042, 2046) on each side (2008a, 2008b). An insulator, such as a gap (2048) is positioned between each respective RF and ground electrode (2042, 2046), and inhibits the flow of RF energy unless tissue extends across gap (2048) to seal the tissue. Each RF and ground electrode (2042, 2046) is also configured to compress against ultrasonic blade (100) when clamp jaw (2006) is closed. However, it will be appreciated that that RF and ground electrodes (2042, 2046) may be alternatively positioned so as not to engage ultrasonic blade (100).

In use, the operator manipulates end effector (2000) to provide emulsification as discussed above. In the event that there is bleeding at the emulsified tissue, the operator may "touch up" the bleeding tissue (i.e., stop the bleeding) by contacting the tissue across RF electrodes (2002, 2042, 2046) and grounded ultrasonic blade (100) as discussed briefly above in FIGS. 44-45. More particularly, the operator may simply bring one or more sides (2008a, 2008b) with RF electrode (2002) and grounded ultrasonic blade (100) to tissue for sealing the tissue without changing hand positions from the emulsification process. RF and ground electrodes (2042, 2046) shown in FIG. 47 may be similarly used.

In addition, the operator may seal tissue between RF electrode (2002) and grounded ultrasonic blade (100) while simultaneously compressing tissue between clamp pad (76) and ultrasonic blade (100) as shown with respect to end effectors (2000, 2020) in FIGS. 44-47. The operator thus simultaneously compresses the tissue while sealing spotty bleeding to more effectively and efficiently perform the surgical procedure. However, it will be appreciated that the operator may use such RF electrodes (2002, 2022, 2042) for sealing tissue at any time during the surgical procedure and the invention is not intended to be unnecessarily limited to requiring simultaneous tissue compression against ultrasonic blade (100).

D. Exemplary Ultrasonic End Effector with Irrigation Electrode

Figure 48:
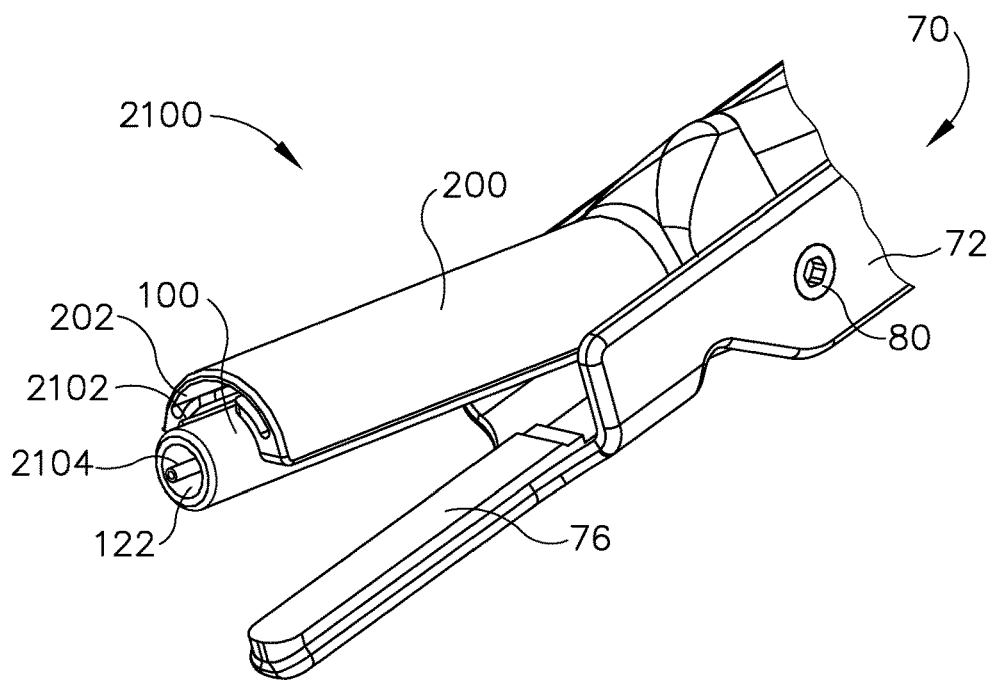
FIG. 48 depicts a perspective view of another exemplary alternative end effector that may be incorporated into the instrument of FIG. 2, with an irrigation flue electrode.
Figure 49:
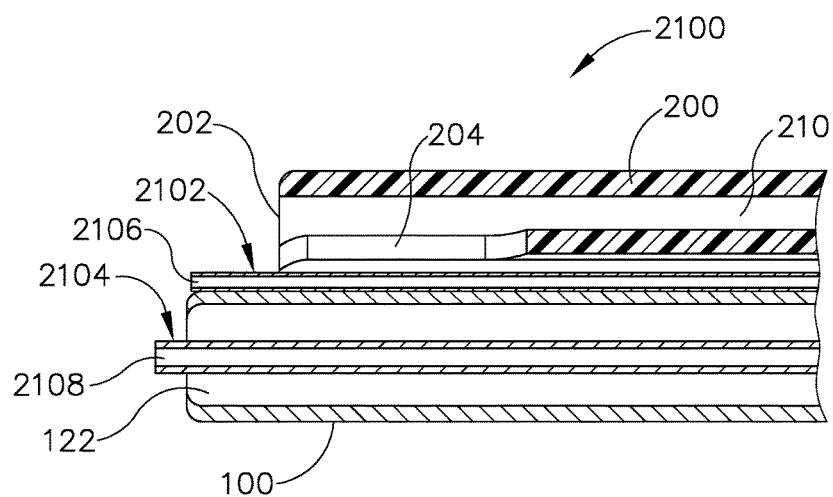
FIG. 49 depicts an enlarged cross-sectional side view of the end effector of FIG. 48, taken along a centerline thereof.
Figure 50:
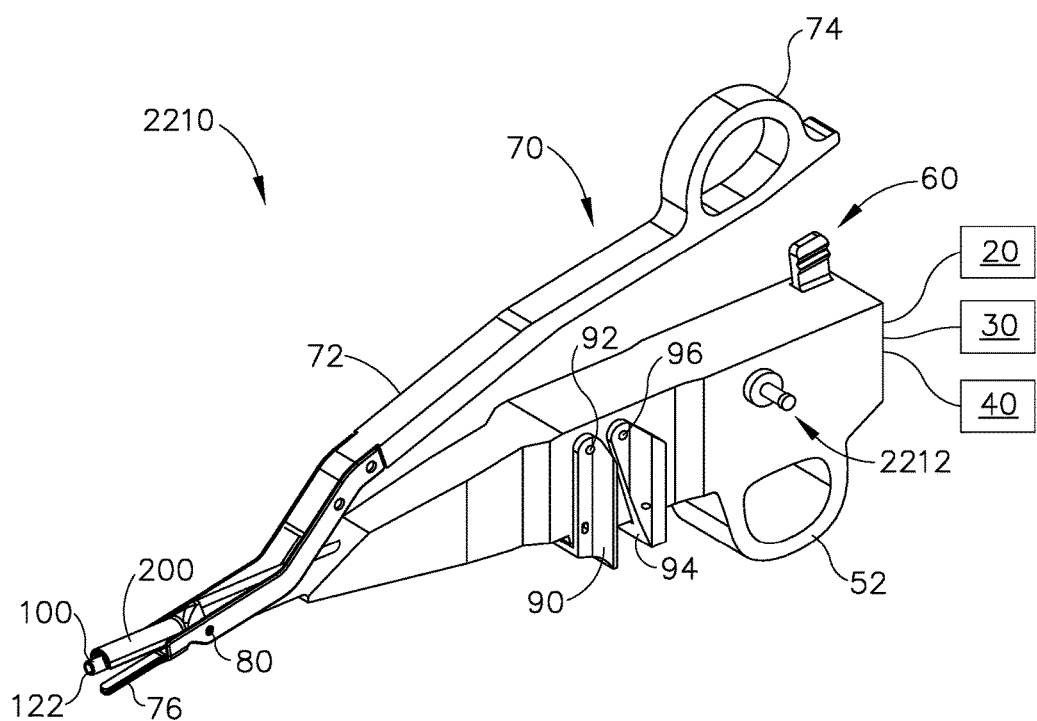
FIG. 50 depicts a perspective view of an exemplary alternative surgical system with an ultrasonic surgical instrument having a backflow valve.

FIGS. 48-49 depict another exemplary end effector (2100) that is configured to seal spotty bleeding by encouraging coagulation of tissue with a heated fluid, such as a saline solution. End effector (2100) may be readily incorporated into instrument (10) described above. End effector (2100) includes a powered electrode (2102) that cooperates with a grounded electrode (2104) for heating the saline solution during application on the tissue in use. More particularly, powered electrode (2102) extends longitudinally along an exterior of ultrasonic blade (100), whereas grounded electrode (2104) extends along the longitudinal axis through ultrasonic blade (100). Powered electrode (2102) is positioned between irrigation flue (200) and ultrasonic blade (100) and extends distally to be adjacent a distal end of ultrasonic blade (100). In contrast, grounded electrode (2104) extends distally beyond the distal end of ultrasonic blade (100) in order to more conveniently provide the return path for electrical power while contacting grounded electrode (2104) directly to tissue with saline solution applied thereon.

Powered electrode (2102) includes a fluid discharge conduit (2106), and grounded electrode (2104) includes a fluid suction conduit (2108) that cooperates with the fluid discharge conduit (2106) for applying and suctioning the saline solution from the tissue in use. Fluid discharge conduit (2106) is fluidly connected to fluid source (30) (see FIG. 1), and fluid suction conduit (2108) is fluidly connected to suction source (40) (see FIG. 1). In use, the saline solution flows along fluid discharge conduit (2106) and discharges from powered electrode (2102) onto the tissue while grounded electrode (2104) suctions the saline solution along the fluid suction conduit (2108) from the tissue. The simultaneous application and suction of the saline solution provides a direct flow path through the saline solution for electrical power to flow from powered electrode (2102) to grounded electrode (2104). The flowing electrical power thereby heats the saline solution by Joule heating, which increases blood coagulation for sealing the tissue. Furthermore, the temperature of the saline solution at the tissue may be adjusted to any desirable temperature by similarly adjusting a flowrate of the saline solution discharged and suctioned from the tissue. The operator may thereby precisely control application of the temperature and location of the heated saline solution specifically between powered and grounded electrodes (2102, 2104).

Exemplary powered and grounded electrodes (2102, 2104) may be alternatively arranged so as to direct electrical power through the fluid to generate Joule heating. Fluid discharge conduit (2106) and fluid suction conduit (2108) may also be alternatively arranged so as to provide and suction fluid in an alternative arrangement that still provides for the flow of electrical power therethrough. While electrodes (2102, 2104) are thus shown in exemplary end effector (2100) as tubular electrodes defining conduits (2106, 2108), it will be appreciated that the invention is not intended to be limited to the particular arrangement as shown and described herein.

V. Exemplary Backflow Valve for Removing Tissue Obstructions

In some instances, it may be desirable to modify instrument (10) to actively flush debris, such as a blockage of coagulated blood and/or tissue particles, from lumen (122) of ultrasonic blade (100). While various features have been described herein to reduce the likelihood of debris collecting within ultrasonic blade (100) to inhibit such a blockage, actively flushing fluid, such as saline solution, through ultrasonic blade (100) may be beneficial for dislodging and removing debris in some instances. For example, instrument (10) may be modified with a valve, such as a backflow valve (2212), configured to fluidly connect ultrasonic blade (100) to fluid source (30) and backflow saline solution through lumen (122) for dislodging the debris. In turn, the debris and saline solution is discharged from lumen (122), at which time the operator may resume operation of instrument (10) as discussed above. While the following examples are provided in the context of instrument (2210), which is a modified form of instrument (10), it should be understood that the following examples may alternatively be incorporated into other instruments discussed herein and other various kinds of instruments.

Figure 51:
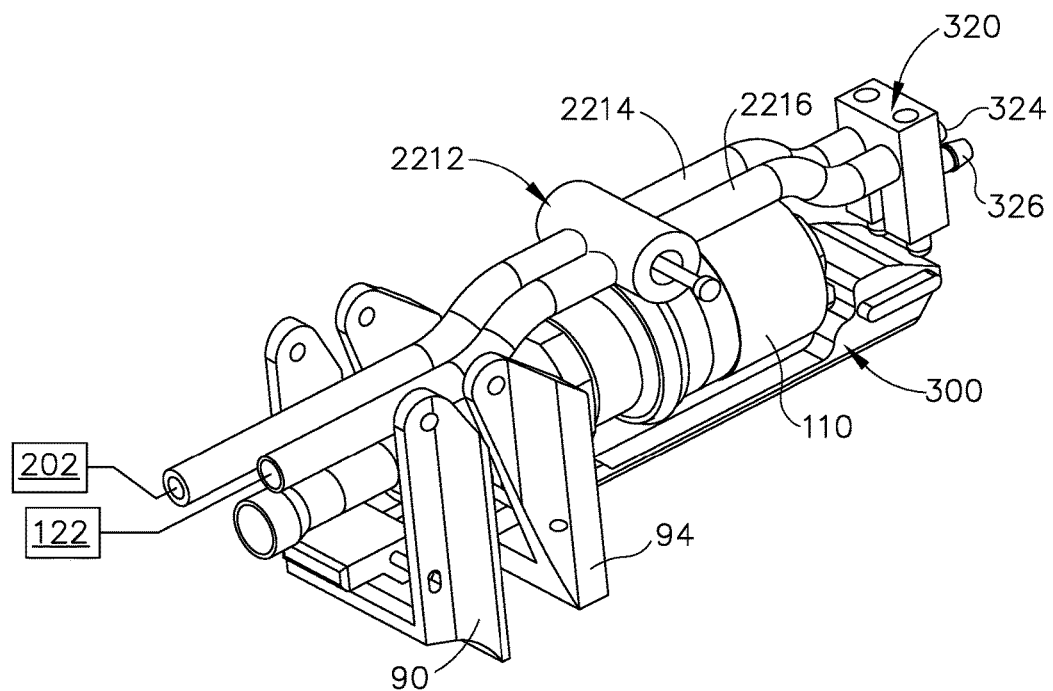
FIG. 51 depicts an enlarged perspective view of the surgical instrument of FIG. 50 having various components removed for clarity.
Figure 52A:
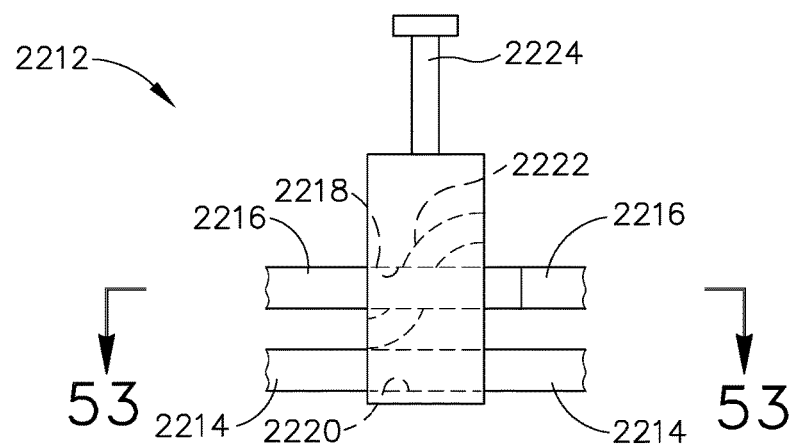
FIG. 52A depicts a top plan view of the backflow valve of FIG. 50 in a non-backflow state.
Figure 52B:
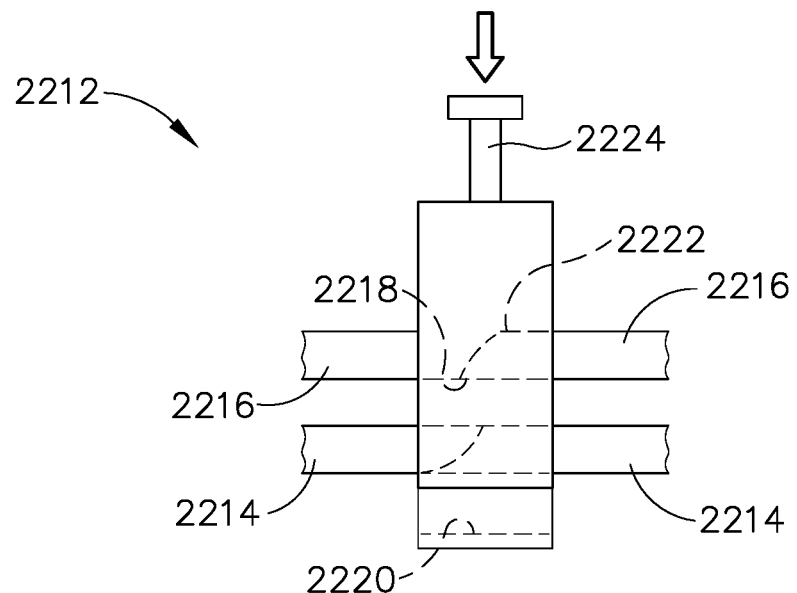
FIG. 52B depicts a top plan view of the backflow valve of FIG. 50 in a backflow state.
Figure 53:
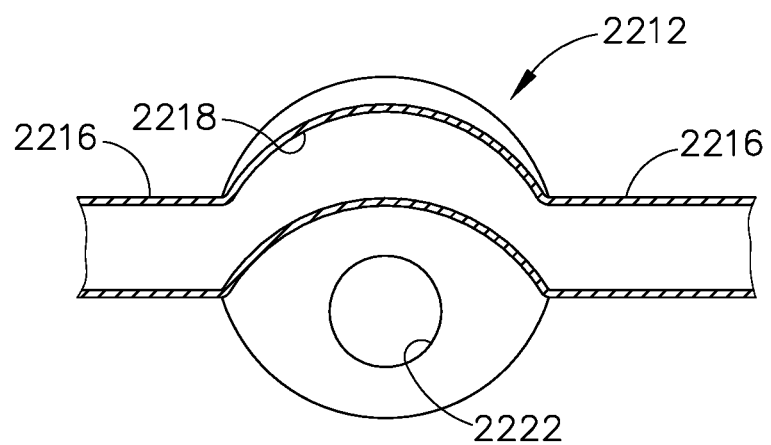
FIG. 53 depicts a cross-sectional view of the backflow valve of FIG. 50, taken along section line 53-53 of FIG. 52A.

FIGS. 50-53 depicts an instrument (2210) having a backflow valve in the form of a backflow trumpet valve (2212). As shown in FIGS. 51-53, backflow trumpet valve (2212) is fluidly connected in line with fluid tube (2214) and suction tube (2216) and is configured to selectively move between a non-backflow position and a backflow position. In the non-backflow position, backflow trumpet valve (2212) directs saline solution, or other fluid, and fluid suction, therethrough such that fluid tube (2214) and suction tube (2216) operate as fluid tube (370) (see FIG. 2) and suction tube (380) (see FIG. 2) discussed above in greater detail for transecting tissue. In the backflow position, backflow trumpet valve (2212) instead fluidly disconnects suction tube (2216) from suction inlet port (326) and fluidly connects suction tube (2216) to suction tube (380) to fluid inlet port (324). The backflow trumpet valve (2212) in the backflow position is thus configured to redirect fluid along the suction tube (2216) and into lumen (122) for dislodging debris and flushing debris from limen (122) of ultrasonic blade (100).

FIGS. 52A-52B show backflow trumpet valve (2212) in non-backflow and backflow positions, respectively. As shown in FIG. 52A, backflow trumpet valve (2212) has a suction channel (2218) and a fluid channel (2220) fluidly connected to fluid tube (2214) and suction tube (2216) in the non-backflow position. In addition, backflow trumpet valve (2212) includes a backflow channel (2222) offset and fluidly isolated from each of suction and fluid channels (2218, 222). Backflow channel (2222) is generally not fluidly connected to fluid tube (2214) nor suction tube (2216).

In order to move backflow trumpet valve (2212) to the backflow position, backflow trumpet valve (2212) also has an actuator in the form of an actuator button (2226) configured to depress toward fluid and suction tubes (2214, 2216) for similarly moving suction, fluid, and backflow channels (2218, 2220, 2222). Suction and fluid channels (2218, 2220) thus fluidly disconnect from fluid and suction tubes (2214, 2216), whereas backflow channel fluidly connects between fluid inlet port (324) via fluid tube (2214) and lumen (122) via suction tube (2216). As shown in FIG. 52B, backflow channel (2222) is fluidly connected to to flush ultrasonic blade (100) of debris, whereas neither suction channel (2218) nor fluid channel (2200) is fluidly connected to either fluid tube (2214) or suction tube (2216). In some versions, actuator button (2226) is resiliently biased toward the non-backflow position (e.g., via a coil spring or leaf spring, etc.), such that the backflow trumpet valve (2212) generally remains in the non-backflow position unless the operator selectively depresses actuator button (2226).

Exemplary suction channel (2218) and fluid channel (2220) generally align respectively with fluid tube (2214) and suction tube (2216) as shown in FIGS. 52A-53. However, suction channel (2218) generally curves around backflow channel (2222), which to some extent extends transversely relative to suction and fluid channels (2218, 2220) so as to fluidly connect fluid tube (2214) to suction tube (2216). However, it will be appreciated that alternative valves may be fluidly connected between fluid source (30) and lumen (122) for flushing fluid through ultrasonic blade (100). The invention is thus not intended to be unnecessarily limited to backflow trumpet valve (2212) as described herein.

Figure 54A:
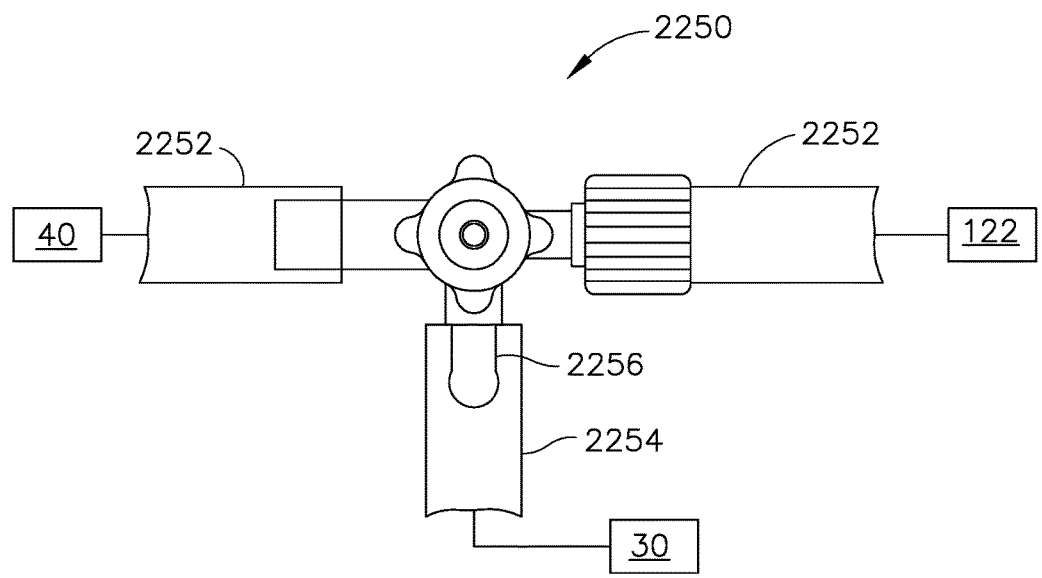
FIG. 54A depicts a top plan view of an exemplary alternative backflow valve in a non-backflow state.
Figure 54B:
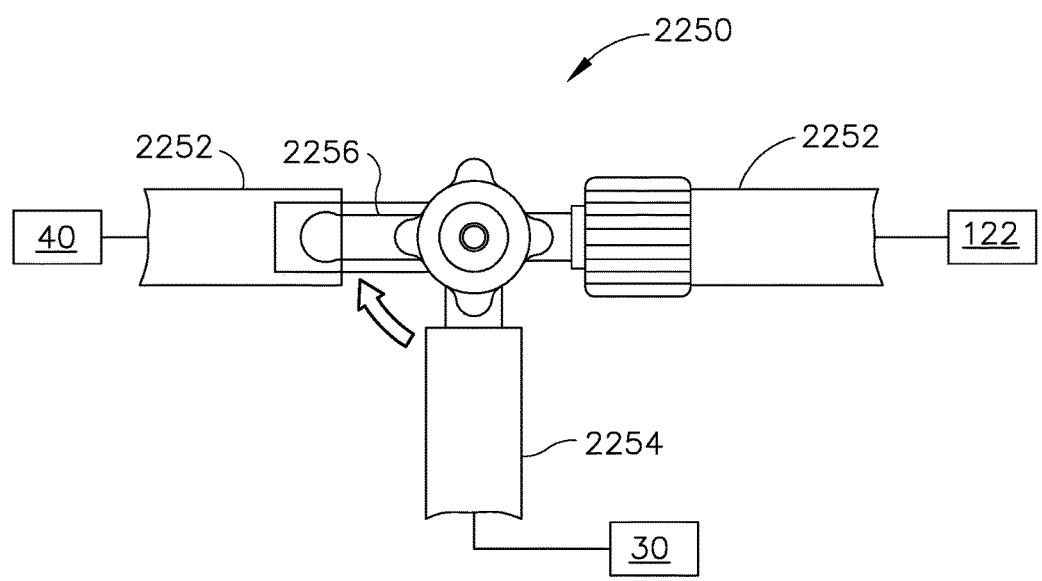
FIG. 54B depicts a top plan view of the backflow valve of FIG. 54A in a backflow state.

By way of example, an alternative valve may be in the form of a backflow stopcock valve (2250) as shown in FIGS. 54A-54B. Backflow stopcock valve (2250) is fluidly connected in line with suction tube (2252), which fluidly connects suction source (40) to lumen (122) in a non-backflow position as shown in FIG. 54A. Backflow stopcock valve (2250) further includes a coupling tube (2254) fluidly connected to fluid tube (370) (see FIG. 2). Coupling tube (2254) is effectively closed in the non-backflow position so as to inhibit fluid from being introduced into suction tube (2252).

As shown in FIG. 54B, the operator selectively moves backflow stopcock valve (2250) to a backflow position, which fluidly connects coupling tube (2254) to lumen (122) via suction tube (2252). Backflow stopcock valve (2250) also effectively closes a portion of suction tube (2252) to fluidly disconnect suction source (40) from lumen (122). In the present example, the operator manipulates an actuator switch (2256) between the standard and backflow positions as desired for directing fluid along lumen (122), dislodging debris, and discharging the fluid and debris from ultrasonic blade (100) (see FIG. 50). Other suitable valve configurations will be apparent to those of ordinary skill in the art in view of the teachings herein.

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An instrument, comprising: (a) an ultrasonic blade, wherein the ultrasonic blade defines a distal opening, wherein the ultrasonic blade is operable in a first mode to emulsify tissue that is distally positioned relative to the ultrasonic blade, wherein the ultrasonic blade is further operable in a second mode to transect and seal tissue that is transversely positioned relative to the ultrasonic blade; (b) a first fluid port in communication with the distal opening of the ultrasonic blade; (c) a clamp arm, wherein the clamp arm is pivotable toward and away from the ultrasonic blade; (d) an irrigation member positioned adjacent to the distal end of the ultrasonic blade; and (e) a second fluid port in communication with the irrigation member.

Example 2

The instrument of Example 1, further comprising: (a) a first actuator, wherein the first actuator is operable to activate the ultrasonic blade in the first mode to emulsify tissue that is distally positioned relative to the ultrasonic blade; and (b) a second actuator, wherein the second actuator is operable to activate the ultrasonic blade in the second mode to transect and seal tissue that is transversely positioned relative to the ultrasonic blade.

Example 3

The instrument of any one or more of Examples 1 through 2, further comprising a valve assembly, wherein the valve assembly is configured to selectively open and close communication of suction to the first fluid port.

Example 4

The instrument of Example 3, wherein the valve assembly is further configured to selectively open and close communication of fluid to the second fluid port.

Example 5

The instrument of Example 4, further comprising: (a) a first actuator, wherein the first actuator is operable to activate the ultrasonic blade in the first mode to emulsify tissue that is distally positioned relative to the ultrasonic blade; and (b) a second actuator, wherein the second actuator is operable to activate the ultrasonic blade in the second mode to transect and seal tissue that is transversely positioned relative to the ultrasonic blade.

Example 6

The instrument of Example 5, wherein the first actuator is further operable to selectively change a state of the valve assembly, wherein the valve assembly is configured to open communication of suction to the first fluid port and open communication of fluid to the second fluid port in response to actuation of the first actuator.

Example 7

The instrument of Example 6, further comprising a cam sled, wherein the cam sled is configured to move between a first position and a second position in response to actuation of the first actuator, wherein the cam sled in the second position is configured to actuate the valve assembly to thereby open communication of suction to the first fluid port and open communication of fluid to the second fluid port in response to actuation of the first actuator.

Example 8

The instrument of Example 7, wherein the cam sled is positioned proximally in relation to the first actuator.

Example 9

The instrument of any one or more of Examples 1 through 8, further comprising a waveguide assembly, wherein the waveguide assembly comprises a lateral opening, wherein the first fluid port is positioned in the lateral opening.

Example 10

The instrument of Example 9, further comprising a tube wherein the tube is disposed in the lateral opening to couple with the first fluid port.

Example 11

The instrument of any one or more of Examples 1 through 10, further comprising a suction source coupled with the first fluid port.

Example 12

The instrument of any one or more of Examples 1 through 11, wherein the irrigation member comprises an irrigation flue, wherein the irrigation flue extends along an arc.

Example 13

The instrument of Example 12, wherein the irrigation flue defines a distal opening, wherein the distal opening is configured to expel fluid from the second fluid port.

Example 14

The instrument of any one or more of Examples 12 through 13, wherein the irrigation flue has a semicircular cross-sectional profile.

Example 15

The instrument of any one or more of Examples 12 through 14, wherein the irrigation flue is positioned on one side of the ultrasonic blade, wherein the clamp arm comprises a clamp pad positioned on another side of the ultrasonic blade.

Example 16

The instrument of Example 15, wherein the ultrasonic blade defines a longitudinal axis, wherein the clamp pad is angularly offset from the irrigation flue about the longitudinal axis by 180°.

Example 17

The instrument of any one or more of Examples 1 through 16, further comprising a handle assembly.

Example 18

The instrument of any one or more of Examples 1 through 18, further comprising a ratcheting or detent feature, wherein the ratcheting or detent feature is configured to one or both of indicate or selectively lock the clamp arm at a first pivotal position relative to the ultrasonic blade and at a second pivotal position relative to the ultrasonic blade, wherein the first pivotal position is associated with the first mode, wherein the second pivotal position is associated with the second mode.

Example 19

The instrument of Example 18, wherein the clamp arm in the first pivotal position is positioned to define a gap between a clamp pad of the clamp arm and the ultrasonic blade, wherein the clamp arm in the second pivotal position is positioned to engage the ultrasonic blade with the clamp pad.

Example 20

The instrument of any one or more of Examples 18 through 19, further comprising a handle assembly, wherein the clamp arm is pivotably coupled with the handle assembly, wherein the ratcheting or detent feature comprises: (i) at least one pawl on the clamp arm, and (ii) at least one pawl on the handle assembly.

Example 21

The instrument of any one or more of Examples 1 through 20, wherein the ultrasonic blade comprises a distal wall defining two or more opening regions.

Example 22

The instrument of Example 21, wherein the ultrasonic blade defines a length, wherein the distal wall extends along only as portion of the length of the ultrasonic blade.

Example 23

The instrument of any one or more of Examples 1 through 22, wherein the ultrasonic blade has a convex or concave distal edge surrounding the distal opening.

Example 24

The instrument of any one or more of Examples 1 through 23, further comprising an RF electrode, wherein the RF electrode is operable to provide RF energy to tissue.

Example 25

The instrument of Example 24, wherein the RF electrode is located on the irrigation member.

Example 26

The instrument of any one or more of Examples 1 through 25, further comprising an angularly spaced array of RF electrodes, wherein the RF electrodes are operable to provide RF energy to tissue.

Example 27

The instrument of Example 1, further comprising a first RF electrode extending along the clamp arm and configured to provide RF energy to tissue.

Example 28

The instrument of Example 27, wherein the ultrasonic blade is configured to be electrically grounded as a ground electrode.

Example 29

The instrument of any one or more of Examples 27 through 28, wherein the clamp arm includes: (i) a clamp member configured to engage the ultrasonic blade, and (ii) a pair of opposing lateral sides positioned such that the clamp member extends therebetween, wherein the first RF electrode extends along at least one of the pair of opposing lateral sides.

Example 30

The instrument of Example 29, further comprising a second RF electrode extending along at least one of the pair of opposing lateral sides and configured to provide RF energy to tissue.

Example 31

The instrument of Example 30, wherein the first and second RF electrodes extend along respective opposing lateral sides.

Example 32

The instrument of Example 28, wherein the clamp arm includes: (i) a clamp member configured to engage the ultrasonic blade, and (ii) a pair of opposing lateral sides positioned such that the clamp member extends therebetween, wherein the first RF electrode extends along the clamp member.

Example 33

The instrument of Example 32, further comprising a first ground electrode extending along the clamp member and configured to be electrically grounded.

Example 34

The instrument of any one or more of Examples 32 through 33, further comprising a second RF electrode extending along the clamp member and configured to provide RF energy to tissue.

Example 35

The instrument of any one or more of Examples 32 through 34, further comprising a second ground electrode extending along the clamp member and configured to be electrically grounded.

Example 36

The instrument of Example 1, further comprising a first electrode extending within the ultrasonic blade and through the distal opening and configured to conduct electrical energy therethrough.

Example 37

The instrument of Example 36, further comprising a second electrode extending externally along the ultrasonic blade and configured to conduct electrical energy therethrough.

Example 38

The instrument of Example 37, wherein the first electrode is configured to provide electrical energy to tissue, and wherein the second electrode configured to be electrically grounded for receiving electrical energy from the first electrode.

Example 39

The instrument of any one or more of Examples 37 through 38, wherein the first electrode includes a first fluid conduit configured to direct fluid therealong.

Example 40

The instrument of any one or more of Examples 37 through 39, wherein the second electrode includes a second fluid conduit configured to direct fluid therealong.

Example 41

The instrument of Example 40, wherein the second fluid conduit is configured to fluidly connect to a fluid source for discharging fluid therefrom, wherein the first fluid conduit is configured to fluidly connect a vacuum for suctioning the fluid discharged from the second fluid conduit, and wherein the first and second electrodes are configured to heat the fluid via electrical energy conducted therebetween.

Example 42

The instrument of Example 1, wherein the ultrasonic blade includes a distal beveled tip, and wherein the distal opening extends through the distal beveled tip.

Example 43

The instrument of Example 42, wherein the distal beveled tip is configured to cut a Glisson capsule.

Example 44

The instrument of Example 1, further comprising a backflow valve fluidly connected between the first fluid port and the distal opening and between the second fluid port and the irrigation member, wherein the backflow valve is configured to selectively move between a non-backflow position and a backflow position, wherein the backflow valve in the non-backflow position is configured to fluidly connect the first fluid port to the distal opening and fluidly connect the second fluid port to the irrigation member, and wherein the backflow valve in the backflow position is configured to fluidly connect the second fluid port to the distal opening for directing fluid through the ultrasonic blade and discharging the fluid from the distal opening.

Example 45

The instrument of Example 44, wherein the backflow valve comprises a trumpet valve.

Example 46

The instrument of Example 44, wherein the backflow valve comprises a stopcock valve.

Example 47

A method of manipulating tissue, the method comprising: (a) emulsifying tissue with an ultrasonic blade, wherein the ultrasonic blade defines a longitudinal axis and has a distal end, wherein the tissue is distal to the ultrasonic blade during the act of emulsifying tissue, (b) clamping tissue against a side of the ultrasonic blade with a clamp arm, wherein the clamped tissue is positioned lateral to the longitudinal axis; and (c) activating the ultrasonic blade to transect and seal the tissue clamped against the side of the ultrasonic blade.

Example 48

The method of Example 47, further comprising communicating fluid to the tissue during the act of emulsifying tissue.

Example 49

The method of any one or more of Examples 47 through 48, further comprising communicating suction during the act of emulsifying tissue.

Example 50

The method of Example 49, wherein the ultrasonic blade defines a lumen, wherein the act of communicating suction comprises communicating suction through the lumen.

Example 51

The method of any one or more of Examples 47 through 50, wherein the act of emulsifying tissue comprises emulsifying liver parynchema.

Example 52

The method of Example 51, wherein the act of clamping tissue comprises clamping a blood vessel or biliary duct of the liver.

Example 53

The method of any one or more of Examples 47 through 52, further comprising applying RF energy to tissue.

Example 54

The method of Example 53, wherein the acts of emulsifying, clamping, and applying RF energy are performed using a single instrument, wherein the single instrument comprises the ultrasonic blade, the clamp arm, and at least one RF electrode.

Example 55

The method of any one or more of Examples 47 through 54, wherein a first electrode configured to provide RF energy extends along the clamp member, and the method further comprises applying RF energy to tissue with the first electrode.

Example 56

The method of any one or more of Examples 47 through 55, wherein a second electrode configured to provide electrical energy is positioned proximate to the ultrasonic blade, and the method further comprises: (a) discharging fluid from the second electrode; (b) applying the electrical energy to the fluid via the second electrode; and (c) heating the fluid with the applied electrical energy.

Example 57

The method of any one or more of Examples 47 through 56, further comprising cutting a Glisson capsule with the ultrasonic blade.

Example 58

The method of any one or more of Examples 47 through 57, further comprising: (a) directing fluid from a fluid source through ultrasonic blade; (b) flushing debris from the ultrasonic blade toward a distal opening in the ultrasonic blade; and (c) discharging the fluid and the debris from the distal opening.

VII. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An instrument, comprising:
(a) an ultrasonic blade, wherein the ultrasonic blade defines a distal opening, wherein the ultrasonic blade is operable in a first mode to emulsify tissue that is distally positioned relative to the ultrasonic blade, wherein the ultrasonic blade is further operable in a second mode to transect and seal tissue that is transversely positioned relative to the ultrasonic blade;
(b) a first fluid port in communication with the distal opening of the ultrasonic blade;
(c) a clamp arm, wherein the clamp arm is pivotable toward and away from the ultrasonic blade;
(d) an irrigation member positioned adjacent to a distal end of the ultrasonic blade; and
(e) a second fluid port in communication with the irrigation member.

2. The instrument of claim 1, further comprising:
(a) a first actuator, wherein the first actuator is operable to activate the ultrasonic blade in the first mode to emulsify tissue that is distally positioned relative to the ultrasonic blade; and
(b) a second actuator, wherein the second actuator is operable to activate the ultrasonic blade in the second mode to transect and seal tissue that is transversely positioned relative to the ultrasonic blade.

3. The instrument of claim 1, further comprising a valve assembly, wherein the valve assembly is configured to selectively open and close communication of suction to the first fluid port.

4. The instrument of claim 3, wherein the valve assembly is further configured to selectively open and close communication of fluid to the second fluid port.

5. The instrument of claim 4, further comprising:
(a) a first actuator, wherein the first actuator is operable to activate the ultrasonic blade in the first mode to emulsify tissue that is distally positioned relative to the ultrasonic blade; and
(b) a second actuator, wherein the second actuator is operable to activate the ultrasonic blade in the second mode to transect and seal tissue that is transversely positioned relative to the ultrasonic blade.

6. The instrument of claim 5, wherein the first actuator is further operable to selectively change a state of the valve assembly, wherein the valve assembly is configured to open communication of suction to the first fluid port and open communication of fluid to the second fluid port in response to actuation of the first actuator.

7. The instrument of claim 6, further comprising a cam sled, wherein the cam sled is configured to move between a first position and a second position in response to actuation of the first actuator, wherein the cam sled in the second position is configured to actuate the valve assembly to thereby open communication of suction to the first fluid port and open communication of fluid to the second fluid port in response to actuation of the first actuator.

8. The instrument of claim 7, wherein the cam sled is positioned proximally in relation to the first actuator.

9. The instrument of claim 1, further comprising a waveguide assembly, wherein the waveguide assembly comprises a lateral opening, wherein the first fluid port is positioned in the lateral opening.

10. The instrument of claim 1, wherein the irrigation member comprises an irrigation flue, wherein the irrigation flue extends along an arc.

11. The instrument of claim 10, wherein the irrigation flue defines a distal opening, wherein the distal opening is configured to expel fluid from the second fluid port.

12. The instrument of claim 10, wherein the irrigation flue has a semicircular cross-sectional profile.

13. The instrument of any claim 10, wherein the irrigation flue is positioned on one side of the ultrasonic blade, wherein the clamp arm comprises a clamp pad positioned on another side of the ultrasonic blade.

14. The instrument of claim 1, further comprising a ratcheting or detent feature, wherein the ratcheting or detent feature is configured to one or both of indicate or selectively lock the clamp arm at a first pivotal position relative to the ultrasonic blade and at a second pivotal position relative to the ultrasonic blade, wherein the first pivotal position is associated with the first mode, wherein the second pivotal position is associated with the second mode, wherein the clamp arm in the first pivotal position is positioned to define a gap between a clamp pad of the clamp arm and the ultrasonic blade, wherein the clamp arm in the second pivotal position is positioned to engage the ultrasonic blade with the clamp pad.

15. The instrument of claim 1, further comprising an RF electrode, wherein the RF electrode is operable to provide RF energy to tissue.

16. The instrument of claim 15, wherein the RF electrode is located on the irrigation member.

17. The instrument of claim 1, further comprising a first electrode extending within the ultrasonic blade and through the distal opening and configured to conduct electrical energy therethrough.

18. The instrument of claim 1, further comprising a backflow valve fluidly connected between the first fluid port and the distal opening and between the second fluid port and the irrigation member, wherein the backflow valve is configured to selectively move between a non-backflow position and a backflow position, wherein the backflow valve in the non-backflow position is configured to fluidly connect the first fluid port to the distal opening and fluidly connect the second fluid port to the irrigation member, and wherein the backflow valve in the backflow position is configured to fluidly connect the second fluid port to the distal opening for directing fluid through the ultrasonic blade and discharging the fluid from the distal opening.

19. A method of manipulating tissue with an instrument, wherein the instrument includes (a) an ultrasonic blade, wherein the ultrasonic blade defines a distal opening, wherein the ultrasonic blade is operable in a first mode to emulsify tissue that is distally positioned relative to the ultrasonic blade, wherein the ultrasonic blade is further operable in a second mode to transect and seal tissue that is transversely positioned relative to the ultrasonic blade; (b) a first fluid port in communication with the distal opening of the ultrasonic blade; (c) a clamp arm, wherein the clamp arm is pivotable toward and away from the ultrasonic blade; (d) an irrigation member positioned adjacent to a distal end of the ultrasonic blade; and (e) a second fluid port in communication with the irrigation member, the method comprising:
(a) emulsifying tissue with the ultrasonic blade, wherein the ultrasonic blade defines a longitudinal axis and has the distal end, wherein the tissue is distal to the ultrasonic blade during the act of emulsifying tissue;
(b) clamping tissue against a side of the ultrasonic blade with the clamp arm, wherein the clamped tissue is positioned lateral to the longitudinal axis; and
(c) activating the ultrasonic blade to transect and seal the tissue clamped against the side of the ultrasonic blade.

20. An instrument, comprising:
(a) an ultrasonic blade, wherein the ultrasonic blade defines a distal opening, wherein the ultrasonic blade is operable in a first mode to emulsify tissue that is distally positioned relative to the ultrasonic blade, wherein the ultrasonic blade is further operable in a second mode to transect and seal tissue that is transversely positioned relative to the ultrasonic blade;

(b) a first fluid port in communication with the distal opening of the ultrasonic blade;
(c) a clamp arm, wherein the clamp arm is pivotable toward and away from the ultrasonic blade;
(d) an irrigation member positioned adjacent to a distal end of the ultrasonic blade;
(e) a second fluid port in communication with the irrigation member;
a valve assembly configured to selectively open and close communication of suction to the first fluid port.

* * * * *